United States Patent
Firminger et al.

(10) Patent No.: US 9,892,435 B2
(45) Date of Patent: Feb. 13, 2018

(54) COMPUTATIONAL SYSTEMS AND METHODS FOR HEALTH SERVICES PLANNING AND MATCHING

(75) Inventors: Shawn P. Firminger, Redmond, WA (US); Jason Garms, Redmond, WA (US); Roderick A. Hyde, Redmond, WA (US); Edward K. Y. Jung, Bellevue, WA (US); Chris Demetrios Karkanias, Sammamish, WA (US); Eric C. Leuthardt, St. Louis, MO (US); Royce A. Levien, Lexington, MA (US); Richard T. Lord, Tacoma, WA (US); Robert W. Lord, Seattle, WA (US); Mark A. Malamud, Seattle, WA (US); John D. Rinaldo, Jr., Bellevue, WA (US); Clarence T. Tegreene, Bellevue, WA (US); Kristin M. Tolle, Redmond, WA (US); Lowell L. Wood, Jr., Bellevue, WA (US)

(73) Assignee: GEARBOX LLC, Bellevue, WA (US)

( * ) Notice: Subject to any disclaimer, the term of this patent is extended or adjusted under 35 U.S.C. 154(b) by 86 days.

(21) Appl. No.: 12/660,143

(22) Filed: Feb. 19, 2010

(65) Prior Publication Data

US 2010/0274578 A1 Oct. 28, 2010

Related U.S. Application Data

(63) Continuation-in-part of application No. 12/381,377, filed on Mar. 10, 2009, now abandoned, and a continuation-in-part of application No. 12/381,680, filed on Mar. 12, 2009, now abandoned, and a continuation-in-part of application No. 12/587,239, filed on Oct. 2, 2009, now abandoned, and a continuation-in-part of application No. 12/587,313, (Continued)

(51) Int. Cl.
*G06Q 50/22* (2012.01)
*G06Q 30/06* (2012.01)
*G06F 19/00* (2011.01)

(52) U.S. Cl.
CPC ......... *G06Q 30/06* (2013.01); *G06F 19/328* (2013.01); *G06F 19/3418* (2013.01); *G06F 19/3481* (2013.01); *G06Q 50/22* (2013.01); *G06F 19/327* (2013.01); *G06F 19/345* (2013.01); *G06F 19/3425* (2013.01); *G06F 19/3443* (2013.01)

(58) Field of Classification Search
CPC ..... G06Q 50/22; G06Q 50/24; A61B 5/14551
USPC .......................................... 705/2–3; 607/45
See application file for complete search history.

(56) References Cited

U.S. PATENT DOCUMENTS

| | | |
|---|---|---|
| 5,106,482 A | 4/1992 | Milstein et al. |
| 5,716,382 A | 2/1998 | Snell |
| 5,718,247 A | 2/1998 | Frankel |
| 5,738,104 A | 4/1998 | Lo et al. |
| 5,911,132 A | 6/1999 | Sloane |
| 5,926,794 A | 7/1999 | Fethe |
| 6,014,654 A | 1/2000 | Ariyoshi |
| 6,019,507 A | 2/2000 | Takaki |
| 6,023,685 A | 2/2000 | Brett et al. |

(Continued)

OTHER PUBLICATIONS

"Web sites let patients find like-minded physicians", amednews.com, Mar. 27, 2006.*

(Continued)

*Primary Examiner* — Joseph D Burgess

(57) ABSTRACT

Systems and methods are described relating to accepting an indication of at least one attribute of an individual; accepting sensor data about the individual; presenting a set of health care options at least partially based on the accepting sensor data about the individual; and providing a matching system for procurement of at least one selected health service option.

51 Claims, 31 Drawing Sheets

Related U.S. Application Data filed on Oct. 5, 2009, and a continuation-in-part of application No. 12/589,124, filed on Oct. 16, 2009, now abandoned, and a continuation-in-part of application No. 12/589,171, filed on Oct. 19, 2009, and a continuation-in-part of application No. 12/589,639, filed on Oct. 26, 2009, now abandoned, and a continuation-in-part of application No. 12/589,728, filed on Oct. 27, 2009, now abandoned, and a continuation-in-part of application No. 12/590,104, filed on Nov. 2, 2009, now abandoned, and a continuation-in-part of application No. 12/590,163, filed on Nov. 3, 2009, and a continuation-in-part of application No. 12/590,250, filed on Nov. 4, 2009, now abandoned, and a continuation-in-part of application No. 12/590,335, filed on Nov. 5, 2009, and a continuation-in-part of application No. 12/592,439, filed on Nov. 24, 2009, now abandoned, and a continuation-in-part of application No. 12/592,541, filed on Nov. 25, 2009, and a continuation-in-part of application No. 12/592,768, filed on Dec. 2, 2009, now Pat. No. 8,095,384, and a continuation-in-part of application No. 12/592,859, filed on Dec. 3, 2009, now abandoned, and a continuation-in-part of application No. 12/655,474, filed on Dec. 30, 2009, now abandoned, and a continuation-in-part of application No. 12/655,580, filed on Dec. 31, 2009, now abandoned, and a continuation-in-part of application No. 12/657,429, filed on Jan. 20, 2010, and a continuation-in-part of application No. 12/657,498, filed on Jan. 21, 2010, and a continuation-in-part of application No. 12/657,980, filed on Jan. 29, 2010, and a continuation-in-part of application No. 12/658,056, filed on Feb. 1, 2010, and a continuation-in-part of application No. 12/658,166, filed on Feb. 3, 2010, and a continuation-in-part of application No. 12/658,256, filed on Feb. 4, 2010, and a continuation-in-part of application No. 12/660,029, filed on Feb. 18, 2010, now abandoned.

(56) References Cited

U.S. PATENT DOCUMENTS

| | | | |
|---|---|---|---|
| 6,067,523 A | 5/2000 | Bair et al. | |
| 6,012,053 A | 6/2000 | Pant et al. | |
| 6,155,974 A | 12/2000 | Fish | |
| 6,231,187 B1 | 5/2001 | Munoz et al. | |
| 6,315,719 B1 | 11/2001 | Rode et al. | |
| 6,334,192 B1 | 12/2001 | Karpf | |
| 6,480,730 B2 | 11/2002 | Darrow et al. | |
| 6,584,445 B2 | 6/2003 | Papageorge | |
| 6,807,531 B1 | 10/2004 | Kanai | |
| 6,829,499 B1 | 12/2004 | Shahinpoor et al. | |
| 6,915,297 B2 | 7/2005 | Chou | |
| 7,079,977 B2 | 7/2006 | Osorio et al. | |
| 7,120,486 B2 | 10/2006 | Leuthardt et al. | |
| 7,194,301 B2 | 3/2007 | Jenkins et al. | |
| 7,283,856 B2 | 10/2007 | Boling | |
| 7,387,607 B2 | 6/2008 | Holt et al. | |
| 7,406,453 B2 | 7/2008 | Mundie et al. | |
| 7,424,409 B2 | 9/2008 | Ben-Gal et al. | |
| 7,502,650 B2 | 3/2009 | Kieval | |
| 7,519,540 B2 | 4/2009 | Mayaud | |
| 7,711,580 B1 | 5/2010 | Hudson | |
| 7,720,708 B1 | 5/2010 | Elkins, II et al. | |
| 7,901,368 B2* | 3/2011 | Flaherty | A61H 1/0255 601/33 |
| 7,941,351 B1 | 5/2011 | Rosenfeld et al. | |
| 7,949,580 B1 | 5/2011 | Boyer et al. | |
| 2002/0059132 A1 | 5/2002 | Quay et al. | |
| 2002/0065758 A1* | 5/2002 | Henley | G06F 19/327 705/37 |
| 2002/0141629 A1 | 10/2002 | Schreck | |
| 2003/0046113 A1 | 3/2003 | Johnson et al. | |
| 2003/0091964 A1 | 5/2003 | Yeager | |
| 2003/0101086 A1 | 5/2003 | San Miguel | |
| 2003/0130927 A1 | 7/2003 | Kellam et al. | |
| 2003/0191669 A1 | 10/2003 | Fitzgerald et al. | |
| 2003/0212673 A1 | 11/2003 | Kadayam et al. | |
| 2004/0015337 A1* | 1/2004 | Thomas | G06Q 50/24 703/11 |
| 2004/0193529 A1 | 9/2004 | Asher et al. | |
| 2005/0125289 A1 | 6/2005 | Beyda et al. | |
| 2005/0149364 A1 | 7/2005 | Ombrellaro | |
| 2005/0177051 A1* | 8/2005 | Almen | A61B 5/02405 600/509 |
| 2006/0136264 A1* | 6/2006 | Eaton | G06Q 30/0206 705/2 |
| 2006/0143043 A1 | 6/2006 | McCallie, Jr. et al. | |
| 2006/0230033 A1 | 10/2006 | Halevy et al. | |
| 2006/0279732 A1* | 12/2006 | Wang | G01J 3/02 356/326 |
| 2006/0290885 A1 | 12/2006 | Covannon et al. | |
| 2007/0027714 A1 | 2/2007 | Fenno | |
| 2007/0087901 A1 | 4/2007 | Brassil et al. | |
| 2007/0106143 A1 | 5/2007 | Flaherty | |
| 2007/0150024 A1* | 6/2007 | Leyde | A61B 5/0476 607/45 |
| 2007/0156647 A1 | 7/2007 | Shen et al. | |
| 2007/0192300 A1 | 8/2007 | Reuther et al. | |
| 2007/0214008 A1 | 9/2007 | Jung et al. | |
| 2007/0250343 A1 | 10/2007 | Sohal | |
| 2007/0265507 A1 | 11/2007 | de Lemos | |
| 2007/0271119 A1 | 11/2007 | Boerger et al. | |
| 2007/0288262 A1 | 12/2007 | Sakaue et al. | |
| 2008/0065468 A1* | 3/2008 | Berg | G06Q 30/02 705/7.32 |
| 2008/0091086 A1 | 4/2008 | Legere et al. | |
| 2008/0147582 A1 | 6/2008 | Micaelian et al. | |
| 2008/0154912 A1* | 6/2008 | Weber | G06F 17/30663 |
| 2008/0158579 A1 | 7/2008 | Ohga et al. | |
| 2008/0172214 A1 | 7/2008 | Col et al. | |
| 2008/0215570 A1 | 9/2008 | Maloney et al. | |
| 2008/0215627 A1 | 9/2008 | Higgins et al. | |
| 2008/0287746 A1 | 11/2008 | Reisman | |
| 2009/0006419 A1* | 1/2009 | Savitsky | G06Q 50/22 |
| 2009/0023391 A1 | 1/2009 | Falck | |
| 2009/0030334 A1 | 1/2009 | Anderson et al. | |
| 2009/0036757 A1* | 2/2009 | Brockway | A61B 5/0002 600/301 |
| 2009/0043801 A1 | 2/2009 | LeClair et al. | |
| 2009/0083070 A1* | 3/2009 | Giftakis | A61N 1/36132 705/2 |
| 2009/0089084 A1 | 4/2009 | Schoenberg | |
| 2009/0105557 A1 | 4/2009 | Najafi et al. | |
| 2009/0112623 A1 | 4/2009 | Schoenberg | |
| 2009/0118595 A1 | 5/2009 | Greiner et al. | |
| 2009/0149778 A1 | 6/2009 | Naujokat et al. | |
| 2009/0182667 A1 | 7/2009 | Parkes et al. | |
| 2009/0192534 A1 | 7/2009 | Ortiz et al. | |
| 2009/0240527 A1 | 9/2009 | Bluth | |
| 2009/0281835 A1 | 11/2009 | Patwardhan et al. | |
| 2010/0063830 A1 | 3/2010 | Kenedy et al. | |
| 2010/0106518 A1 | 4/2010 | Kuo | |
| 2010/0113950 A1 | 5/2010 | Lin et al. | |
| 2010/0235295 A1 | 9/2010 | Zides et al. | |

OTHER PUBLICATIONS www.archive.org, epilepsy.com, "Find A Doctor", Sep. 13, 2008.*
www.archive.org, naeclocator.org, "Find an Epilepsy Center", Dec. 6, 2008.*
"Insurers Roll Out Hospital Quality Data But Hospital Grades, Cost Info Is Optional", Managed Care Week, Mar. 23, 2003, vol. 13, No. 11, p. 1.*
U.S. Appl. No. 12/660,029, Firminger et al.
U.S. Appl. No. 12/658,256, Firminger et al.

(56) References Cited

OTHER PUBLICATIONS

U.S. Appl. No. 12/658,166, Firminger et al.
U.S. Appl. No. 12/658,056, Firminger et al.
U.S. Appl. No. 12/657,980, Firminger et al.
U.S. Appl. No. 12/657,498, Firminger et al.
U.S. Appl. No. 12/657,429, Firminger et al.
U.S. Appl. No. 12/655,580, Firminger et al.
U.S. Appl. No. 12/655,474, Firminger et al.
U.S. Appl. No. 12/592,859, Firminger et al.
U.S. Appl. No. 12/592,768, Firminger et al.
U.S. Appl. No. 12/592,541, Firminger et al.
U.S. Appl. No. 12/592,439, Firminger et al.
U.S. Appl. No. 12/590,335, Firminger et al.
U.S. Appl. No. 12/590,250, Firminger et al.
U.S. Appl. No. 12/590,163, Firminger et al.
U.S. Appl. No. 12/590,104, Firminger et al.
U.S. Appl. No. 12/589,728, Firminger et al.
U.S. Appl. No. 12/589,639, Firminger et al.
U.S. Appl. No. 12/589,171, Firminger et al.
U.S. Appl. No. 12/589,124, Firminger et al.
U.S. Appl. No. 12/587,313, Firminger et al.
U.S. Appl. No. 12/587,239, Firminger et al.
U.S. Appl. No. 12/381,680, Firminger et al.
U.S. Appl. No. 12/381,377, Firminger et al.
Axelrod et al., "Smoke and Mirrors: Gathering User Requirements for Emerging Affective Systems," 26th Int. Conf. Information Technology Interfaces /TI 2004, Jun. 7-10, 2004, Cavtat, Croatia, pp. 323-328.
"Cancer in Scotland: Radiotherapy Activity Planning for Scotland 2011-2015," available at http://www.scotland.gov.uk/Publications/2006/01/24131719/28, (2006).
Clarke, "IMEC has a brain wave: feed EEG emotion back into games," EE Times online, http://www.eetimes.eu/design/202801063 (Nov. 1, 2007).
Cohn, J.N., Introduction to Surrogate Markers, Circulation 109: IV20-21, American Heart Association, (2004).
Frenkel et al., "An approach for integrating complementary-alternative medicine into primary care," Fam. Pract., 20(3), pp. 324-332 (2003).
Goodman, Clifford S., "Introduction to Health Care Technology Assessment," available at http://www.nlm.nih.gov/nichsr/hta101/ta101_c1.html, (Jan. 2004).
Martinez-Serna et al., "Symptom Priority Ranking in the Care of Gastroesophageal Reflux: A Review of 1,850 Cases," Dig Dis, 17:219-224 (1999).
Nikovski, D., "Constructing Bayesian Networks for Medical Diagnosis from Incomplete and Partially Correct Statistics," IEEE Transactions on Knowledge and Data Engineering, vol. 12:4, pp. 509-516 (2000).
Physorg.com, "New mini-sensor may have biomedical and security applications," Nov. 1, 2007, http://www.physorg.com/news113151078.html.
Sanfey, "Social Decision-Making: Insights from Game Theory and Neuroscience," Science, vol. 318, pp. 598-601 (Oct. 26, 2007).
Tarricone et al., "Economic evaluation of nimesulide versus diclofenac in the treatment of osteoarthritis in France, Italy and Spain," Clin. Drug Invest. 21(7) pp. 453-464 (2001).
MediBid; "MediBid is The Marketplace for Medicine®"; printed on Apr. 25, 2011; pp. 1-2; located at http://www.medibid.com.
Medicine Online; printed on Apr. 25, 2011; pp. 1-2; located at http://www.medicineonline.com.
Rustad, Mitch; "Bid-For-Surgery Web Site to Launch"; Medical Tribune; bearing a date of 1999; printed on Apr. 25, 2011; pp. 1-3; 40(21):3; located at http://www.mol.net/media/medscape-trib-/Bid-For-Surgery_Web_Site_To_Launch.htm.
"Internet Archive Wayback Machine"; bearing a date of Feb. 20, 2008; created on Jul. 9, 2015; 1 pg.; located at www.zocdoc.com.
"Quantitative Aspects of Clinical Decision Making Part 2"; bearing a date of Jun. 10, 2006; printed on Jul. 10, 2015; pp. 1-10; located at: www.what-when-how.com.
"Quantitative Aspects of Clinical Decision Making Part 3"; bearing a date of Jun. 10, 2006; printed on Jul. 10, 2015; pp. 1-5; located at: www.what-when-how.com.

\* cited by examiner

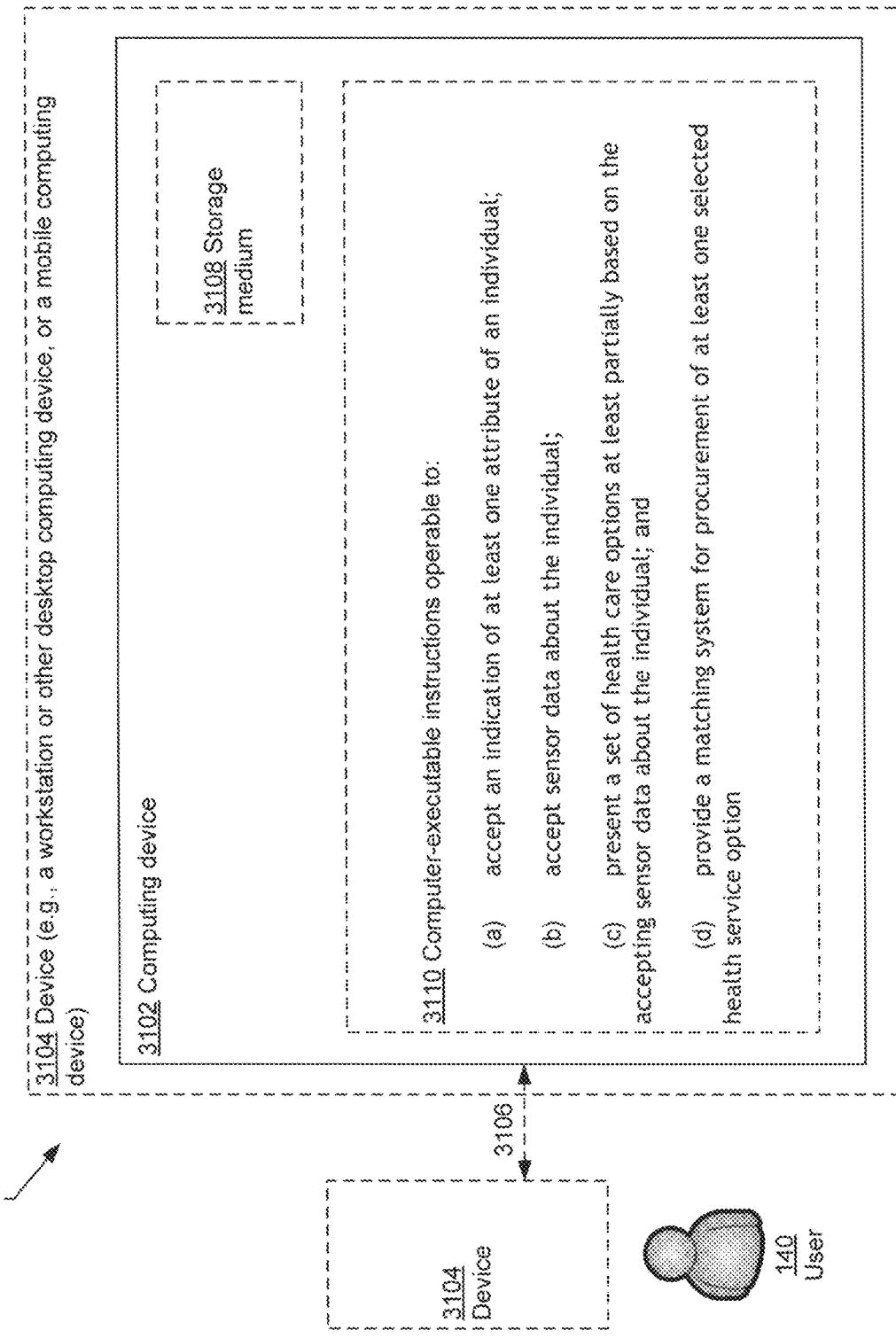

COMPUTATIONAL SYSTEMS AND METHODS FOR HEALTH SERVICES PLANNING AND MATCHING

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 12/381,377, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 10 Mar. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/381,680, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 12 Mar. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/587,239, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 2 Oct. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/587,313, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 5 Oct. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/589,124, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 16 Oct. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/589,171, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 19 Oct. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/589,639, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 26 Oct. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/589,728, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 27 Oct. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,104, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 2 Nov. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,163, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 3 Nov. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,250, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 4 Nov. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,335, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 5 Nov. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,439, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 24 Nov. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,541, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 25 Nov. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,768, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 2 Dec. 2009 now U.S. Pat. No. 8,095,384 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,859, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 3 Dec. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/655,474, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 30 Dec. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/655,580, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 31 Dec. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/657,429, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 20 Jan. 2010 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/657,498, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 21 Jan. 2010 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/657,980, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 29 Jan. 2010 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/658,056, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 1 Feb. 2010 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/658,166, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 3 Feb. 2010 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/658,256, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 4 Feb. 2010 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/660,029, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 18 Feb. 2010 now abandoned which is currently co-pending, or is an application of which a currently co-pending application is entitled to the benefit of the filing date.

The U.S. Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

This description relates to data capture and data handling techniques.

SUMMARY

In one aspect, a method includes but is not limited to accepting an indication of at least one attribute of an individual, accepting sensor data about the individual, presenting a set of health care options at least partially based on the accepting sensor data about the individual, and providing a matching system for procurement of at least one selected health service option. In addition to the foregoing, other apparatus aspects are described in the claims, drawings, and text forming a part of the present disclosure.

In one or more various aspects, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer.

In one aspect, a system includes but is not limited to means for accepting an indication of at least one attribute of an individual, means for accepting sensor data about the individual, means for presenting a set of health care options at least partially based on the accepting sensor data about the individual, and means for providing a matching system for procurement of at least one selected health service option. In addition to the foregoing, other apparatus aspects are described in the claims, drawings, and text forming a part of the present disclosure.

In one aspect, a system includes but is not limited to circuitry for accepting an indication of at least one attribute of an individual, circuitry for accepting sensor data about the individual, circuitry for presenting a set of health care options at least partially based on the accepting sensor data about the individual, and circuitry for providing a matching system for procurement of at least one selected health service option. In addition to the foregoing, other apparatus aspects are described in the claims, drawings, and text forming a part of the present disclosure.

In one aspect, a computer program product includes but is not limited to a signal-bearing medium bearing one or more instructions for accepting an indication of at least one attribute of an individual, one or more instructions for accepting sensor data about the individual, one or more instructions for presenting a set of health care options at least partially based on the accepting sensor data about the individual, and one or more instructions for providing a matching system for procurement of at least one selected health service option. In addition to the foregoing, other method aspects are described in the claims, drawings, and text forming a part of the present disclosure.

In one aspect, a system includes but is not limited to a computing device and instructions that when executed on the computing device cause the computing device to accept an indication of at least one attribute of an individual, accept sensor data about the individual, present a set of health care options at least partially based on the accepting sensor data about the individual, and provide a matching system for procurement of at least one selected health service option. In addition to the foregoing, other method aspects are described in the claims, drawings, and text forming a part of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIG. 31 illustrates an example device in which embodiments may be implemented related to health services planning and matching, which may serve as a context for introducing one or more processes and/or devices described herein.

DETAILED DESCRIPTION

Figure 1:
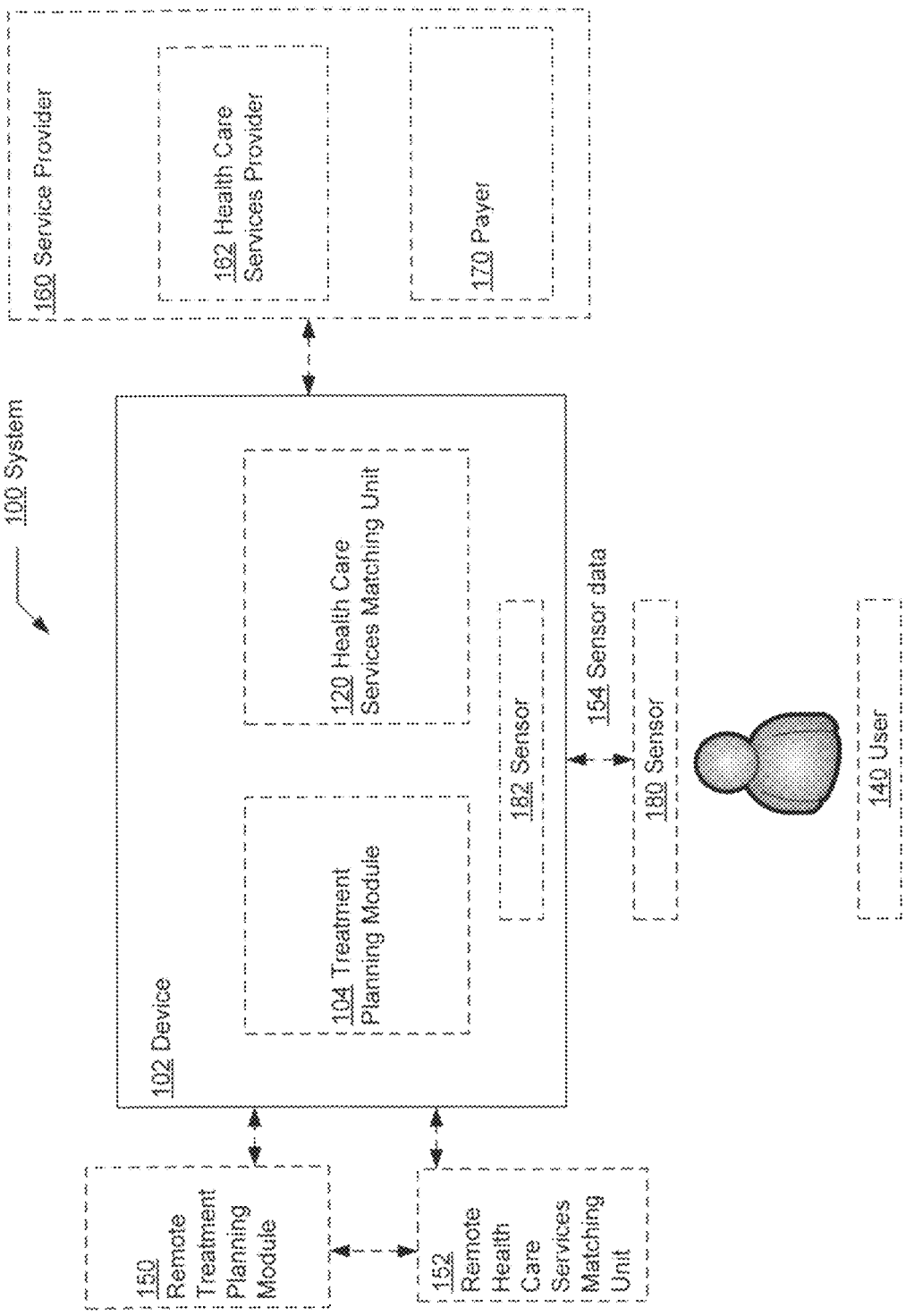
FIG. 1 illustrates an example of a health services planning and matching system in which embodiments may be implemented, perhaps in a device and/or through a network, which may serve as a context for introducing one or more processes and/or devices described herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates an example system 100 in which embodiments may be implemented. The system 100 includes a device 102. The device 102 may contain, for example, sensor 104, and treatment planning module 104. The device 102 may communicate over a network or directly with remote treatment planning module 150 and/or remote health care services matching unit 152. User 140 may interact directly or through a user interface with device 102. Device 102 may communicate with service provider 160, which may include health care services provider 162 and/or payer 170. Device 102 may accept sensor data 154 from sensor 180 proximal to a user 140 or from remote sensor 182 to provide a plurality of health services options, for example via treatment planning module 104. Device 102 may match a selected health service option with an appropriate service provider via, for example health care services matching unit 120. Service provider 160 may include, for example, health care services provider 162 and/or payer 170.

In FIG. 1, health care services matching unit 120 may solicit a health care services option from a service provider 160. Such a solicitation may include an invitation to bid in an auction, a reverse auction, or the like. Results of such a solicitation may include matching a doctor capable of providing a chosen health care services option with the user 140 in need of the chosen health care services option, perhaps according to one or more preferences provided by the user 140. Health care services matching unit 120 may otherwise find a service provider 160 through the use of a directory or other listing of health services providers.

In FIG. 1, the device 102 is illustrated as possibly being included within a system 100. Of course, virtually any kind of computing device may be used to implement the special purpose sensor 180 and/or special purpose sensor 182, special purpose treatment planning module 104 and/or special purpose health care services matching unit 120, such as, for example, a programmed workstation, a programmed desktop computer, a programmed networked computer, a programmed server, a collection of programmed servers and/or databases, a programmed virtual machine running inside a computing device, a programmed mobile computing device, or a programmed tablet PC.

Additionally, not all of the sensor 182, sensor 180, treatment planning module 104 and/or health care services matching unit 120 need be implemented on a single computing device. For example, the sensor 182, treatment planning module 104, and/or health care services matching unit 120 may be implemented and/or operable on a remote computer, while a user interface and/or local instance of the sensor 180, treatment planning module 104, and/or health care services matching unit 120 are implemented and/or occur on a local computer. Further, aspects of the sensors 180 and 182, treatment planning module 104, and/or health care services matching unit 120 may be implemented in different combinations and implementations than that shown in FIG. 1. For example, functionality of a user interface may be incorporated into the sensor 180, treatment planning module 104, and/or health care services matching unit 120. The sensor 180, sensor 182, treatment planning module 104, and/or health care services matching unit 120 may perform simple data relay functions and/or complex data analysis, including, for example, fuzzy logic and/or traditional logic steps. Further, many methods of searching health care and/or service provider databases known in the art may be used, including, for example, unsupervised pattern discovery methods, coincidence detection methods, and/or entity relationship modeling. In some embodiments, the sensor 180, sensor 182, treatment planning module 104, and/or health care services matching unit 120 may process user input data according to health care options and/or service provider information available as updates through a network.

Treatment planning module 104 and/or health care services matching unit 120 may access data stored in virtually any type of memory that is able to store and/or provide access to information in, for example, a one-to-many, many-to-one, and/or many-to-many relationship. Such a memory may include, for example, a relational database and/or an object-oriented database, examples of which are provided in more detail herein.

Figure 2:
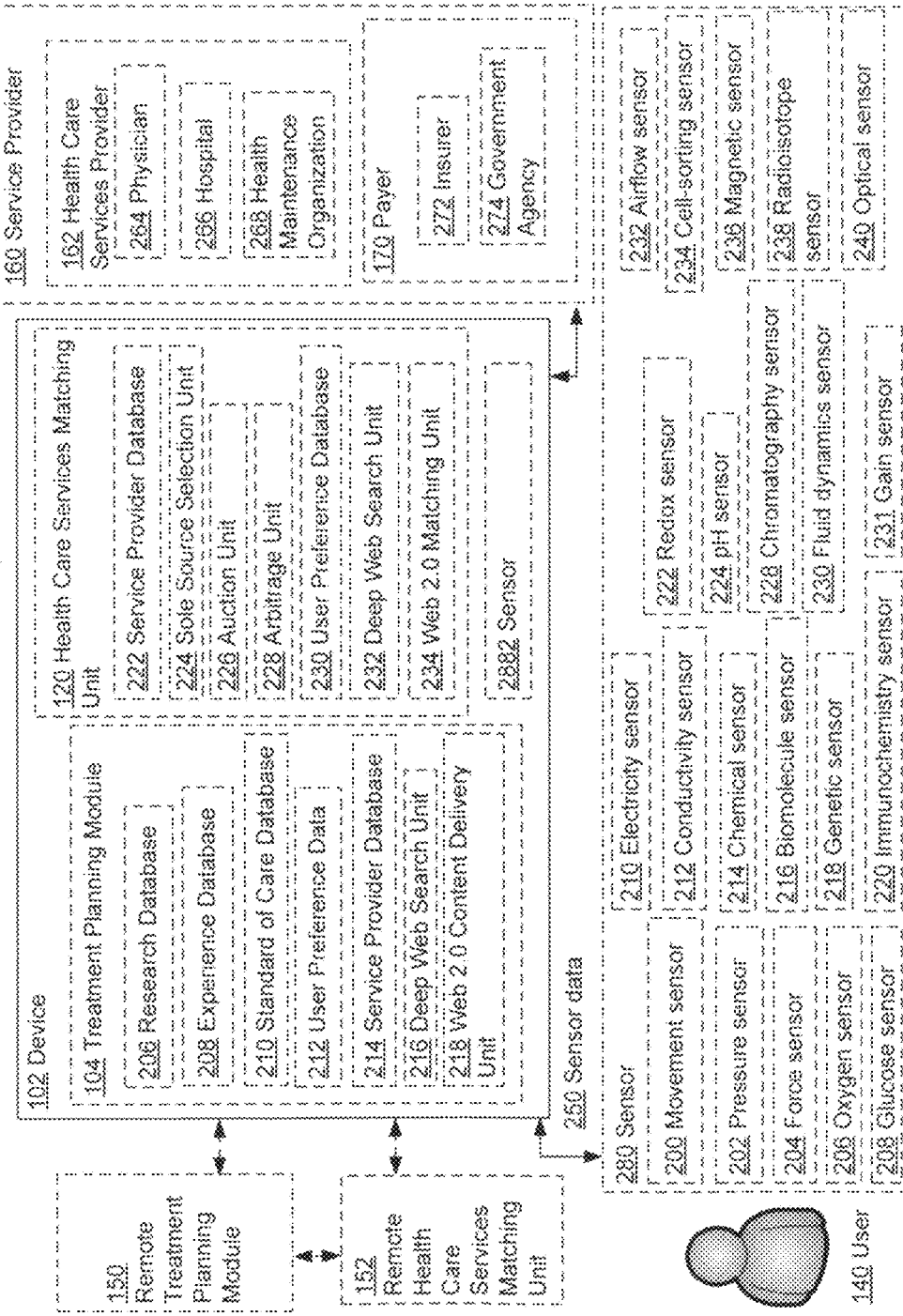
FIG. 2 illustrates certain alternative embodiments of the health services planning and matching system of FIG. 1.

FIG. 2 illustrates certain alternative embodiments of the system 100 of FIG. 1. In FIG. 2, the user 140 may interact with treatment planning module 104 and/or health care services matching unit 120 operable on the device 102. Sensor 280 may acquire sensor data 250 via movement sensor 200, pressure sensor 202, force sensor 204, oxygen sensor 206, glucose sensor 208, electricity sensor 210, conductivity sensor 212, chemical sensor 214, biomolecule sensor 216, genetic sensor 218, immunochemistry sensor 220, redox sensor 222, pH sensor 224, chromoatography sensor 228, fluid dynamics sensor 230, gain sensor 231, airflow sensor 232, cell-sorting sensor 234, magnetic sensor 236, radioisotope sensor 238, and/or optical sensor 240.

Alternatively, remote sensor 282 may generate sensor data from signals received from a distance. Examples of such remote sensing include the use of signal processing algorithms for a wireless sensor that can classify different types of motion and closely monitor a person's breathing and/or heart rate. For example, this type of sensor is useful in monitoring premature babies in a neonatal intensive care unit. Premature infants have very sensitive and fragile skin, which can make it difficult to directly attach sensors to them. A remote sensor can wirelessly monitor an infant's movements, including breathing and heart rate. Similarly, the sensor can be installed in a home for elder care or other outpatient monitoring. See also U.S. Pat. No. 6,315,719; U.S. Pat. No. 7,387,607; and U.S. Pat. No. 7,424,409; each of which is incorporated herein by reference.

Sensor data 250 may be accepted by treatment planning module 104 implemented on the device 102. The device 102 can communicate over a network with remote treatment planning module 150 and/or remote health care services matching unit 152. Treatment planning module 104 may include, for example, research database 206, experience database 208, standard of care database 210, user preference data 212, service provider database 214, Deep Web search unit 216, and/or Web 2.0 content delivery unit 218. The treatment planning module 104 may access and send health-related services options 242 to user 140. User 140 may subsequently choose and send health-related services selection 244 including a desired health service option from among a plurality of health services options to device 102 including health care services matching unit 120. Health care services matching unit 120 may include, for example, service provider database 222, sole source selection unit 224, auction unit 226, 228 arbitrage unit 228, user preference database 230, Deep Web search unit 232, and/or Web 2.0 matching unit 234. Health care services matching unit 120 may communicate directly or over a network with service provider 160 to obtain a suitable health-related service according to health-related services selection 244 and any user preference contained, for example, in user preference database 230. Service provider 160 may include health care services provider 162 and/or payer 170. Health care services provider 162 may include, for example, physician 264, hospital 266, and/or health maintenance organization 268. Payer 170 may include, for example, insurer 272, and/or government agency 274. Health care services matching unit 120 may then present matched health-related service 246 to user 140.

In this way, the user 140, who may be using a mobile device that is connected through a network with the system 100 and/or device 102 (e.g., in an office, outdoors and/or in a public environment), may generate a plurality of health service options as if the user 140 were interacting locally with the device 102 and/or system 100.

As referenced herein, the treatment planning module 104 and/or health care services matching unit 120 may be used to perform various data querying and/or recall techniques with respect to sensor data 250 and/or a plurality of health service options, in order to obtain and/or present a plurality of health service options. For example, where the sensor data 250 is organized, keyed to, and/or otherwise accessible using one or more reference health-related status indicators such as symptom, disease, diagnosis, or the like, treatment planning module 104 and/or health care services matching unit 120 may employ various Boolean, statistical, and/or semi-boolean searching techniques to match sensor data 250 with one or more indications of health status and/or one or more relevant health-related services options. Similarly, for example, where user preference data is organized, keyed to, and/or otherwise accessible using one or more service provider 160 interest profiles, various Boolean, statistical, and/or semi-boolean searching techniques may be performed by health care services matching unit 120 to match a given health-related services selection 244 with a service provider 160 to present, for example, a matched health-related service 246.

Many examples of databases and database structures may be used in connection with the treatment planning module 104 and/or health care services matching unit 120. Such examples include hierarchical models (in which data is organized in a tree and/or parent-child node structure), network models (based on set theory, and in which multi-parent structures per child node are supported), or object/relational models (combining the relational model with the object-oriented model).

Still other examples include various types of eXtensible Mark-up Language (XML) databases. For example, a database may be included that holds data in some format other than XML, but that is associated with an XML interface for accessing the database using XML. As another example, a database may store XML data directly. Additionally, or alternatively, virtually any semi-structured database may be used, so that context may be provided to/associated with stored data elements (either encoded with the data elements, or encoded externally to the data elements), so that data storage and/or access may be facilitated.

Such databases, and/or other memory storage techniques, may be written and/or implemented using various programming or coding languages. For example, object-oriented database management systems may be written in programming languages such as, for example, C++ or Java. Relational and/or object/relational models may make use of database languages, such as, for example, the structured query language (SQL), which may be used, for example, for interactive queries for information and/or for gathering and/or compiling data from the relational database(s).

For example, SQL or SQL-like operations over one or more reference health attribute and/or reference service provider may be performed, or Boolean operations using a reference health attribute and/or reference service provider may be performed. For example, weighted Boolean operations may be performed in which different weights or priorities are assigned to one or more of the reference health-related status attributes and/or reference service providers, including reference health conditions and/or reference service providers associated with various reference health-related status attributes, perhaps relative to one another. For example, a number-weighted, exclusive-OR operation may be performed to request specific weightings of desired (or undesired) health reference data or service providers to be included or excluded. Reference health-related status attributes may include normal physiological values for such health-related things as pain, reaction time, body or eye movement, memory, alertness, blood pressure, or the like. Such normal physiological values may be "normal" relative to the user 140, to a subpopulation to which the user 140 belongs, or to a general population. Similarly, reference service providers may be associated with, for example, the general medical community, a medical specialty, a local geographical area or the like.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation used herein (e.g., beginning with a presentation of a flowchart presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Figure 3:
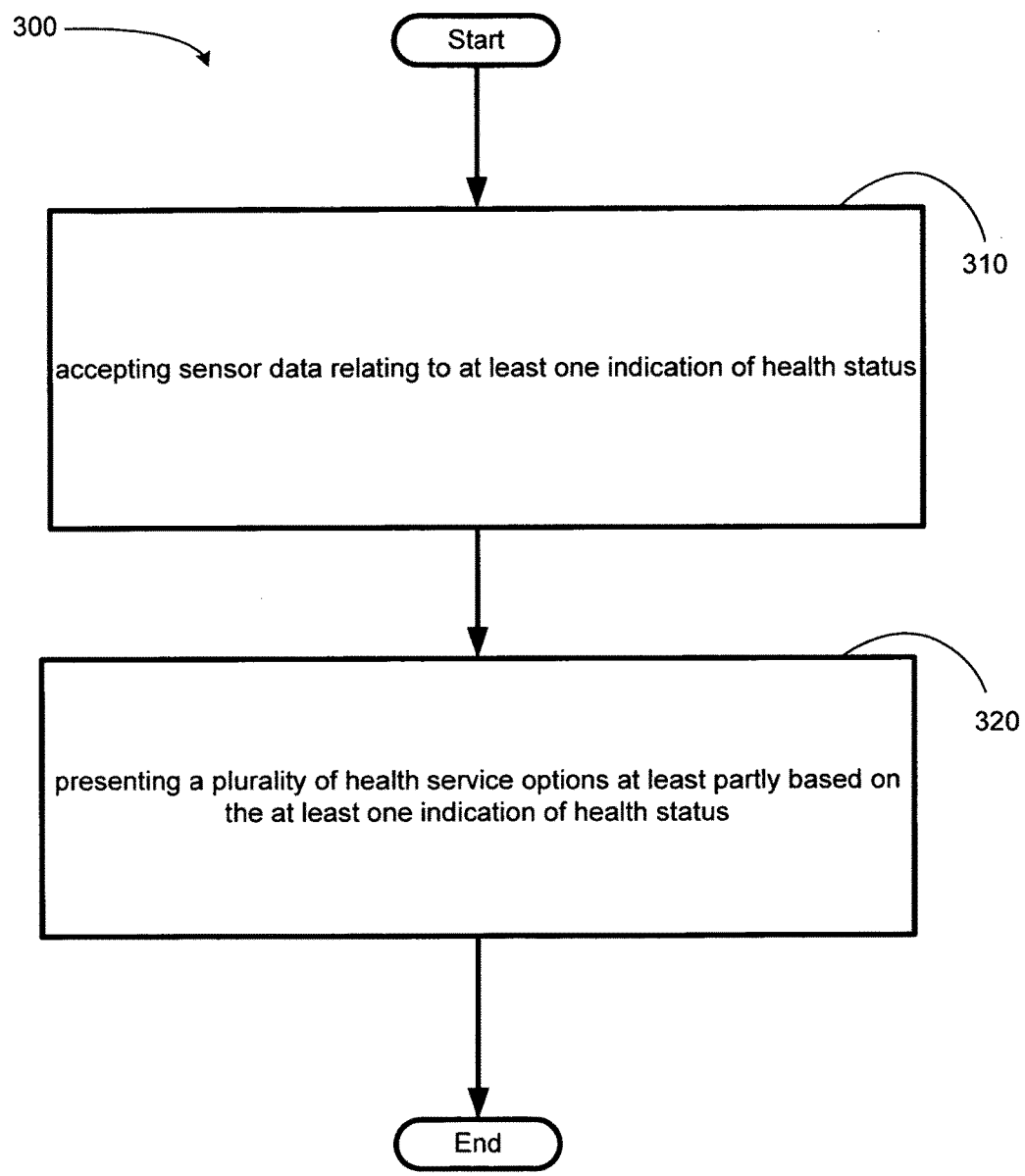
FIG. 3 illustrates an example of an operational flow representing example operations related to health services planning and matching, which may serve as a context for introducing one or more processes and/or devices described herein.

FIG. 3 illustrates an operational flow 300 representing example operations related to health services planning and matching. In FIG. 3 and in following figures that include various examples of operational flows, discussion and explanation may be provided with respect to the above-described system environments of FIGS. 1-2, and/or with respect to other examples and contexts. However, it should be understood that the operational flows may be executed in a number of other environments and contexts including that of FIGS. 17 and 18, and/or in modified versions of FIGS. 1-2. Also, although the various operational flows are presented in the sequences illustrated, it should be understood that the various operations may be performed in other orders than those which are illustrated, or may be performed concurrently.

After a start operation, operation 310 depicts accepting sensor data relating to at least one indication of health status. For example, treatment planning module 104 and/or device 102 may accept sensor data relating to at least one indication of health status. In one embodiment, sensor 280 may transmit sensor data 250 to device 102 relating to a symptom or disease. The user 140 may be a patient having a medical condition, an individual experiencing one or more symptoms, an asymptomatic individual, or the like. Sensor data relating to at least one indication of health status may also include indications for cosmetic enhancement, pregnancy, or improvement in athletic performance. In another embodiment, treatment planning module 104 accepting blood pressure sensor data indicating a sustained rise in blood pressure over time may present a plurality of health service options based on the indication of high blood pressure received from the blood pressure sensor. The user 140 may then analyze the plurality of health service options to determine whether or not to proceed in finding a health service provider for the presented options for addressing the detected high blood pressure. In one embodiment, user 140 may wish to find a health service provider to address one of a plurality of presented health service options. In this case, health care services matching unit 120 may provide, for example, an auction system by which user 140 can procure the desired health care service, for example, in a given geographic area at a competitive price.

Operation 320 depicts presenting a plurality of health service options at least partly based on the at least one indication of health status. For example, treatment planning module 104 and/or device 102 may present a plurality of health service options at least partly based on the at least one indication of health status. In one embodiment, treatment planning module 104 may, based on accepted sensor data, present a set of health service options according to one or more diagnoses or treatment paths corresponding to symptom(s) or conditions.

In one embodiment, a stochastic model can be built to describe an image, for example a medical image. The stochastic model may then be used to compare other images in the same way that it compares other data sequences. Such a system is useful in automatic screening of medical image data to identify features of interest. The system can be used to compare images of the same patient taken at different times, for example to monitor progress of a tumor, or it could be used to compare images taken from various patients with a standard image.

D. Nikovski, "Constructing Bayesian Networks for Medical Diagnosis from Incomplete and Partially Correct Statistics," IEEE Transactions on Knowledge and Data Engineering, Vol. 12:4, pp. 509-516 (2000). The paper discusses several knowledge engineering techniques for the construction of Bayesian networks for medical diagnostics when the available numerical probabilistic information is incomplete or partially correct. This situation occurs often when epidemiological studies publish only indirect statistics and when significant unmodeled conditional dependence exists in the problem domain. While nothing can replace precise and complete probabilistic information, still a useful diagnostic system can be built with imperfect data by introducing domain-dependent constraints. We propose a solution to the problem of determining the combined influences of several diseases on a single test result from specificity and sensitivity data for individual diseases. We also demonstrate two techniques for dealing with unmodeled conditional dependencies in a diagnostic network. These techniques are discussed in the context of an effort to design a portable device for cardiac diagnosis and monitoring from multimodal signals.

Figure 4:
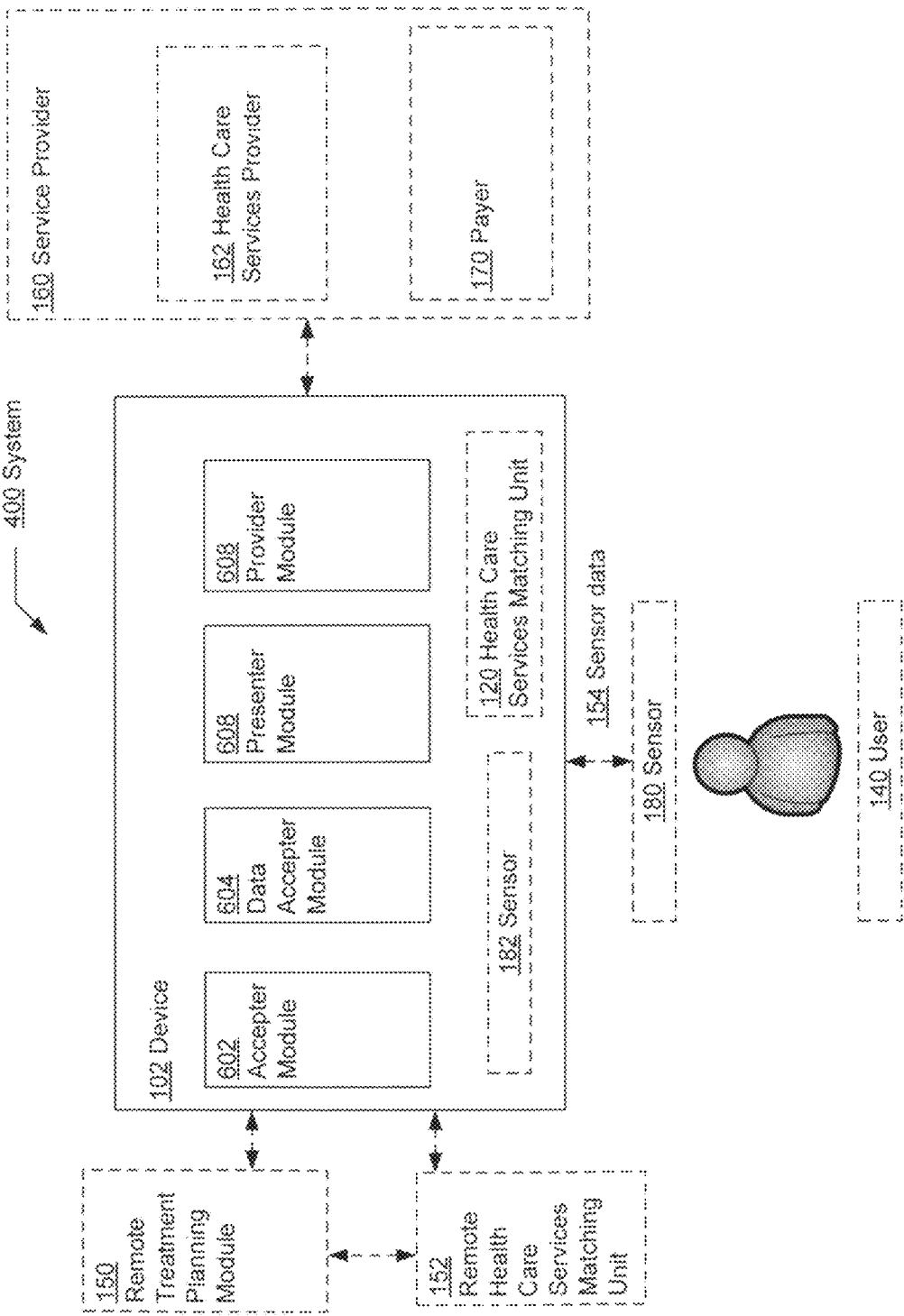
FIG. 4 illustrates an example of a health services planning and matching system in which embodiments may be implemented, perhaps in a device and/or through a network, which may serve as a context for introducing one or more processes and/or devices described herein.

FIG. 4 illustrates an example system 400 in which embodiments may be implemented. The system 400 includes a device 102. The device 102 may contain, for example, accepter module 602, data accepter module 604, presenter module 608, and/or provider module 610. The device 102 may communicate over a network or directly with remote treatment planning module 150 and/or remote health care services matching unit 152. User 140 may interact directly or through a user interface with device 102. Device 102 may communicate with service provider 160, which may include health care services provider 162 and/or payer 170. Device 102 may accept user input to provide one or more health services options, for example via accepter module 602, data accepter module 604, presenter module 608, and/or provider module 610. Device 102 may accept a selected health service option and match it with an appropriate service provider via, for example health care services matching unit 120. Service provider 160 may include, for example, health care services provider 162 and/or payer 170.

In FIG. 4, the device 102 is illustrated as possibly being included within a system 400. Of course, virtually any kind of computing device may be used to implement the special purpose health care services matching unit 120, special purpose accepter module 602, special purpose data accepter module 604, special purpose presenter module 608, and/or special purpose provider module 610, such as, for example, a workstation, a desktop computer, a networked computer, a server, a collection of servers and/or databases, a virtual machine running inside a computing device, a mobile computing device, or a tablet PC.

Additionally, not all of the health care services matching unit 120, accepter module 602, data accepter module 604, presenter module 608, and/or provider module 610 need be implemented on a single computing device. For example, health care services matching unit 120, accepter module 602, data accepter module 604, presenter module 608, and/or provider module 610 may be implemented and/or operable on a remote computer, while a user interface and/or local instance of the health care services matching unit 120, accepter module 602, data accepter module 604, presenter module 608, and/or provider module 610 are implemented and/or occur on a local computer. Further, aspects of health care services matching unit 120, accepter module 602, data accepter module 604, presenter module 608, and/or provider module 610 may be implemented in different combinations and implementations than that shown in FIG. 4. For example, functionality of a user interface may be incorporated into the health care services matching unit 120, accepter module 602, data accepter module 604, presenter module 608, and/or provider module 610. The health care services matching unit 120, accepter module 602, data accepter module 604, presenter module 608, and/or provider module 610 may perform simple data relay functions and/or complex data analysis, including, for example, fuzzy logic and/or traditional logic steps. Further, many methods of searching health care and/or service provider databases known in the art may be used, including, for example, unsupervised pattern discovery methods, coincidence detection methods, and/or entity relationship modeling. In some embodiments, health care services matching unit 120, accepter module 602, data accepter module 604, presenter module 608, and/or provider module 610 may process user input data according to health care options and/or service provider information available as updates through a network.

Health care services matching unit 120, accepter module 602, data accepter module 604, presenter module 608, and/or provider module 610 may access data stored in virtually any type of memory that is able to store and/or provide access to information in, for example, a one-to-many, many-to-one, and/or many-to-many relationship. Such a memory may include, for example, a relational database and/or an object-oriented database, examples of which are provided in more detail herein.

Figure 5:
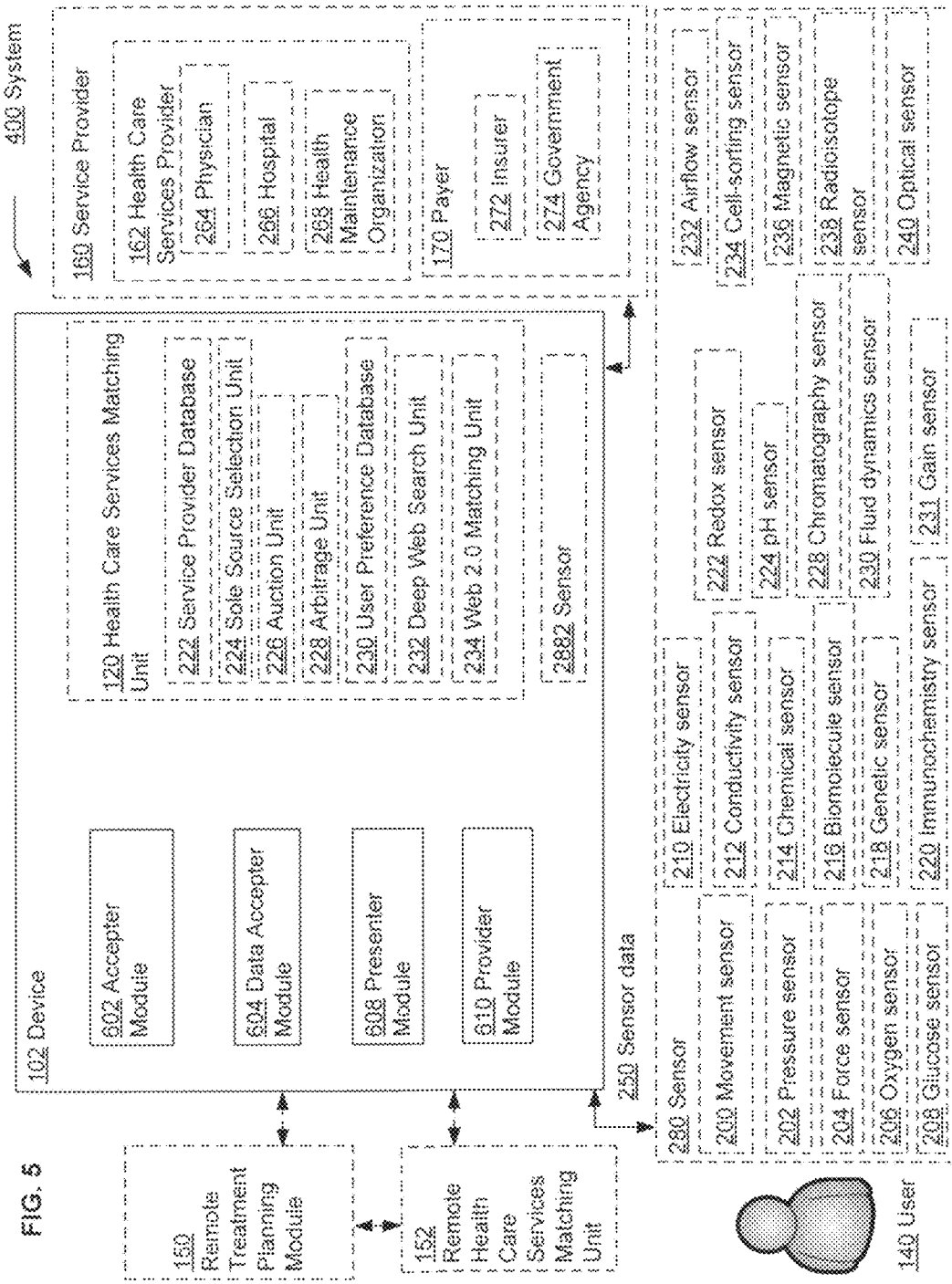
FIG. 5 illustrates certain alternative embodiments of the health services planning and matching system of FIG. 4.

FIG. 5 further illustrates system 400 including device 102, which may further include health care services matching module 120, sensor 2882, accepter module 602, data accepter module 604, presenter module 608, and/or provider module 610. Health care services matching module 120 may include service provider database 222, sole source selection unit 224, auction unit 226, arbitrage unit 228, user preference database 230, deep web search unit 232 and/or Web 2.0 matching unit 234. Device 102 may communicate with remote treatment planning module 150, remote health care services matching unit 152, and/or service provider 160. Service provider 160 may include health care services provider 162 and/or payer 170. Health care services provider 162 may include physician 264, hospital 266, and/or health maintenance organization 268. Payer 170 may include insurer 272 and/or government agency 274. Additionally, device 102 may accept sensor data 250 from and/or communicate with sensor 280. Sensor 280 may include movement sensor 200, pressure sensor 202, force sensor 204, oxygen sensor 206, glucose sensor 208, electricity sensor 210, conductivity sensor 212, chemical sensor 214, biomolecule sensor 216, genetic sensor 218, immunochemistry sensor 220, redox sensor 222, pH sensor 224, chromatography sensor 228, fluid dynamics sensor 230, gain sensor 231, airflow sensor 232, cell-sorting sensor 234, magnetic sensor 236, radioisotope sensor 238, and/or optical sensor 240.

Figure 6:
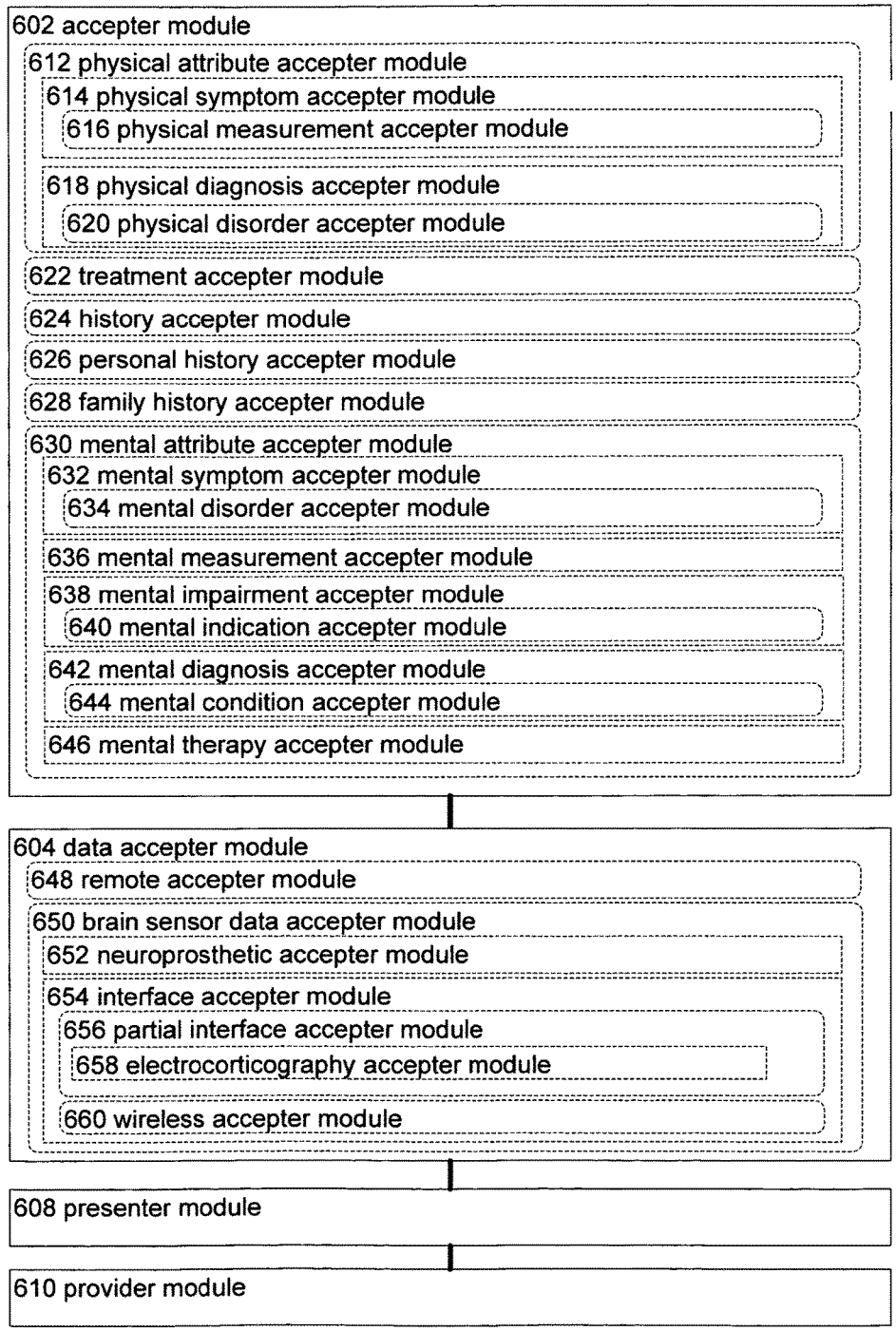
FIG. 6 illustrates certain alternative embodiments of the health services planning and matching system of FIG. 4.

FIG. 6 further illustrates system 400 including including accepter module 602, data accepter module 604, presenter module 608, and/or provider module 610. Accepter module 602 may include physical attribute accepter module 612, treatment accepter module 622, history accepter module 624, personal history accepter module 626, family history accepter module 628, and/or mental attribute accepter module 630. Physical attribute accepter module 612 may include physical symptom accepter module 614 and/or physical diagnosis accepter module 618. Physical symptom accepter module 614 may include physical measurement accepter module 616. Physical diagnosis accepter module 618 may include physical disorder accepter module 620. Mental attribute accepter module 630 may include mental symptom accepter module 632, mental measurement accepter module 636, mental impairment accepter module 638, mental diagnosis accepter module 642, and/or mental therapy accepter module 646. Mental symptom accepter module 632 may include mental disorder accepter module 634. Mental impairment accepter module 638 may include mental indication accepter module 640. Mental diagnosis accepter module 642 may include mental condition accepter module 644. Data accepter module 604 may include remote accepter module 648 and/or brain sensor data accepter module 650. Brain sensor data accepter module 650 may include neuroprosthetic accepter module 652 and/or interface accepter module 654. Interface accepter module 654 may include partial interface accepter module 656 and/or wireless accepter module 660. Partial interface accepter module 656 may include electrocorticography accepter module 658.

Figure 7:
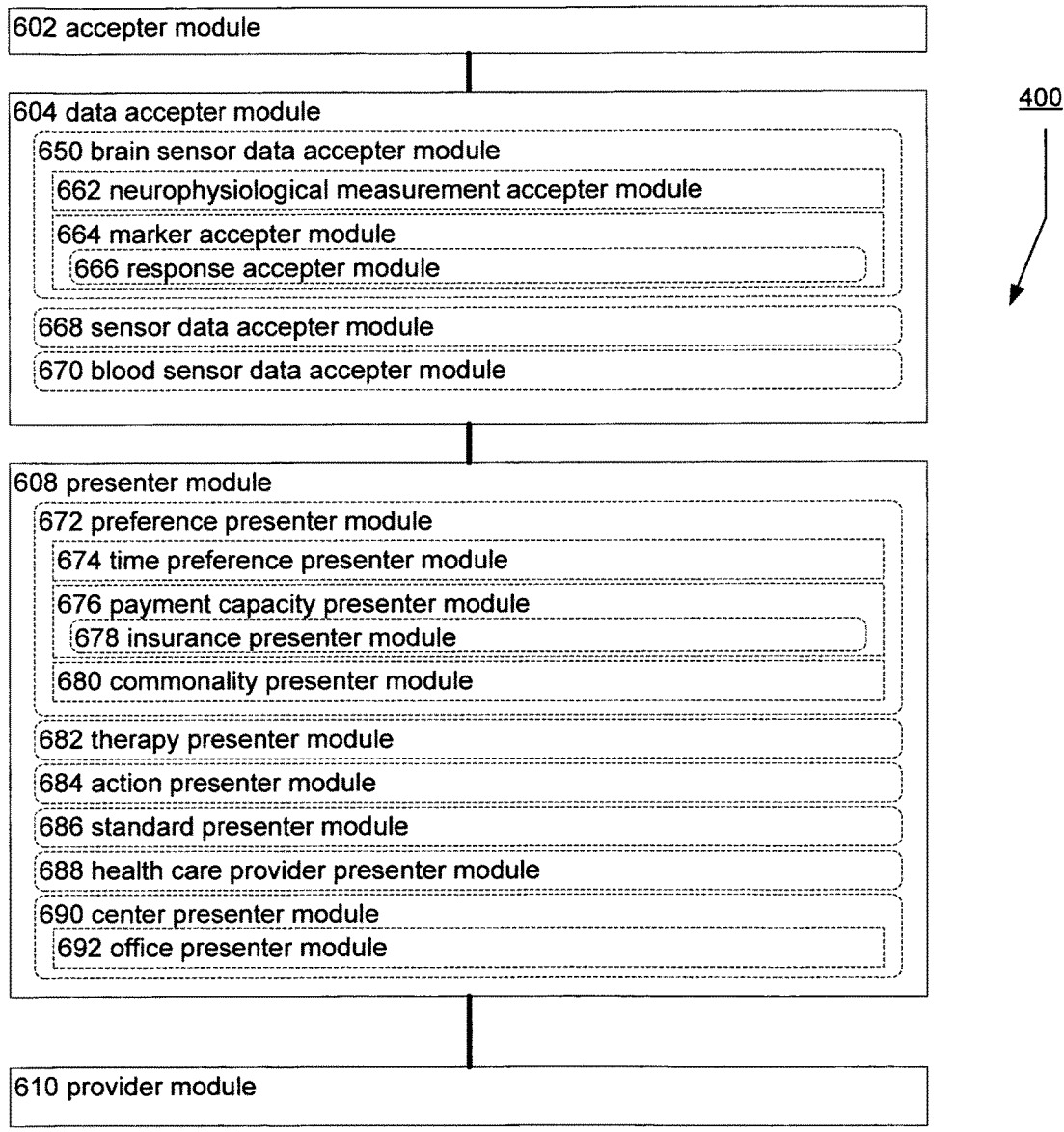
FIG. 7 illustrates certain alternative embodiments of the health services planning and matching system of FIG. 4.

FIG. 7 further illustrates system 400 including including accepter module 602, data accepter module 604, presenter module 608, and/or provider module 610. Data accepter module 604 may include brain sensor data accepter module 650, sensor data accepter module 668, and/or blood sensor data accepter module 670. Brain sensor data accepter module 650 may include neurophysiological measurement accepter module 662 and/or marker accepter module 664. Marker accepter module 664 may include response accepter module 666. Presenter module 608 may include preference presenter module 672, therapy presenter module 682, action presenter module 684, standard presenter module 686, health care provider presenter module 688, and/or center presenter module 690. Preference presenter module 672 may include time preference presenter module 674, payment capacity presenter module 676, and/or commonality presenter module 680. Payment capacity presenter module 676 may include insurance presenter module 678. Center presenter module 690 may include office presenter module 692.

Figure 8:
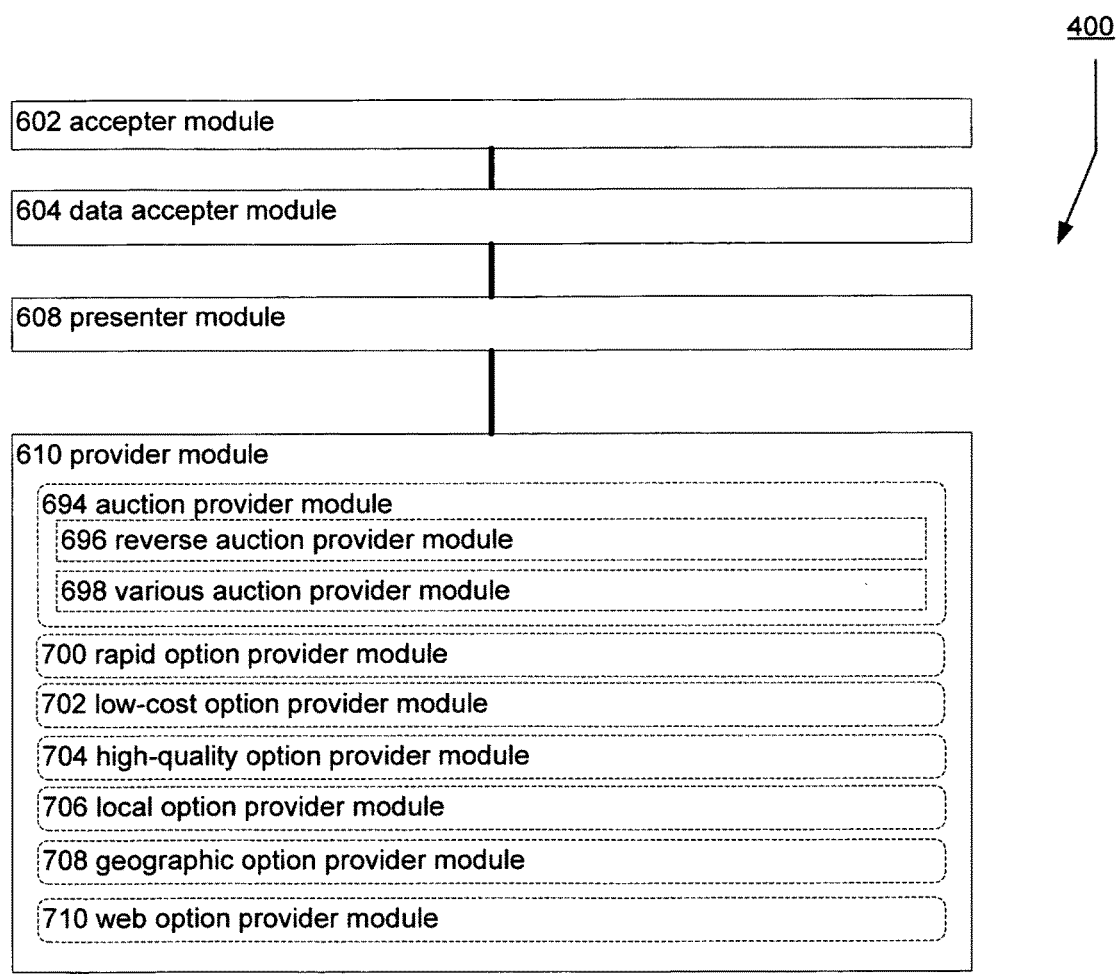
FIG. 8 illustrates certain alternative embodiments of the health services planning and matching system of FIG. 4.

FIG. 8 further illustrates system 400 including including accepter module 602, data accepter module 604, presenter module 608, and/or provider module 610. Provider module 610 may include auction provider module 694, rapid option provider module 700, low-cost option provider module 702, high-quality option provider module 704, local option provider module 706, geographic option provider module 708, and/or web option provider module 710. Auction provider module 694 may include reverse auction provider module 696 and/or various auction provider module 698.

Figure 9:
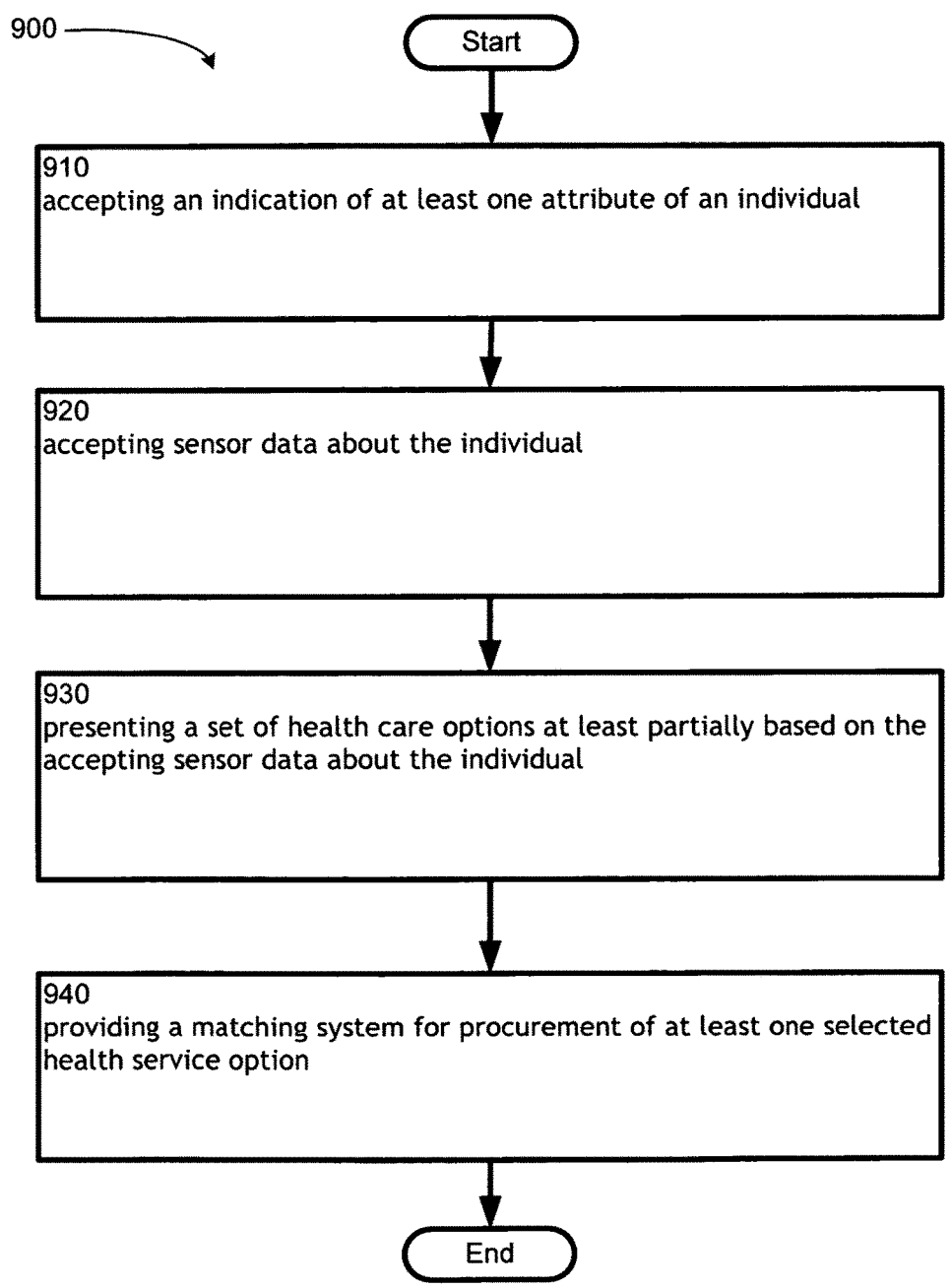
FIG. 9 illustrates an example of an operational flow representing example operations related to health services planning and matching, which may serve as a context for introducing one or more processes and/or devices described herein.

FIG. 9 illustrates an operational flow 900 representing example operations related to accepting an indication of at least one attribute of an individual, accepting sensor data about the individual, presenting a set of health care options at least partially based on the accepting sensor data about the individual, and providing a matching system for procurement of at least one selected health service option. In FIG. 9 and in following figures that include various examples of operational flows, discussion and explanation may be provided with respect to the above-described examples of FIGS. 4 through 8, and/or with respect to other examples and contexts. However, it should be understood that the operational flows may be executed in a number of other environments and contexts, and/or in modified versions of FIGS. 4 through 8. Also, although the various operational flows are presented in the sequence(s) illustrated, it should be understood that the various operations may be performed in other orders than those which are illustrated, or may be performed concurrently.

After a start operation, the operational flow 900 moves to operation 910. Operation 910 depicts accepting an indication of at least one attribute of an individual. For example, as shown in FIGS. 4 through 8, accepter module 602 can accept at least one attribute of an individual. In an embodiment, accepter module 602 may accept a personal medical history, for example, that includes an individual's history of epileptic episodes. Accepting at least one attribute of an individual may serve to better indicate an individual's medical status to a health care provider, for example. Some other examples of an attribute of an individual may include results from a patient interview, results from an individual's input into, for example, a computer station, and/or a medical history. In some instances, accepter module 602 may include a computer processor.

Then, operation 920 depicts accepting sensor data about the individual. For example, as shown in FIGS. 4 through 8, data accepter module 604 can accept sensor data about the individual. In an embodiment, data accepter module 604 may accept data from an array of epilepsy sensors. Accepting sensor data may serve to further validate or invalidate the accepted indication of an individual's attribute. Some examples of a sensor may include a movement sensor, a glucose sensor, an oxygen sensor, a chemical sensor, a thermometer, an optical sensor, and/or a biochip. In some instances, data accepter module 604 may include a computer processor.

Then, operation 930 depicts presenting a set of health care options at least partially based on the accepting sensor data about the individual. For example, as shown in FIGS. 4 through 8, presenter module 606 can present a set of health care options at least partially based on the accepting sensor data about the individual. In one embodiment, presenter module 606 may, based on at least one accepted attribute of an individual and accepted sensor data, present a set of health care options according to one or more diagnoses and/or treatment paths corresponding to symptom(s) or conditions indicated by the accepted attribute(s) of an individual and accepted sensor data. Some examples of presenting a set of health service options may include presenting at least one physician, medication, exercise, health care facility, and/or medical procedure. In an embodiment, presenter module 606 may present a list of physicians specializing in the treatment of epilepsy and a list of health care facilities that are able to accomodate the individual. In some instances, presenter module 606 may include a computer processor.

Then, operation 940 depicts providing a matching system for procurement of at least one selected health service option. For example, as shown in FIGS. 4 through 8, provider module 610 can provide a matching system for procurement of a desired health service option. For example, device 102, provider module 610, and/or health care services matching unit 120, upon accepting a selected health-related services option from user 140, may solicit bids from potential service providers 160. In the epilepsy example above, a user 140 may select a series of medication doses and a service provider that specializes in epilepsy treatment as the health care services option, for example. Based on this selection, health care services matching unit 120 may contact service provider(s) 160 to find capable and/or available service providers. In some embodiments, health care services matching unit 120 may limit contacts to those service providers 160 that satisfy a given user preference, such as geographic location, cost level, quality ranking, or the like. In some embodiments, service providers 160 may be invited to bid for a contract to provide a health care service, resulting in a low cost health care service for user 140. In some instances, provider module 610 may include a computer processor.

Figure 10:
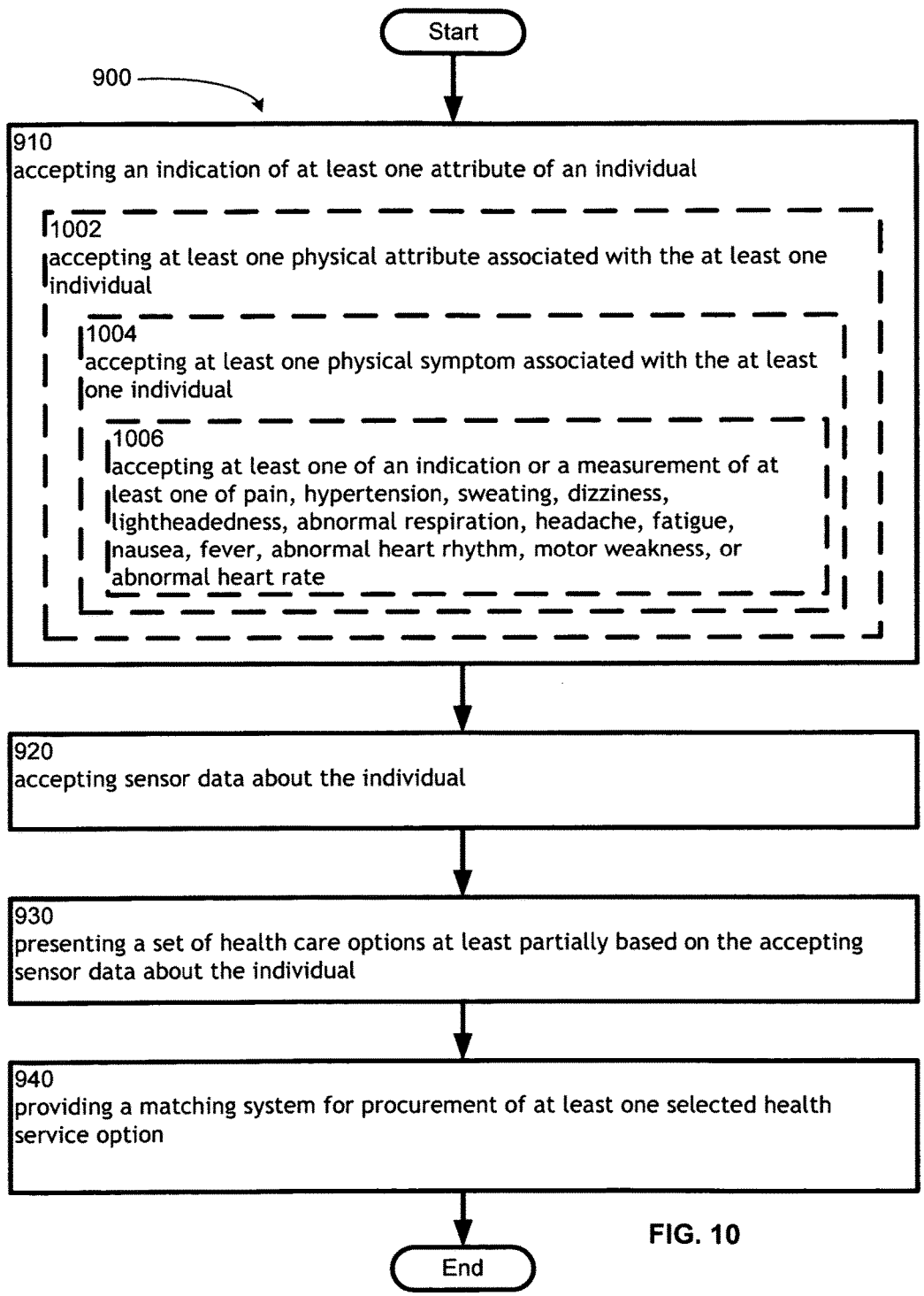
FIG. 10 illustrates an alternative embodiment of the operational flow of FIG. 9.

FIG. 10 illustrates alternative embodiments of the example operational flow 900 of FIG. 9. FIG. 10 illustrates example embodiments where operation 910 may include at least one additional operation. Additional operations may include operation 1002, operation 1004, and/or operation 1006.

Operation 1002 illustrates accepting at least one physical attribute associated with the at least one individual. For example, as shown in FIGS. 4 through 8, physical attribute accepter module 612 can accept at least one physical attribute associated with the at least one individual. In one instance, physical attribute accepter module 612 can accept a physical attribute associated with an individual, for example a weight history. A physical attribute may include an attribute that may be described and/or detected using senses, that has substance and/or a material existence, and/or that may be acted upon by physical force. Some examples of a physical attribute may include a biochemical measurement such as blood sugar level, an appearance, and/or a physiological measurement such as blood pressure, and/or skin conductivity. In some instances, physical attribute accepter module 612 may include a computer processor.

Further, operation 1004 illustrates accepting at least one physical symptom associated with the at least one individual. For example, as shown in FIGS. 4 through 8, physical symptom accepter module 614 can accept at least one physical symptom associated with the at least one individual. In one example, physical symptom accepter module 614 can accept from an individual and/or user interface a physical symptom, for example an indication of influenza (e.g., a fever). A physical symptom may include a manifestation, sign, and/or an indication of the presence of a disease and/or some other bodily disorder and/or abnormality. Some examples of a physical symptom may include pain, swelling, fever, rash, hypertension, a seizure, and/or discoloration. In some instances, physical symptom accepter module 614 may include a computer processor.

Further, operation 1006 illustrates accepting at least one of an indication or a measurement of at least one of pain, hypertension, sweating, dizziness, lightheadedness, abnormal respiration, headache, fatigue, nausea, fever, abnormal heart rhythm, motor weakness, or abnormal heart rate. For example, as shown in FIGS. 4 through 8, physical measurement accepter module 616 can accept at least one of an indication or a measurement of at least one of pain, hypertension, sweating, dizziness, lightheadedness, abnormal respiration, headache, fatigue, nausea, fever, abnormal heart rhythm, motor weakness, or abnormal heart rate. In one example, physical measurement accepter module 616 can accept an indication of an individual's pain and a measurement of high blood pressure from a patient interview. Pain may include a sensation of somatic hurt or disorder and may include acute pain and/or chronic pain. Hypertension may include chronically elevated blood pressure and may be considered to be present when a person's systolic blood pressure is consistently about 140 mm Hg or greater and/or their diastolic blood pressure is consistently about 90 mm Hg or greater. Sweating may include the excessive production and/or evaporation of fluid excreted by the sweat glands in the skin. Dizziness may include vertigo, disequilibrium, pre-syncope, and/or other balance disorders. Lightheadedness may include a sensation of dizziness and/or fainting. Abnormal respiration may include atypical and/or pathological breathing patterns. Headache may include pain in the head, neck, and/or upper back and may be a symptom of tension, migraine, dehydration, eye strain, sinus disorders, and/or low blood sugar. Fatigue may include muscle weakness and/or lack of strength. Nausea may include the sensation of unease and/or discomfort in the stomach, often with the urge to vomit. Fever may include an increase in internal body temperature to levels above normal. Abnormal heart rhythm may include inconsistent and/or irregular rhythmic contractions in the heart such as sick sinus syndrome, atrial fibrillation, and/or atrial flutter. Motor weakness may include a lack of strength and/or function in the portion of the central nervous system involved in movement.

An abnormal heart rate may include an irregular heart contraction frequency such as bradycardia, tachycardia or the like. In some instances, physical measurement accepter module 616 may include a computer processor.

Figure 11:
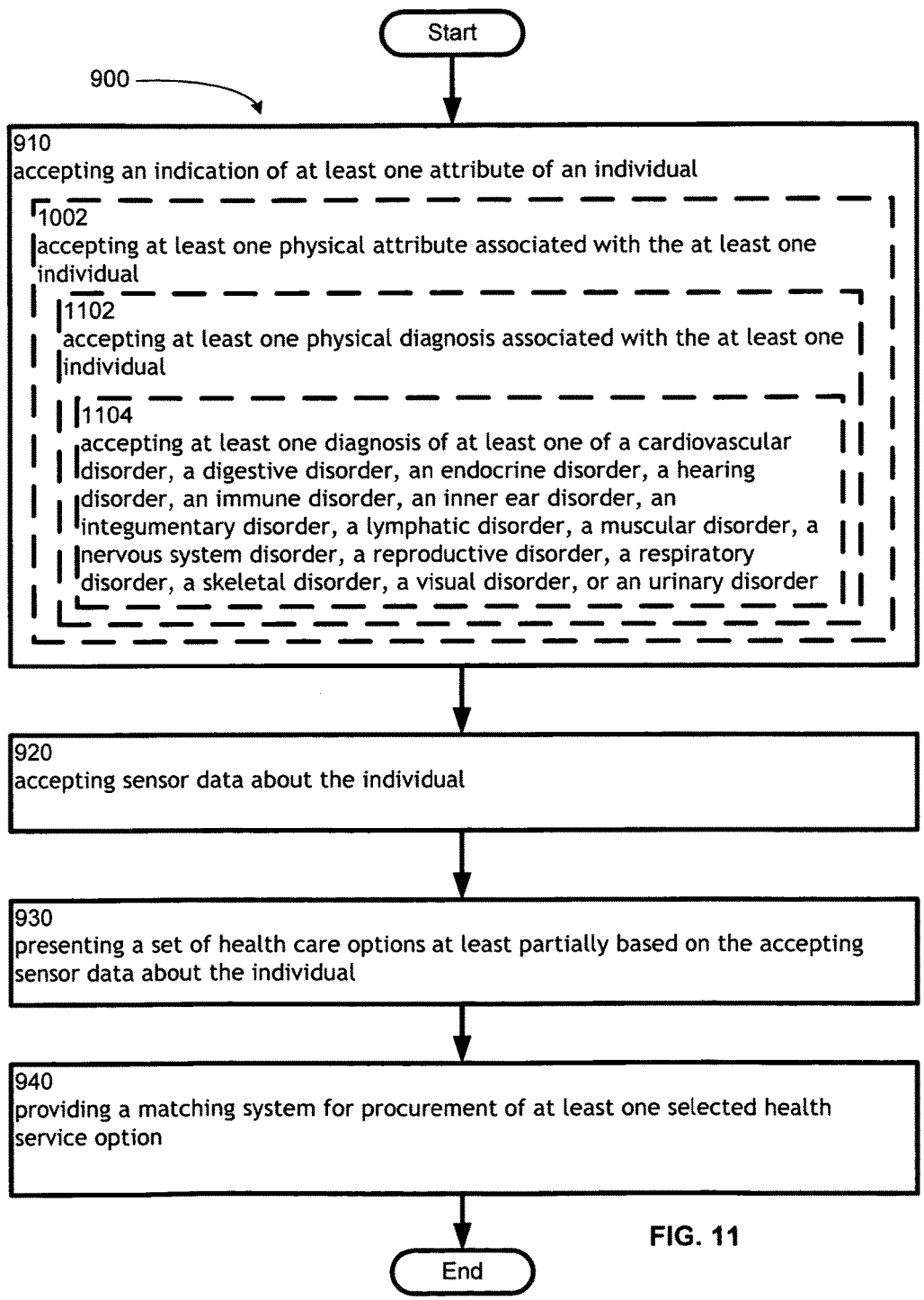
FIG. 11 illustrates an alternative embodiment of the operational flow of FIG. 9.

FIG. 11 illustrates alternative embodiments of the example operational flow 900 of FIG. 9. FIG. 11 illustrates example embodiments where operation 910 may include at least one additional operation. Additional operations may include operation 1102 and/or operation 1104.

Further, operation 1102 illustrates accepting at least one physical diagnosis associated with the at least one individual. For example, as shown in FIGS. 4 through 8, physical diagnosis accepter module 618 can accept at least one physical diagnosis associated with the at least one individual. In a specific example, physical diagnosis accepter module 618 may accept from a memory device a physical diagnosis of epilepsy associated with the individual. A physical diagnosis may include identifying a disease and/or condition by its outward signs and/or symptoms. Some other examples of a physical diagnosis may include identifying influenza and/or identifying Alzheimer's disease. In some instances, physical diagnosis accepter module 618 may include a computer processor.

Further, operation 1104 illustrates accepting at least one diagnosis of at least one of a cardiovascular disorder, a digestive disorder, an endocrine disorder, a hearing disorder, an immune disorder, an inner ear disorder, an integumentary disorder, a lymphatic disorder, a muscular disorder, a nervous system disorder, a reproductive disorder, a respiratory disorder, a skeletal disorder, a visual disorder, or an urinary disorder. For example, as shown in FIGS. 4 through 8, physical disorder module 620 can accept at least one diagnosis of at least one of a cardiovascular disorder, a digestive disorder, an endocrine disorder, a hearing disorder, an immune disorder, an inner ear disorder, an integumentary disorder, a lymphatic disorder, a muscular disorder, a nervous system disorder, a reproductive disorder, a respiratory disorder, a skeletal disorder, a visual disorder, or an urinary disorder. In a specific instance, physical disorder module 620 can accept from a user interface a diagnosis of a respiratory disorder. A cardiovascular disorder may include a disorder associated with the circulatory system including the pumping and channeling of blood to and from the body and lungs with the heart, the blood, and the blood vessels. Examples of a circulatory disorder include high blood pressure, coronary heart disease, atherosclerosis, or the like. A digestive disorder may include a disorder associated with the esophagus, the stomach, the liver, the gallbladder, the pancreas, the intestines, the rectum, the anus, and/or the digestive system including digestion and processing food with salivary glands. Examples of a digestive disorder include GERD, Crohn's disease, IBS, or the like. An endocrine disorder may include a disorder associated with the endocrine system including the pancreas, the pituitary gland, the pineal body and/or the pineal gland, the thyroid, the parathyroids, the adrenal glands, and/or communication within the body using hormones made by the endocrine glands, such as the hypothalamus. Examples of an endocrine disorder include diabetes, acromegaly, or the like. A hearing disorder may include a full or partial decrease in the ability to detect or understand sounds. Some examples of a hearing disorder may include otosclerosis, deafness, and/or unilateral hearing loss. An immune disorder may include a dysfunction of the immune system. Examples of an immune disorder may include an immunodeficiency, such as malfunctioning lymphocytes; autoimmunity, such as Coeliac disease and/or autoimmune hepatitis; and/or hypersensitivity, such as asthma. An inner ear disorder may include a balance disorder, such as vertigo, disequilibrium, and/or pre-syncope. An integumentary disorder may include a disorder associated with the integumentary system including the skin, hair, and/or nails, such as psoriasis, eczema, dermatitis, or the like. A lymphatic disorder may include a disorder associated with the lymphatic system including structures involved in the transfer of lymph between tissues and the blood stream and/or the lymph and the nodes and vessels that transport lymph including the immune system, including defending against disease-causing agents with leukocytes, and/or including the tonsils, the adenoids, the thymus, and/or the spleen. Examples of a lymphatic disorder include lymphedema, lymphadenopathy, or the like. A muscle disorder may include a disorder associated with the muscular system including the structure and/or movement of muscles. Examples of a muscle disorder include muscular dystrophy, myasthenia gravis, an injury, such as a strain, or the like. A nervous system disorder may include a disorder associated with the nervous system including collecting, transferring, and/or processing information with the brain, the spinal cord, the peripheral nerves, and/or the nerves. Examples of a nervous system disorder include multiple sclerosis, fibromyalgia, carpal tunnel syndrome, or the like. A reproductive disorder may include a disorder associated with the reproductive system including the sex organs, such as ovaries, fallopian tubes, the uterus, the vagina, mammary glands, testes, the vas deferens, seminal vesicles, the prostate, and/or the penis. Examples of a reproductive disorder include erectile dysfunction, endometriosis, fibroids, or the like. A respiratory disorder may include a disorder associated with the respiratory system including the organs used for breathing, the pharynx, the larynx, the trachea, the bronchi, the lungs, and/or the diaphragm. Examples of a respiratory disorder include emphysema, asthma, or the like. A skeletal disorder may include a disorder associated with the skeletal system including the structural support and protection with bones, cartilage, ligaments, and/or tendons. Examples of a skeletal disorder include osteoporosis, arthritis, tendonitis, a skeletal injury, such as a bone fracture, or the like. A visual disorder may include a disease, impairment, and/or lack of function in the eye and/or in visual perception. Some examples of a visual disorder may include amblyopia, macular degeneration, glaucoma, and/or blindness. A urinary disorder may include a disorder associated with the urinary system including the kidneys, the ureters, the bladder and/or urethra involved in fluid balance, electrolyte balance and/or the excretion of urine. Examples of a urinary disorder include bladder dysfunction, kidney disease, bladder or urethra infection, or the like. In some instances, physical disorder module 620 may include a computer processor.

Figure 12:
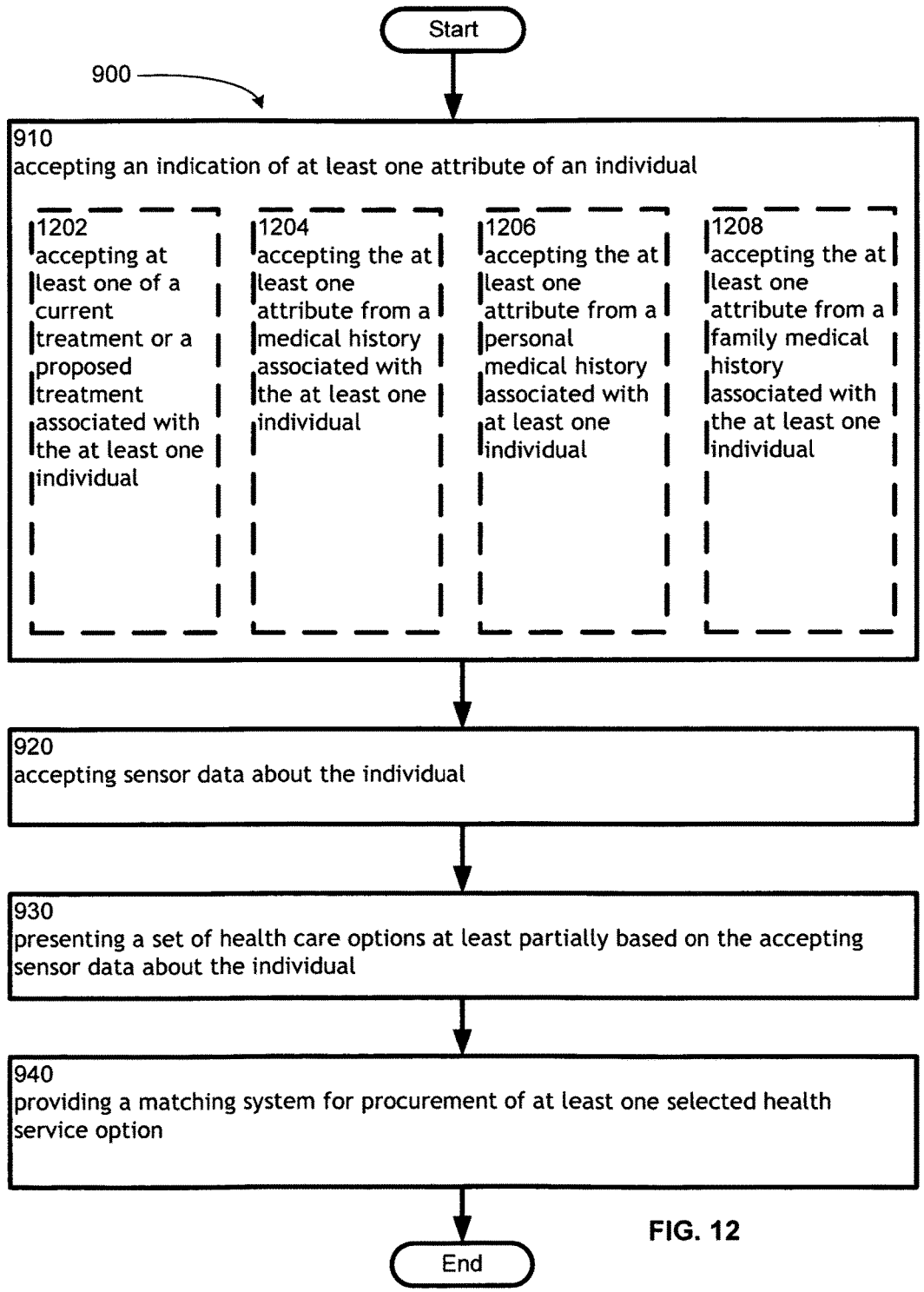
FIG. 12 illustrates an alternative embodiment of the operational flow of FIG. 9.

FIG. 12 illustrates alternative embodiments of the example operational flow 900 of FIG. 9. FIG. 12 illustrates example embodiments where operation 910 may include at least one additional operation. Additional operations may include operation 1202, operation 1204, operation 1206, and/or operation 1208.

Operation 1202 illustrates accepting at least one of a current treatment or a proposed treatment associated with the at least one individual. For example, as shown in FIGS. 4 through 8, treatment accepter module 622 can accept at least one of a current treatment or a proposed treatment associated with the at least one individual. In one instance, treatment accepter module 622 may accept a current treatment regime associated with a certain individual. A current treatment may include one or a series of treatments recommended, administered, and/or prescribed for a certain individual. A proposed treatment may include one or a series of treatments recommended, prescribed, and/or not currently administered to a certain individual. In some instances, treatment accepter module 622 may include a computer processor.

Operation 1204 illustrates accepting the at least one attribute from a medical history associated with the at least one individual. For example, as shown in FIGS. 4 through 8, history accepter module 624 can accept the at least one attribute from a medical history associated with the at least one individual. In one example, history accepter module 624 may accept an attribute from a medical history including a record of diabetes therapy associated with a specific individual. A medical history may include a list of previous illnesses, symptoms, medicines, treatments, health risk factors, operations, and/or doctor visits for an individual and/or a relation of an individual. In some instances, history accepter module 624 may include a computer processor.

Operation 1206 illustrates accepting the at least one attribute from a personal medical history associated with at least one individual. For example, as shown in FIGS. 4 through 8, personal history accepter module 626 can accept the at least one attribute from a personal medical history associated with at least one individual. In an emdodiment, personal history accepter module 626 may accept an attribute including, for example, a list of surgeries from a personal medical history associated with a specific individual. A personal medical history may include a list of previous illnesses, symptoms, medicines, treatments, health risk factors, operations, and/or doctor visits associated with at least one individual. A personal and/or a family medical history may include life history and/or social history characteristics such as smoking, drinking, drug use, sexual history, exercise history, eating history, nutraceutical history, or the like. In some instances, personal history accepter module 626 may include a computer processor.

Operation 1208 illustrates accepting the at least one attribute from a family medical history associated with the at least one individual. For example, as shown in FIGS. 4 through 8, family history accepter module 628 can accept the at least one attribute from a family medical history associated with the at least one individual. In an example, family history accepter module 628 may accept an attribute including a list of family members that have had epilepsy from a family medical history associated with a specific individual. A family medical history may include a list of previous illnesses, symptoms, medicines, treatments, health risk factors, operations, and/or doctor visits associated with family members related to the at least one individual. In some instances, family history accepter module 628 may include a computer processor.

Figure 13:
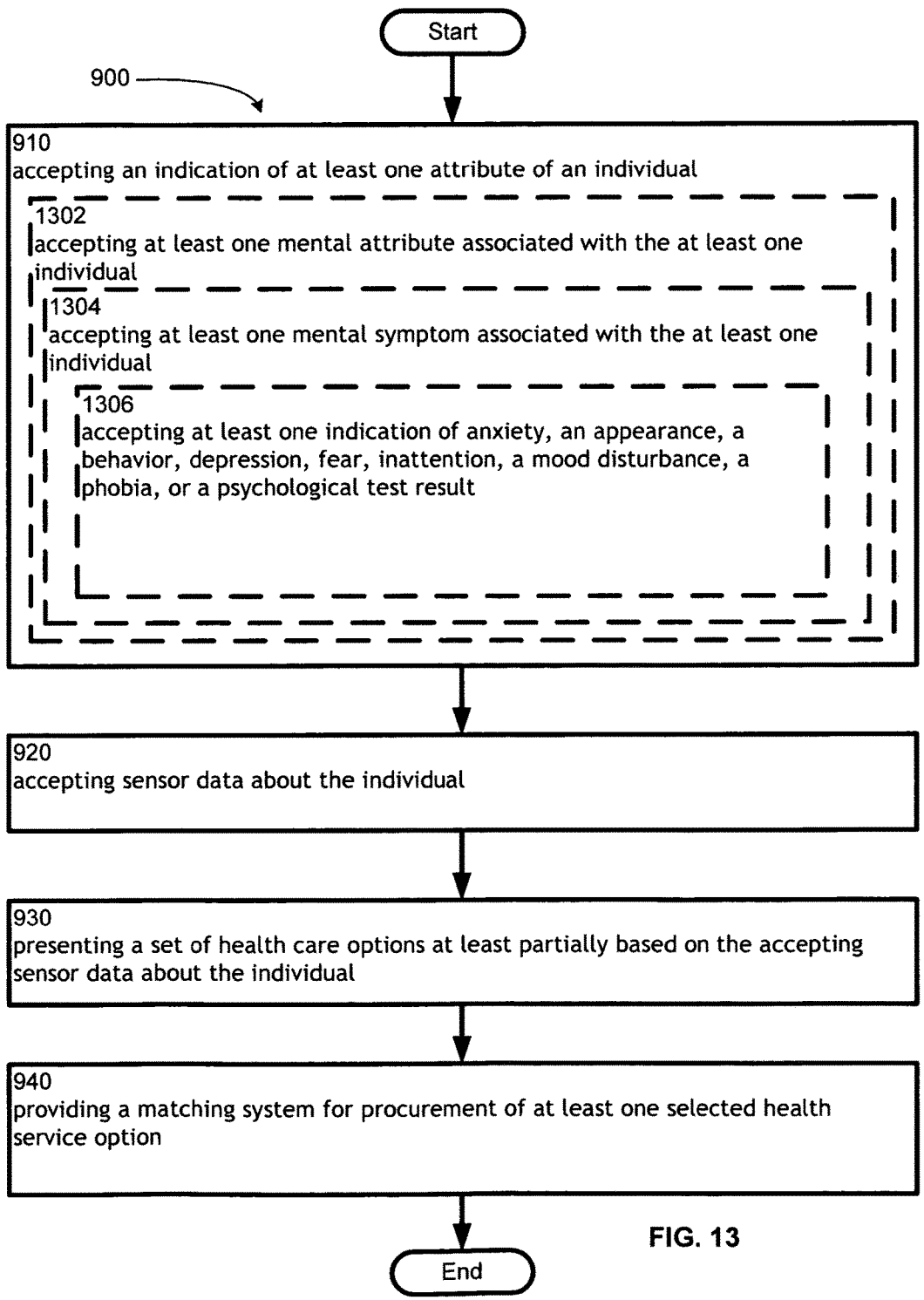
FIG. 13 illustrates an alternative embodiment of the operational flow of FIG. 9.

FIG. 13 illustrates alternative embodiments of the example operational flow 900 of FIG. 9. FIG. 13 illustrates example embodiments where operation 910 may include at least one additional operation. Additional operations may include operation 1302, operation 1304, and/or operation 1306.

Operation 1302 illustrates accepting at least one mental attribute associated with the at least one individual. For example, as shown in FIGS. 4 through 8, mental attribute accepter module 630 can accept at least one mental attribute associated with the at least one individual. In one example, mental attribute accepter module 630 may accept a mental attribute including, for example, an indication of a learning disability associated with a specific individual. A mental attribute may include an attribute that may be related to and/or associated with basic mental function and/or high-level brain function. Some examples of a mental attribute may include an indication of cognitive disability, measurements of brain activity, for example using functional MRI or near infra-red technology, and/or measurements of mental development. In some instances, mental attribute accepter module 630 may include a computer processor.

Further, operation 1304 illustrates accepting at least one mental symptom associated with the at least one individual. For example, as shown in FIGS. 4 through 8, mental symptom accepter module 632 can accept at least one mental symptom associated with the at least one individual. In one example, mental symptom accepter module 632 may accept a mental symptom including a stress level measurement associated with a specific individual. A mental symptom may include a manifestation, sign, and/or an indication of the presence of a disease and/or some other mental disorder and/or abnormality. Some examples of a mental symptom may include lack of attention, indication of stress, hyperactivity, nervousness, and/or lack of responsiveness. In some instances, mental symptom accepter module 632 may include a computer processor.

Further, operation 1306 illustrates accepting at least one indication of anxiety, an appearance, a behavior, depression, fear, inattention, a mood disturbance, a phobia, or a psychological test result. For example, as shown in FIGS. 4 through 8, mental disorder accepter module 634 can accept at least one indication of anxiety, an appearance, a behavior, depression, fear, inattention, a mood disturbance, a phobia, or a psychological test result. In one example, mental disorder accepter module 634 can accept from a user interface an indication of anxiety and depression. Anxiety may include feelings of fear, apprehension, and/or worry and may be accompanied by physical sensations. An appearance may include an outward, audible, and/or visible aspect of a person and/or thing associated with a person. A behavior may include the manner in which a person and/or thing associated with a person acts and/or reacts. Depression may include a mental state characterized by pessimism, a sense of inadequacy, despondence, despair, a low level of energy, and/or a lack of activity. Fear may be caused by impending danger, perceived evil, and/or pain, whether real or imagined. Inattention may include the failure of a person to focus attention. A mood disturbance may include a change in emotional state. A phobia may include an irrational, and/or persistent fear of certain situations, objects, activities, and/or people. A psychological test result may include a sample behavior for inferring a certain generalization about a person. For example, a personality test result may indicate that person has obsessive/compulsive characteristics. In some instances, mental disorder accepter module 634 may include a computer processor.

Figure 14:
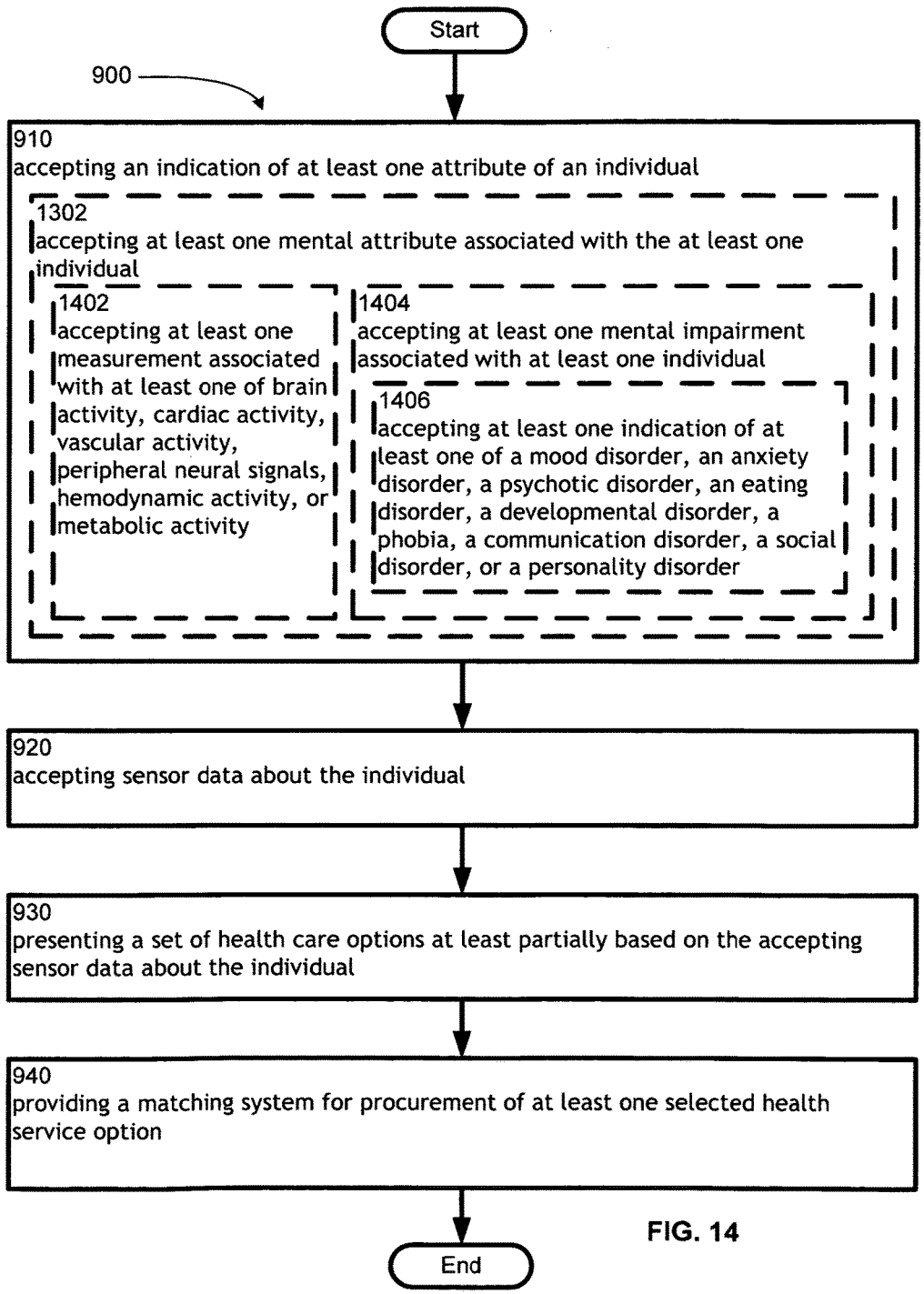
FIG. 14 illustrates an alternative embodiment of the operational flow of FIG. 9.

FIG. 14 illustrates alternative embodiments of the example operational flow 900 of FIG. 9. FIG. 14 illustrates example embodiments where operation 910 may include at least one additional operation. Additional operations may include operation 1402, operation 1404, and/or operation 1406.

Further, operation 1402 illustrates accepting at least one measurement associated with at least one of brain activity, cardiac activity, vascular activity, peripheral neural signals, hemodynamic activity, or metabolic activity. For example, as shown in FIGS. 4 through 8, mental measurement accepter module 636 can accept at least one measurement associated with at least one of brain activity, cardiac activity, vascular activity, peripheral neural signals, hemodynamic activity, or metabolic activity. In one instance, mental measurement accepter module 636 can accept a measurement associated with brain activity. Brain activity may include the electrical activity of the brain, such as that measured by EEG, MEG, or the like. Other brain activity measurements may include functional MRI imaging, near infra-red imaging, PET scanning, or the like. Cardiac activity may include electrical activity in the heart, such as that measured by EKG or visual imaging. Vascular activity may include any activity and/or function of the circulatory system. Peripheral neural signals may include neural signals sent through the peripheral nervous system. Hemodynamic activity may include any activity associated with the circulatory system. Metabolic activity may include any activity associated with the biochemical reactions occurring in a living organism. In some instances, mental measurement accepter module 636 may include a computer processor.

Further, operation 1404 illustrates accepting at least one mental impairment associated with at least one individual. For example, as shown in FIGS. 4 through 8, mental impairment accepter module 638 can accept at least one mental impairment associated with at least one individual. In one example, mental impairment accepter module 638 can accept a mental impairment associated with a specific individual, for example depression. A mental impairment may include a condition or function judged by a health care provider to be significantly impaired relative to the usual standard of an individual of their group, and may include mental impairment, sensory impairment, and/or mental disease. In some instances, mental impairment accepter module 638 may include a computer processor.

Further, operation 1406 illustrates accepting at least one indication of at least one of a mood disorder, an anxiety disorder, a psychotic disorder, an eating disorder, a developmental disorder, a phobia, a communication disorder, a social disorder, or a personality disorder. For example, as shown in FIGS. 4 through 8, mental indication accepter module 640 can accept at least one indication of at least one of a mood disorder, an anxiety disorder, a psychotic disorder, an eating disorder, a developmental disorder, a phobia, a communication disorder, a social disorder, or a personality disorder. In one instance, mental indication accepter module 640 can accept from a user interface an indication of a mood disorder in a specific individual. A mood disorder may include a condition whereby the prevailing emotional mood is distorted or inappropriate to the circumstances, and may include examples such as bipolar disorder, an alteration in mood, and/or depression. An anxiety disorder may include nervous system disorders such as irrationality, illogical worry not based on fact, fear, and/or phobia. A psychotic disorder may include a state of mind in which thinking becomes irrational and/or disturbed and may include hallucinations, abnormal perception, mania, dementia, delusions and/or delusional beliefs, delirium, depression, psychosis personality disorder, personality changes, and/or disorganized thinking. An eating disorder may include a compulsion to eat and/or avoid eating that negatively affects physical and/or mental health. Some examples of an eating disorder may include anorexia nervosa and bulimia nervosa. A developmental disorder may include a disorder occurring in a child's development, which may retard development. Some examples of a developmental disorder may include an emotional disorder, a cognitive disorder, and/or a mental disorder accompanied by physical traits, such as Down syndrome. A phobia may include an irrational, intense, and/or persistent fear of certain situations, objects, activities, and/or persons. Examples of phobias include social phobias, arachnophobia, xenophobia, and/or claustrophobia. A communication disorder may include a disease and/or a condition partially or totally preventing human communication. Some examples of a communication disorder may include autism, stuttering, and/or aphasia. A social disorder may include a condition characterized by a difficulty in human interaction and/or emotional discomfort in social situations. Some examples of a social disorder may include stage fright, social anxiety disorder, and/or shyness. A personality disorder may include a disorder characterized by pathological trends in personality structure. Some examples of a personality disorder may include a paranoid personality disorder, a narcissistic personality disorder, and/or an obsessive-compulsive personality disorder. In some instances, mental indication accepter module 640 may include a computer processor.

Figure 15:
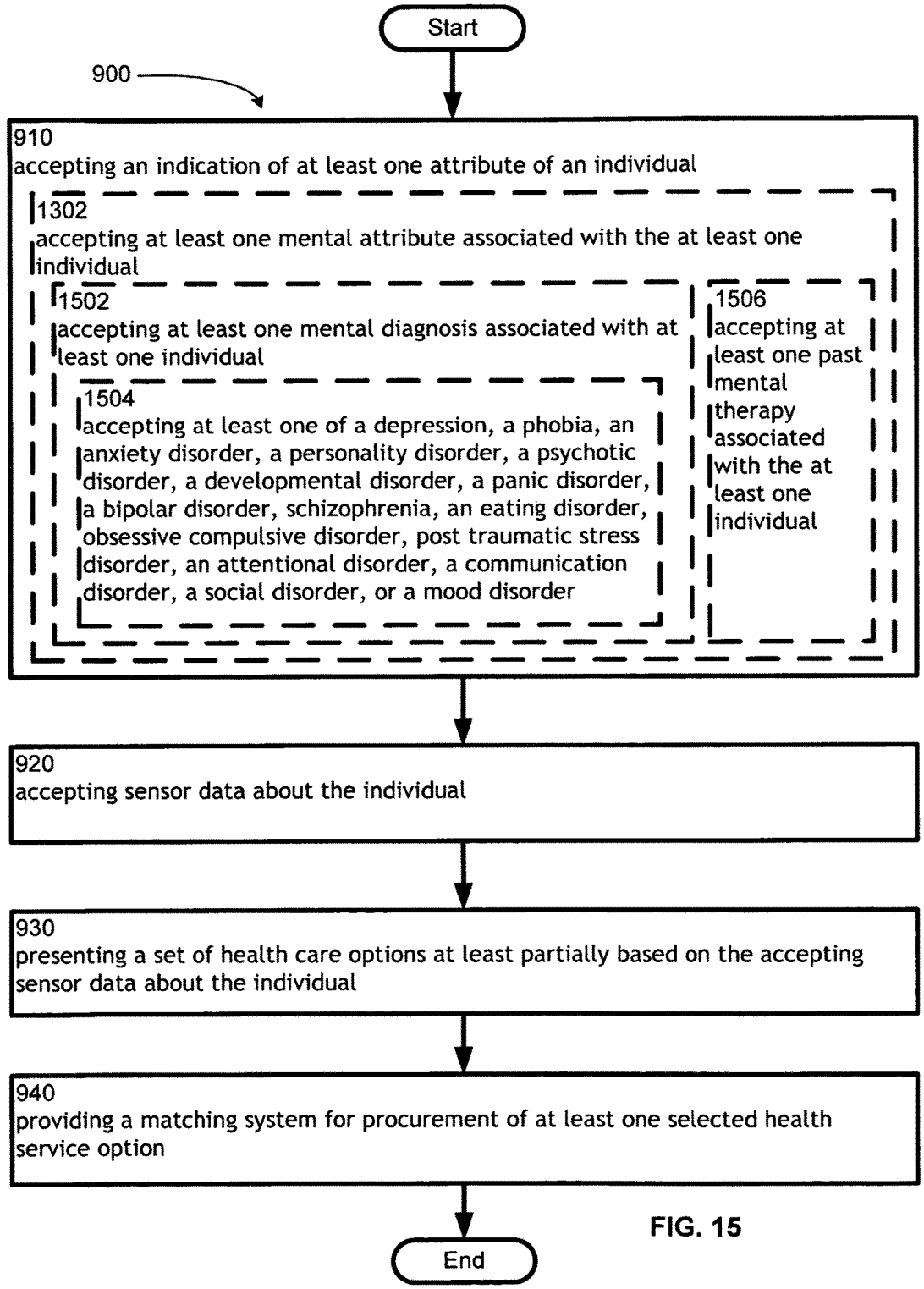
FIG. 15 illustrates an alternative embodiment of the operational flow of FIG. 9.

FIG. 15 illustrates alternative embodiments of the example operational flow 900 of FIG. 9. FIG. 15 illustrates example embodiments where operation 910 may include at least one additional operation. Additional operations may include operation 1502, operation 1504, and/or operation 1506.

Further, operation 1502 illustrates accepting at least one mental diagnosis associated with at least one individual. For example, as shown in FIGS. 4 through 8, mental diagnosis accepter module 642 can accept at least one mental diagnosis associated with at least one individual. In a specific instance, mental diagnosis accepter module 642 may accept a mental diagnosis such as a phobia associated with a specific individual. A mental diagnosis may include identifying a mental disorder and/or condition by its symptoms. Some examples of a mental diagnosis may include a mood disorder such as depression, an anxiety disorder such as PTSD, a behavioral disorder such as ADHD, a personality disorder such as borderline personality disorder, and/or a phobia. Mental disorders may include those listed in the Diagnostic and Statistical Manual of Mental Disorders (DSM). In some instances, mental diagnosis accepter module 642 may include a computer processor.

Further, operation 1504 illustrates accepting at least one of a depression, a phobia, an anxiety disorder, a personality disorder, a psychotic disorder, a developmental disorder, a panic disorder, a bipolar disorder, schizophrenia, an eating disorder, obsessive compulsive disorder, post traumatic stress disorder, an attentional disorder, a communication disorder, a social disorder, or a mood disorder. For example, as shown in FIGS. 4 through 8, mental condition accepter module 644 can accept at least one of a depression, a phobia, an anxiety disorder, a personality disorder, a psychotic disorder, a developmental disorder, a panic disorder, a bipolar disorder, schizophrenia, an eating disorder, obsessive compulsive disorder, post traumatic stress disorder, an attentional disorder, a communication disorder, a social disorder, or a mood disorder. In one example, mental condition accepter module 644 may accept a diagnosis of depression. Depression may include a mental state characterized by a pessimistic sense of inadequacy and/or a despondent lack of activity. A phobia may include an irrational, intense, and/or persistent fear of certain situations, objects, activities, and/or persons. Some phobias may include social phobias, arachnophobia, xenophobia, and/or claustrophobia. An anxiety disorder may include nervous system disorders such as irrationality, illogical worry not based on fact, fears, and/or phobias. A personality disorder may include a disorder characterized by pathological trends in personality structure. Some examples of a personality disorder may include a paranoid personality disorder, a narcissistic personality disorder, and/or an obsessive-compulsive personality disorder. A psychotic disorder may include a state of mind in which thinking becomes irrational and/or disturbed and may include hallucinations, delusional beliefs, personality changes, and/or disorganized thinking. A developmental disorder may include a disorder occurring in a child's development, which may often retard development. Some examples of a developmental disorder may include psychological or physical disorders. A panic disorder may include a condition characterized by recurring panic attacks in combination with significant behavioral change. A bipolar disorder may include a mood disorder characterized by the presence of one or more episodes of abnormally elevated mood, such as Bipolar I disorder, Bipolar II disorder, cyclothymia, and/or Bipolar-NOS. Schizophrenia may include a mental illness characterized by impairments in the perception or expression of reality, most commonly manifesting as auditory hallucinations, paranoid or bizarre delusions or disorganized speech and thinking in the context of significant social or occupational dysfunction. An eating disorder may include a compulsion to eat or avoid eating, such as anorexia nervosa and/or bulimia nervosa. Obsessive compulsive disorder may include a psychiatric anxiety disorder characterized by obsessive, distressing, intrusive thoughts and related compulsions which attempt to neutralize the obsessions. Post traumatic stress disorder may include an anxiety disorder that can develop after exposure to one or more terrifying events in which grave physical harm occurred or was threatened. An attentional disorder may include a persistent pattern of inattention and/or hyperactivity, as well as forgetfulness, poor impulse control or impulsivity, and distractibility, such as attention-deficit hyperactivity disorder (ADHD). A communication disorder may include a disease and/or a condition partially or totally preventing human communication. Some examples of a communication disorder may include autism, stuttering, and/or aphasia. A social disorder may include a condition characterized by a difficulty in human interaction and/or emotional discomfort in social situations. Some examples of a social disorder may include stage fright, social anxiety disorder, and/or shyness. A mood disorder may include a condition whereby the prevailing emotional mood is distorted or inappropriate to the circumstances and may include examples such as bipolar disorder and/or depression. In some instances, mental condition accepter module 644 may include a computer processor.

Further, operation 1506 illustrates accepting at least one past mental therapy associated with the at least one individual. For example, as shown in FIGS. 4 through 8, mental therapy accepter module 646 can accept at least one past mental therapy associated with the at least one individual. In one instance, mental therapy accepter module 646 can accept an indication of a past mental therapy associated with a specific individual. A past mental therapy may include a list and/or a record of at least one mental therapy, such as an anti-depressant medication, administered to at least one individual. In some instances, mental therapy accepter module 646 may include a computer processor.

Figure 16:
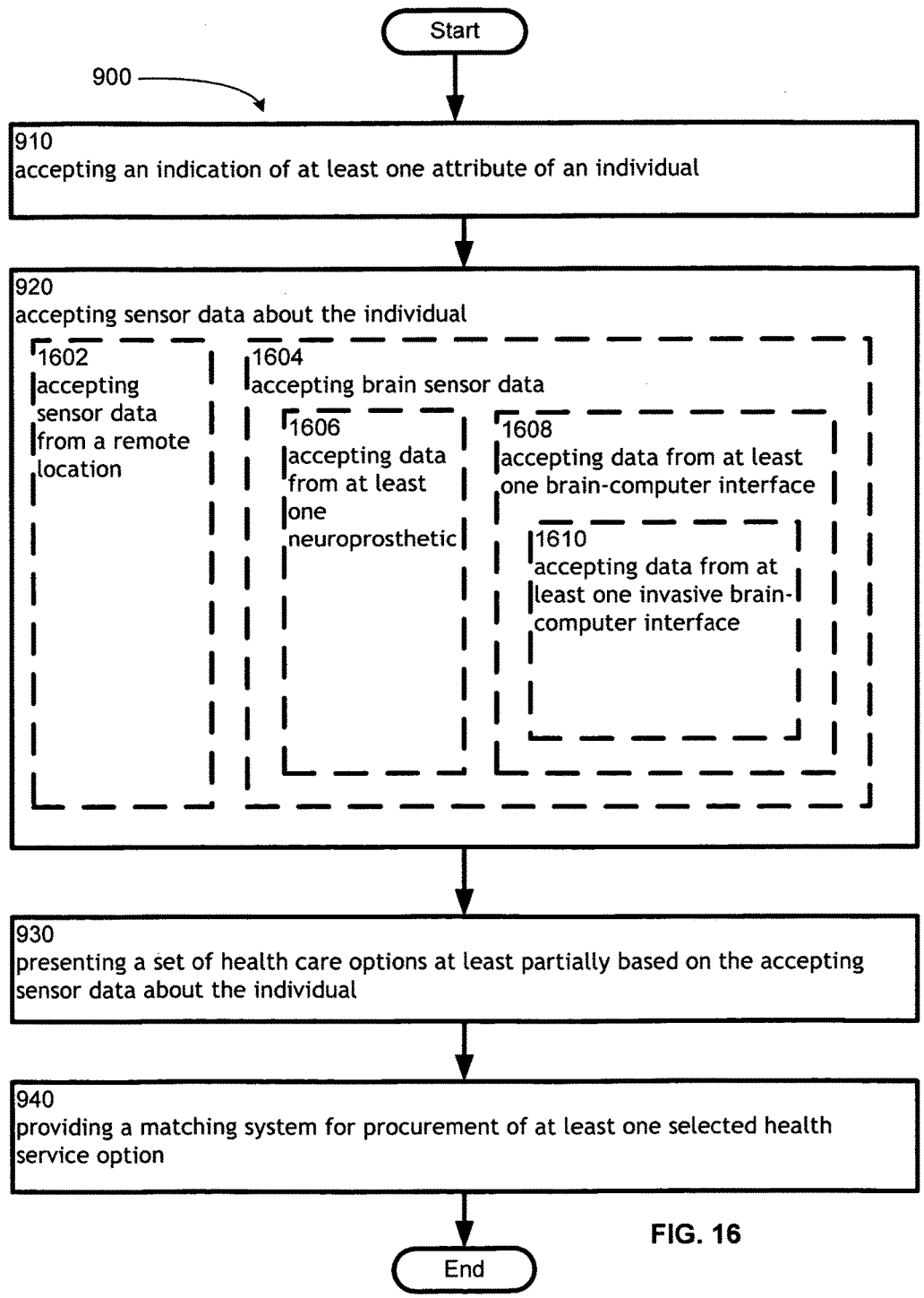
FIG. 16 illustrates an alternative embodiment of the operational flow of FIG. 9.

FIG. 16 illustrates alternative embodiments of the example operational flow 900 of FIG. 9. FIG. 16 illustrates example embodiments where operation 920 may include at least one additional operation. Additional operations may include operation 1602, operation 1604, operation 1606, operation 1608, and/or operation 1610.

Operation 1602 illustrates accepting sensor data from a remote location. For example, as shown in FIGS. 4 through 8, remote accepter module 648 can accept sensor data from a remote location. For example, remote accepter module 648 may receive one or more results from at least one sensor from a remote location. In one embodiment, remote accepter module 648 may receive data from a brain sensor from a remote location, such as from a research hospital in California when the remote accepter module 648 is located in Massachusetts. In some instances, remote accepter module 648 may include a computer processor and/or a communication device, for example a network modem and corresponding network circuitry.

Operation 1604 illustrates accepting brain sensor data. For example, as shown in FIGS. 4 through 8, brain sensor data accepter module 650 can accept brain sensor data. In an embodiment, brain sensor data accepter module 650 may accept from a brain sensor electrode array. One example of an electrode array may be found in Flaherty, U.S. Patent Publication No. 2007/0106143, which is incorporated herein by reference. In an embodiment, brain sensor data accepter module 650 may accept data detected by an electrode sensor that senses electrical signals generated by, for example, a patient while imagining movement. In this embodiment, the sensor may generate electrical signals that may be processed and/or accepted by, for example, brain sensor data accepter module 650. Some examples of a brain sensor may include non-invasive sensors, such as electroencephalogram (EEG) sensors, partially invasive sensors, such as electrocorticography sensors, and/or invasive sensors, such as implanted electrodes. A user 140 of a brain sensor may include a patient having a medical condition, an individual experiencing one or more symptoms, an asymptomatic individual, or the like. Brain sensor data may include an indication of physiological impairment, for example for cosmetic enhancement, pregnancy, or improvement in athletic performance. In an embodiment, brain sensor data accepter module 650 may accept brain sensor data from an array of wireless sensors attached to the outside of a user's 140 head. In this embodiment, the array of wireless sensors may wirelessly detect electrical signals in the user's 140 brain and wirelessly relay the information to brain sensor data accepter module 650. The electrical signals produced by the brain may indicate a certain condition of the brain and/or body, such as physical damage, disability, and/or cognitive dysfunction, and may additionally indicate the success of and/or the degree of success of a previously prescribed therapy. In some instances, brain sensor data accepter module 650 may include a computer processor.

Further, operation 1606 illustrates accepting data from at least one neuroprosthetic. For example, as shown in FIGS. 4 through 8, neuroprosthetic accepter module 652 can accept data from at least one neuroprosthetic. A neuroprosthetic may include a device or a series of devices that may function as a substitute for a motor, sensory, and/or cognitive modality that may have been damaged and/or may otherwise not function properly. For example, a neuroprosthetic may include a cochlear implant. A cochlear implant may serve to substitute the functions performed by an ear drum. In an embodiment, neuroprosthetic accepter module 652 may accept data from a cochlear implant. In this embodiment, the data accepted from the cochlear implant may serve to indicate, for example, that the cochlear implant is malfunctioning and a surgery for replacement is needed. In some instances, neuroprosthetic accepter module 652 may include a computer processor.

Further, operation 1608 illustrates accepting data from at least one brain-computer interface. For example, as shown in FIGS. 4 through 8, interface accepter module 654 can accept data from at least one brain-computer interface. A brain-computer interface may include a direct communication pathway between a brain and an external device, such as a neuroprosthetic and/or an array of electrodes. In an embodiment, interface accepter module 654 may accept data from an electrocorticography device. Some brain-computer interface devices may be intrusive, partially intrusive, and/or non-intrusive. In some instances, interface accepter module 654 may include a computer processor.

Further, operation 1610 illustrates accepting data from at least one invasive brain-computer interface. For example, as shown in FIGS. 4 through 8, interface accepter module 654 can accept data from at least one invasive brain-computer interface. An invasive brain-computer interface device may include a device implanted directly into the grey matter of the braim during a neurosurgery. In an embodiment, interface accepter module 654 may accept data from an array of electrodes implanted into a user's 140 visual cortex designed to detect electrical signals and/or the absence of electrical signals and analyzing a user's 140 visual perception. This may serve to assist in diagnosis of, for example, a visual disability. Another example of an invasive brain-computer interface may be found in Boling, U.S. Pat. No. 7,283,856, which is incorporated herein by reference. In some instances, interface accepter module 654 may include a computer processor.

Figure 17:
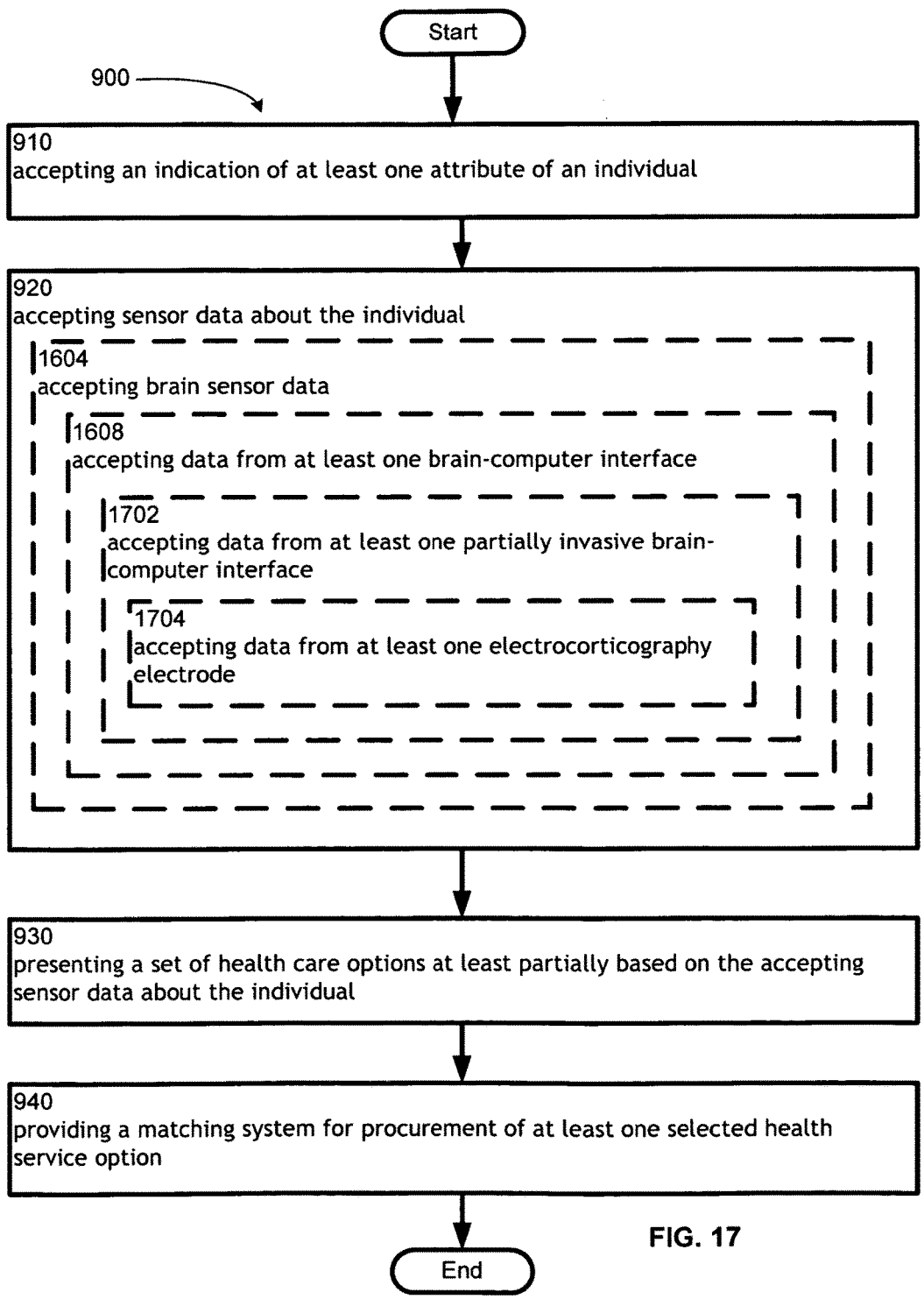
FIG. 17 illustrates an alternative embodiment of the operational flow of FIG. 9.

FIG. 17 illustrates alternative embodiments of the example operational flow 900 of FIG. 9. FIG. 17 illustrates example embodiments where operation 920 may include at least one additional operation. Additional operations may include operation 1702 and/or operation 1704.

Further, operation 1702 illustrates accepting data from at least one partially invasive brain-computer interface. For example, as shown in FIGS. 4 through 8, partial interface accepter module 656 can accept data from at least one partially invasive brain-computer interface. A partially invasive brain-computer interface may include a device implanted inside a person's skull but outside the brain. Some examples of a partially invasive brain-computer interface may include an electrocorticography device and/or a light reactive imaging device. In an embodiment, partial interface accepter module 656 may accept data from at least one partially invasive brain-computer interface, such as an electrode implanted between an individual's brain and skull. In some instances, partial interface accepter module 656 may include a computer processor.

Further, operation 1704 illustrates accepting data from at least one electrocorticography electrode. For example, as shown in FIGS. 4 through 8, electrocorticography accepter module 658 can accept data from at least one electrocorticography electrode. An electrocorticography device may include at least one electrode configured to measure electrical activity of the brain where, for example, the electrodes are embedded in a thin plastic pad that is placed above the cortex and beneath the dura matter. In an embodiment, electrocorticography accepter module 658 may accept data from at least one electrocorticography electrode configured to measure electrical signals in the brain of a patient that suffers from epilepsy. In this example, measuring the electrical signals may assist in determining the timing and/or intensity of an epileptic seizure and may help determine a suitable therapy for the patient. Another example of an electrocorticography device may be found in Leuthardt, U.S. Pat. No. 7,120,486, which is incorporated herein by reference. In some instances, electrocorticography accepter module 658 may include a computer processor and/or accepting circuitry, such as a modem.

Figure 18:
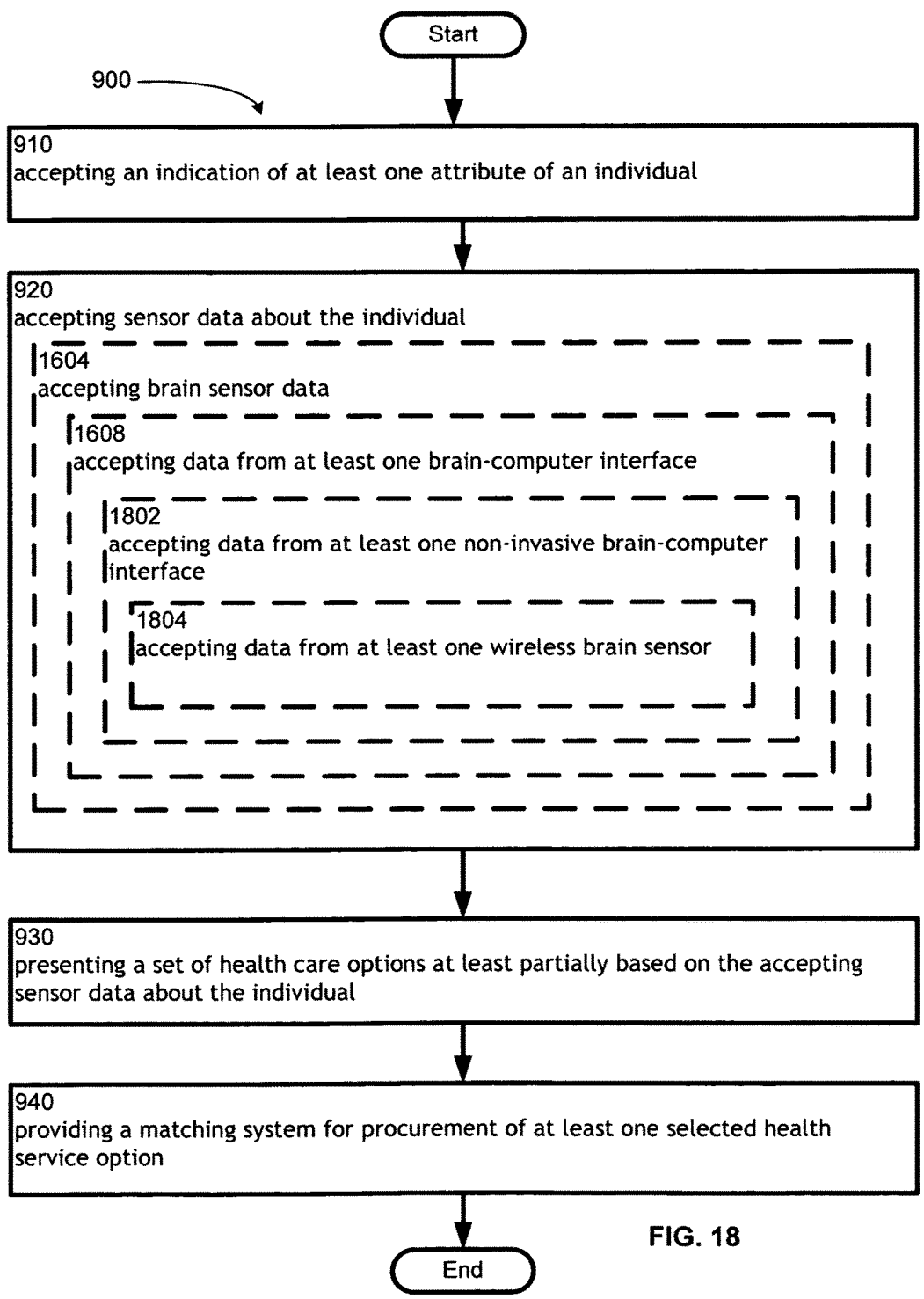
FIG. 18 illustrates an alternative embodiment of the operational flow of FIG. 9.

FIG. 18 illustrates alternative embodiments of the example operational flow 900 of FIG. 9. FIG. 18 illustrates example embodiments where operation 920 may include at least one additional operation. Additional operations may include operation 1802 and/or operation 1804.

Further, operation 1802 illustrates accepting data from at least one non-invasive brain-computer interface. For example, as shown in FIGS. 4 through 8, interface accepter module 654 can accept data from at least one non-invasive brain-computer interface. A non-invasive brain-computer interface may include a device that is able to measure signals from the brain without substantially interfering with and/or disturbing body tissue. In one embodiment, interface accepter module 654 may accept information from wireless brain sensors that are placed on an individual's head. Another example of a non-invasive brain-computer interface may include an electroencephalography sensor. In some instances, interface accepter module 654 may include a computer processor.

Further, operation 1804 illustrates accepting data from at least one wireless brain sensor. For example, as shown in FIGS. 4 through 8, wireless accepter module 660 can accept data from at least one wireless brain sensor. In an embodiment, wireless accepter module 660 may accept data from an array of brain sensors placed on the outside of an individual's head. In this embodiment, the array of brain sensors may detect electromagnetic waves created by neurons. The wireless brain sensor may be wirelessly connected to the wireless sensor accepter module 672. Additional examples of a wireless brain sensor may include Fish, U.S. Pat. No. 6,155,974, and Najafi, et al., U.S. Patent Publication No. 2009/0105557, both of which are incorporated herein by reference. In some instances, wireless accepter module 660 may include a computer processor.

Figure 19:
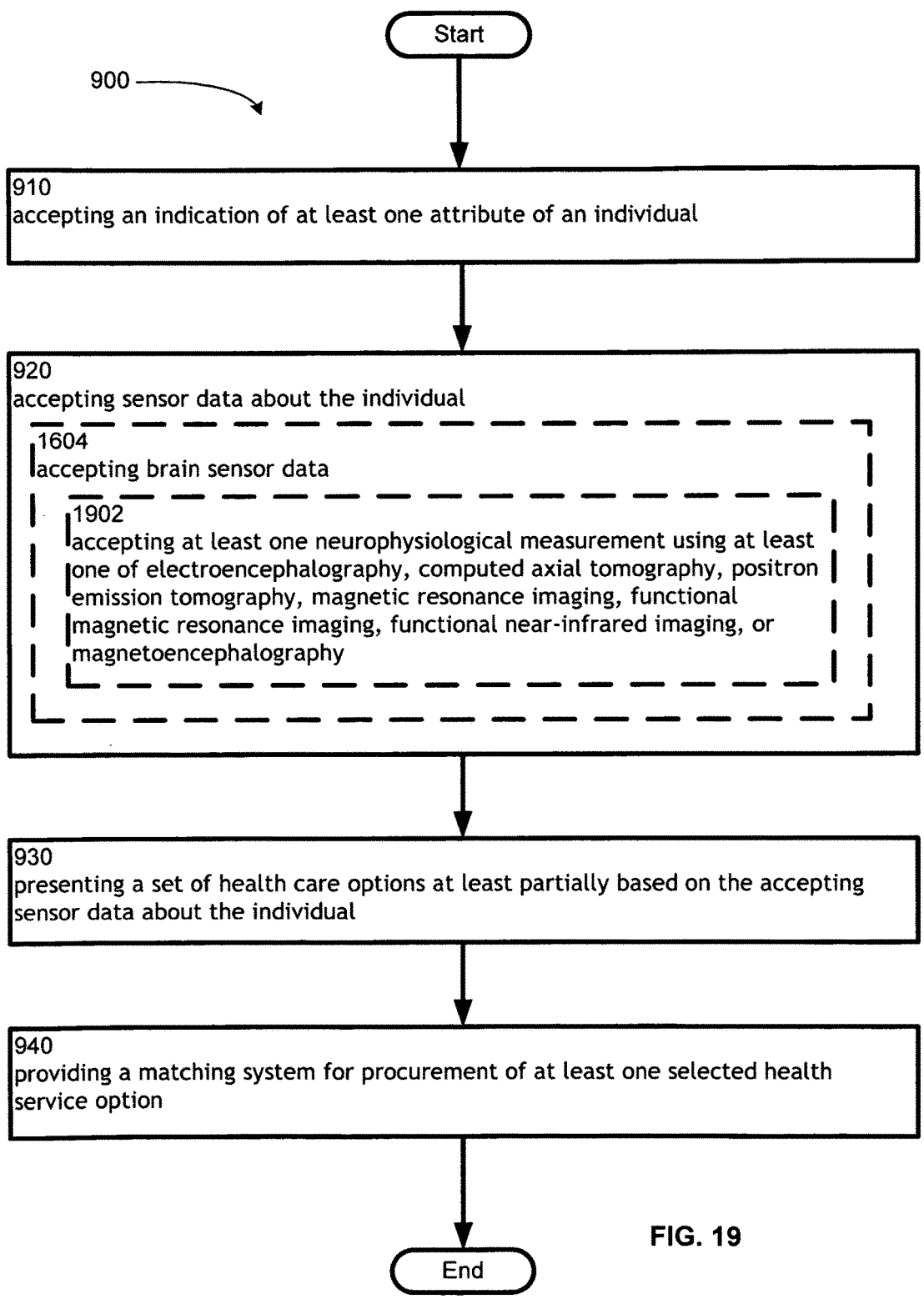
FIG. 19 illustrates an alternative embodiment of the operational flow of FIG. 9.

FIG. 19 illustrates alternative embodiments of the example operational flow 900 of FIG. 9. FIG. 19 illustrates example embodiments where operation 920 may include at least one additional operation. Additional operations may include operation 1902.

Further, operation 1902 illustrates accepting at least one neurophysiological measurement using at least one of electroencephalography, computed axial tomography, positron emission tomography, magnetic resonance imaging, functional magnetic resonance imaging, functional near-infrared imaging, or magnetoencephalography. For example, as shown in FIGS. 4 through 8, neurophysiological measurement accepter module 662 can accept at least one neurophysiological measurement using at least one of electroencephalography, computed axial tomography, positron emission tomography, magnetic resonance imaging, functional magnetic resonance imaging, functional near-infrared imaging, or magnetoencephalography. In some instances, neurophysiological measurement accepter module 662 may include a computer processor, and/or a medical device, such as an apparatus configured to perform a computed axial tomography scan.

Electroencephalography may include measuring the electrical activity of the brain by recording from electrodes placed on the scalp or, in special cases, subdurally, or in the cerebral cortex, or from remote sensors. The resulting traces are known as an electroencephalogram (EEG) and represent a summation of post-synaptic potentials from a large number of neurons. EEG is most sensitive to a particular set of post-synaptic potentials: those which are generated in superficial layers of the cortex, on the crests of gyri directly abutting the skull and radial to the skull. Dendrites that are deeper in the cortex, inside sulci, are in midline or deep structures (such as the cingulate gyrus or hippocampus) or that produce currents that are tangential to the skull make a smaller contribution to the EEG signal.

One application of EEG is event-related potential (ERP) analysis. An ERP is any measured brain response that is directly the result of a thought or perception. ERPs can be reliably measured using electroencephalography (EEG), a procedure that measures electrical activity of the brain, typically through the skull and scalp. As the EEG reflects thousands of simultaneously ongoing brain processes, the brain response to a certain stimulus or event of interest is usually not visible in the EEG. One of the most robust features of the ERP response is a response to unpredictable stimuli. This response is known as the P300 (P3) and manifests as a positive deflection in voltage approximately 300 milliseconds after the stimulus is presented.

A two-channel wireless brain wave monitoring system powered by a thermo-electric generator has been developed by IMEC (Interuniversity Microelectronics Centre, Leuven, Belgium). This device uses the body heat dissipated naturally from the forehead as a means to generate its electrical power. The wearable EEG system operates autonomously with no need to change or recharge batteries. The EEG monitor prototype is wearable and integrated into a headband where it consumes 0.8 milliwatts. A digital signal processing block encodes extracted EEG data, which is sent to a PC via a 2.4-GHz wireless radio link. The thermoelectric generator is mounted on the forehead and converts the heat flow between the skin and air into electrical power. The generator is composed of 10 thermoelectric units interconnected in a flexible way. At room temperature, the generated power is about 2 to 2.5-mW or 0.03-mW per square centimeter, which is the theoretical limit of power generation from the human skin. Such a device is proposed to associate emotion with EEG signals. See Clarke, "IMEC has a brain wave: feed EEG emotion back into games," EE Times online, http://www.eetimes.eu/design/202801063 (Nov. 1, 2007).

Computed axial tomography may include medical imaging employing tomography and digital geometry processing for generating a three-dimensional image of the inside of an object from a large series of two-dimensional X-ray images taken around a single axis of rotation. Positron emission tomography may include a nuclear medicine imaging technique, which produces a three-dimensional image and/or map of at least one functional process in the body. The system detects pairs of gamma rays emitted indirectly by a positron-emitting radionuclide (a tracer), which is introduced into the body on a biologically active molecule. Images of tracer concentration in 3-dimensional space within the body may then be reconstructed by computer analysis. Magnetic resonance imaging may include a medical imaging technique using a magnetic field to align the nuclear magnetization of hydrogen atoms in water in the body, resulting in an image of the body. Functional magnetic resonance imaging may include and imaging method for measuring haemodynamic response related to neural activity in the brain or spinal cord. Functional near-infrared imaging (fNIR) may include a spectroscopic neuro-imaging method for measuring the level of neuronal activity in the brain. Functional near-infrared imaging (fNIR) is based on neurovascular coupling, or the relationship between metabolic activity and oxygen level (oxygenated hemoglobin) in feeding blood vessels.

Magnetoencephalography includes measuring the magnetic fields produced by electrical activity in the brain using magnetometers such as superconducting quantum interference devices (SQUIDs) or other devices. Smaller magnetometers are in development, including a mini-magnetometer that uses a single milliwatt infrared laser to excite rubidium in the context of an applied perpendicular magnetic field. The amount of laser light absorbed by the rubidium atoms varies predictably with the magnetic field, providing a reference scale for measuring the field. The stronger the magnetic field, the more light is absorbed. Such a system is currently sensitive to the 70 fT range, and is expected to increase in sensitivity to the 10 fT range. See Physorg.com, "New mini-sensor may have biomedical and security applications," Nov. 1, 2007, http://www.physorg.com/news113151078.html, which is incorporated herein by reference.

Figure 20:
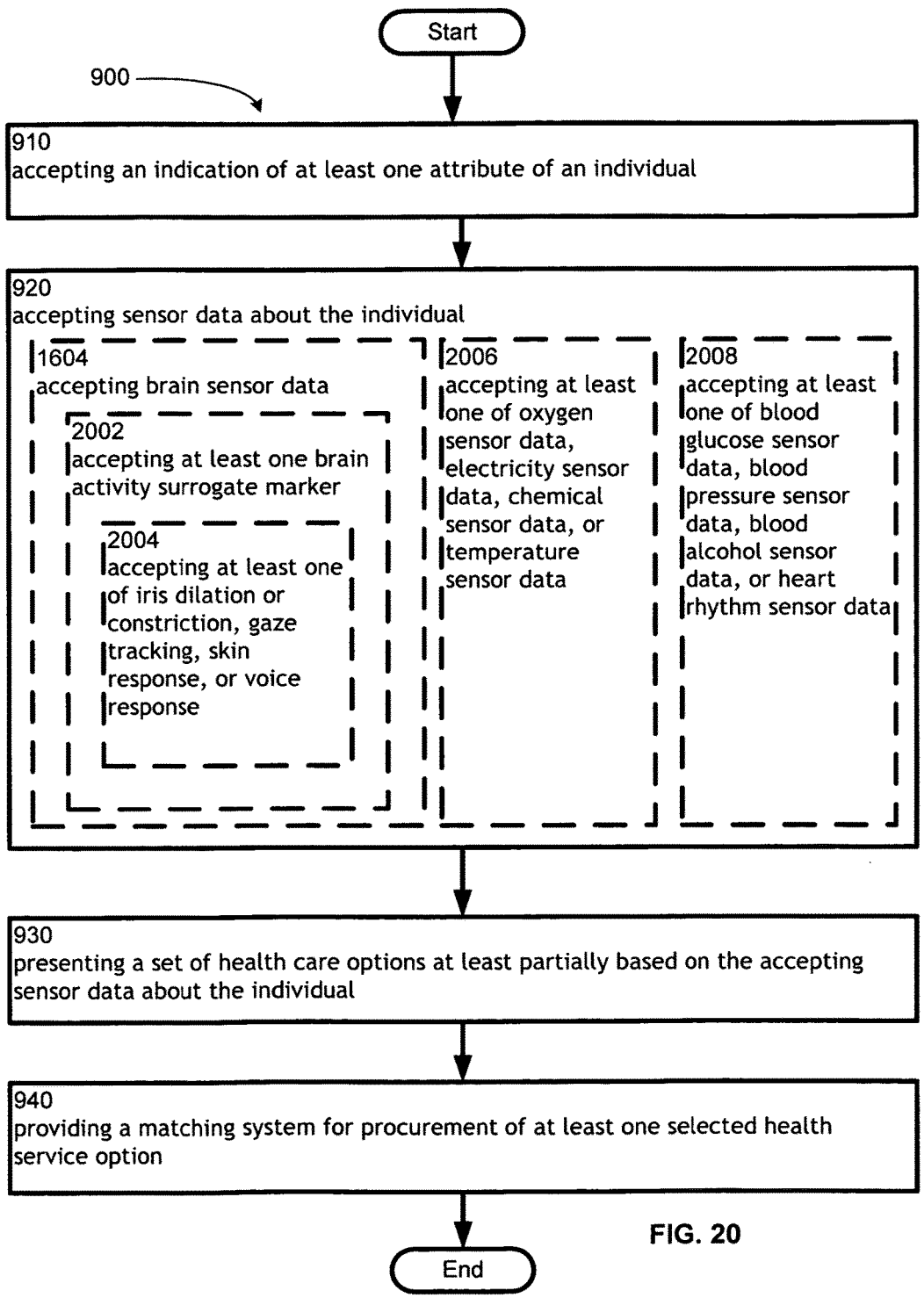
FIG. 20 illustrates an alternative embodiment of the operational flow of FIG. 9.

FIG. 20 illustrates alternative embodiments of the example operational flow 900 of FIG. 9. FIG. 20 illustrates example embodiments where operation 920 may include at least one additional operation. Additional operations may include operation 2002, operation 2004, operation 2006, and/or operation 2008.

Further, operation 2002 illustrates accepting at least one brain activity surrogate marker. For example, as shown in FIGS. 4 through 8, marker accepter module 664 can accept at least one brain activity surrogate marker. In some instances, marker accepter module 664 may include a computer processor and/or medical instrumentality configured to measure a surrogate marker, such as a stethoscope, a face recognition system, and/or a sphygmomanometer. Brain activity surrogate markers may include indicators of attention, approval, disapproval, recognition, cognition, memory, trust, or the like in response to a stimulus, other than measurement of brain activity associated with the stimulus. Some examples of surrogate markers may include a skin response to a stimulus; a face pattern indicative of approval, disapproval, or emotional state; eye movements or pupil movements indicating visual attention to an object; voice stress patterns indicative of a mental state, or the like. Surrogate markers may be used in conjunction with brain activity measurements for higher confidence in a predictive or interpretational outcome. For example, brain activation of the caudate nucleus in combination with calm voice patterns may increase confidence in a predictor of trust between a subject and a stimulus. Additional discussion regarding surrogate markers may be found in Cohn, J. N., *Introduction to Surrogate Markers*, CIRCULATION 109: IV20-21, American Heart Association, (2004), which is incorporated herein by reference.

For example, emotion links to cognition, motivation, memory, consciousness, and learning and developmental systems. Affective communication depends on complex, rule-based systems with multiple channels and redundancy built into the exchange system, in order to compensate if one channel fails. Channels can include all five senses: for example, increased heart-rate or sweating may show tension or agitation and can be heard, seen, touched, smelt or tasted. Emotional exchanges may be visible displays of body tension or movement, gestures, posture, facial expressions or use of personal space; or audible displays such as tone of voice, choice of pitch contour, choice of words, speech rate, etc. Humans also use touch, smell, adornment, fashion, architecture, mass media, and consumer products to communicate our emotional state. Universals of emotion that cross cultural boundaries have been identified. Cultural differences have also been identified. For example 'love' is generally categorized as a positive emotion in Western societies, but in certain Eastern cultures there is also a concept for 'sad love.' Accordingly, universal emotional triggers may be used to transcend cultural barriers.

When communicating with computers, people often treat new media as if they were dealing with real people. They often follow complex social rules for interaction and modify their communication to suit their perceived conversation partner. Much research has focused on the use of facial actions and ways of coding them. Speech recognition systems have also attracted attention as they grow in capability and reliability, and can recognize both verbal messages conveyed by spoken words, and non verbal messages, such as those conveyed by pitch contours.

System responses and means of expressing emotions also vary. Innovative prototypes are emerging designed to respond indirectly, so the user is relatively unaware of the response: for example by adaptation of material, such as changing pace or simplifying or expanding content. Other systems use text, voice technology, visual agents, or avatars to communicate. See Axelrod et al., "Smoke and Mirrors: Gathering User Requirements for Emerging Affective Systems," 26th Int. Conf. Information Technology Interfaces/TI 2004, Jun. 7-10, 2004, Cavtat, Croatia, pp. 323-328, which is incorporated herein by reference.

Further, operation 2004 illustrates accepting at least one of iris dilation or constriction, gaze tracking, skin response, or voice response. For example, as shown in FIGS. 4 through 8, response accepter module 666 can accept at least one of iris dilation or constriction, gaze tracking, skin response, or voice response. In some instances, response accepter module 666 may include a computer processor and/or medical instrumentality, such as a stethoscope and/or a sphygmomanometer. In one embodiment, response accepter module 666 may record changes in the movement of an individual's iris (with corresponding changes in the size of the pupil) before, during, and/or after administration of a bioactive agent and/or an artificial sensory experience. Such measurements of physiologic activity that indicate brain activity and/or mental state may be carried out at a time that is proximate to administration of a bioactive agent and/or an artificial sensory experience.

In one embodiment, response accepter module 666 may measure and/or record gaze tracking. In some instances, response accepter module 666 may include a camera that can monitor a subject's eye movements in order to determine whether the subject looks at a presented characteristic, for example, during a certain time period. For example, a camera may include a smart camera that can capture images, process them and issue control commands within a millisecond time frame. Such smart cameras are commercially available (e.g., Hamamatsu's Intelligent Vision System; http://jp.hamamatsu.com/en/product_info/index.html). Such image capture systems may include dedicated processing elements for each pixel image sensor. Other camera systems may include, for example, a pair of infrared charge coupled device cameras to continuously monitor pupil size and position as a user watches a visual target moving forward and backward. This can provide real-time data relating to pupil accommodation relative to objects on, for example, a user interface, such as a display. (e.g., http://jp.hamamatsu.com/en/rd/publication/scientific_american/common/pdf/scientific_0608.pdf).

Eye movement and/or iris movement may also be measured by video-based eye trackers. In these systems, a camera focuses on one or both eyes and records eye movement as the viewer looks at a stimulus. Contrast may be used to locate the center of the pupil, and infrared and near-infrared non-collumnated light may be used to create a corneal reflection. The vector between these two features can be used to compute gaze intersection with a surface after a calibration for an individual.

In one embodiment, response accepter module 666 may measure and/or record skin response. Brain activity may be determined by detection of a skin response associated with a stimulus. One skin response that may correlate with mental state and/or brain activity is galvanic skin response (GSR), also known as electrodermal response (EDR), psychogalvanic reflex (PGR), or skin conductance response (SCR). This is a change in the electrical resistance of the skin. There is a relationship between sympathetic nerve activity and emotional arousal, although one may not be able to identify the specific emotion being elicited. The GSR is highly sensitive to emotions in some people. Fear, anger, startle response, orienting response, and sexual feelings are all among the emotions which may produce similar GSR responses. GSR is typically measured using electrodes to measure skin electrical signals.

For example, an Ultimate Game study measured skin-conductance responses as a surrogate marker or autonomic index for affective state, and found higher skin conductance activity for unfair offers, and as with insular activation in the brain, this measure discriminated between acceptances and rejections of these offers. See Sanfey, "Social Decision-Making: Insights from Game Theory and Neuroscience," Science, vol. 318, pp. 598-601 (26 Oct. 2007), which is incorporated herein by reference. Other skin responses may include flushing, blushing, goose bumps, sweating, or the like.

In one embodiment, response accepter module 666 may measure and/or record voice response. Voice response may include speech captured by a microphone during presentation of a characteristic. Speech or voice can be measured, for example, by examining voice, song, and/or other vocal utterances of a subject before, during, and/or after administration of a bioactive agent and/or an artificial sensory experience to an individual. Such measurements may include, for example, as discussed above, layered voice analysis, voice stress analysis, or the like.

The reaction of an individual to an administered bioactive agent and/or an artificial sensory experience, such as an event in a virtual world may be a recognizable vocal exclamation such as "Wow, that's nice!" that may be detectable by a response accepter module 666, such as a microphone monitoring the subject while being administered an artificial sensory experience. A response accepter module 666 may include a voice response module and/or a speech recognition function, such as a software program or computational device that can identify and/or record an utterance of a subject as speech or voice data.

Operation 2006 illustrates accepting at least one of oxygen sensor data, electricity sensor data, chemical sensor data, or temperature sensor data. For example, as shown in FIGS. 4 through 8, sensor data accepter module 668 can accept at least one of oxygen sensor data, electricity sensor data, chemical sensor data, or temperature sensor data. In an embodiment, sensor data accepter module 668 may accept temperature sensor data from an infrared thermometer. One example of an oxygen sensor may include a pulse oximeter. Another example of an oxygen sensor may be found in Milstein et al., U.S. Pat. No. 5,106,482. Some examples of an electricity sensor may include an electroencephalography sensor and/or a piezoelectric ultrasound transducer. An additional example of an electricity sensor may include the bio-electric sensor found in Shahinpoor et al., U.S. Pat. No. 6,829,499, which is incorporated herein by reference. A chemical sensor may include, for example, a pH meter and/or a blood glucose sensor. An additional chemical sensor system may be found in Darrow et al., U.S. Pat. No. 6,480,730, which is incorporated herein by reference. Some examples of a temperature sensor may include a thermocouple and/or a thermometer. An additional example of a temperature system may be found in Takaki, U.S. Pat. No. 6,019,507, which is incorporated herein by reference. In some instances, sensor data accepter module 668 may include a computer processor and/or connecting circuitry, such as wired connections or a keyboard.

Operation 2008 illustrates accepting at least one of blood glucose sensor data, blood pressure sensor data, blood alcohol sensor data, or heart rhythm sensor data. For example, as shown in FIGS. 4 through 8, blood sensor data accepter module 670 can accept at least one of blood glucose sensor data, blood pressure sensor data, blood alcohol sensor data, or heart rhythm sensor data. In an embodiment, blood sensor data accepter module 670 may accept blood glucose sensor data. One example of a blood glucose meter may include the ACCU-CHEK Aviva Blood Glucose Meter available from Roche, Basel, Switzerland. An example of a blood pressure sensor may include a blood pressure cuff and/or a sphygmomanometer. An example of a blood alcohol sensor may include a breathalyzer such as the BACtrack S50 Breathalyzer, available from KHN Solutions LLC, San Francisco, Calif. An example of a heart rhythm sensor may include an EKG based heart rate monitor, such as the monitor found in Lo et al., U.S. Pat. No. 5,738,104, or the heart sound sensor found in Anderson et al., U.S. Patent Publication No. 2009/0030334, both of which are incorporated herein by reference. In some instances, blood sensor data accepter module 670 may include a computer processor.

Figure 21:
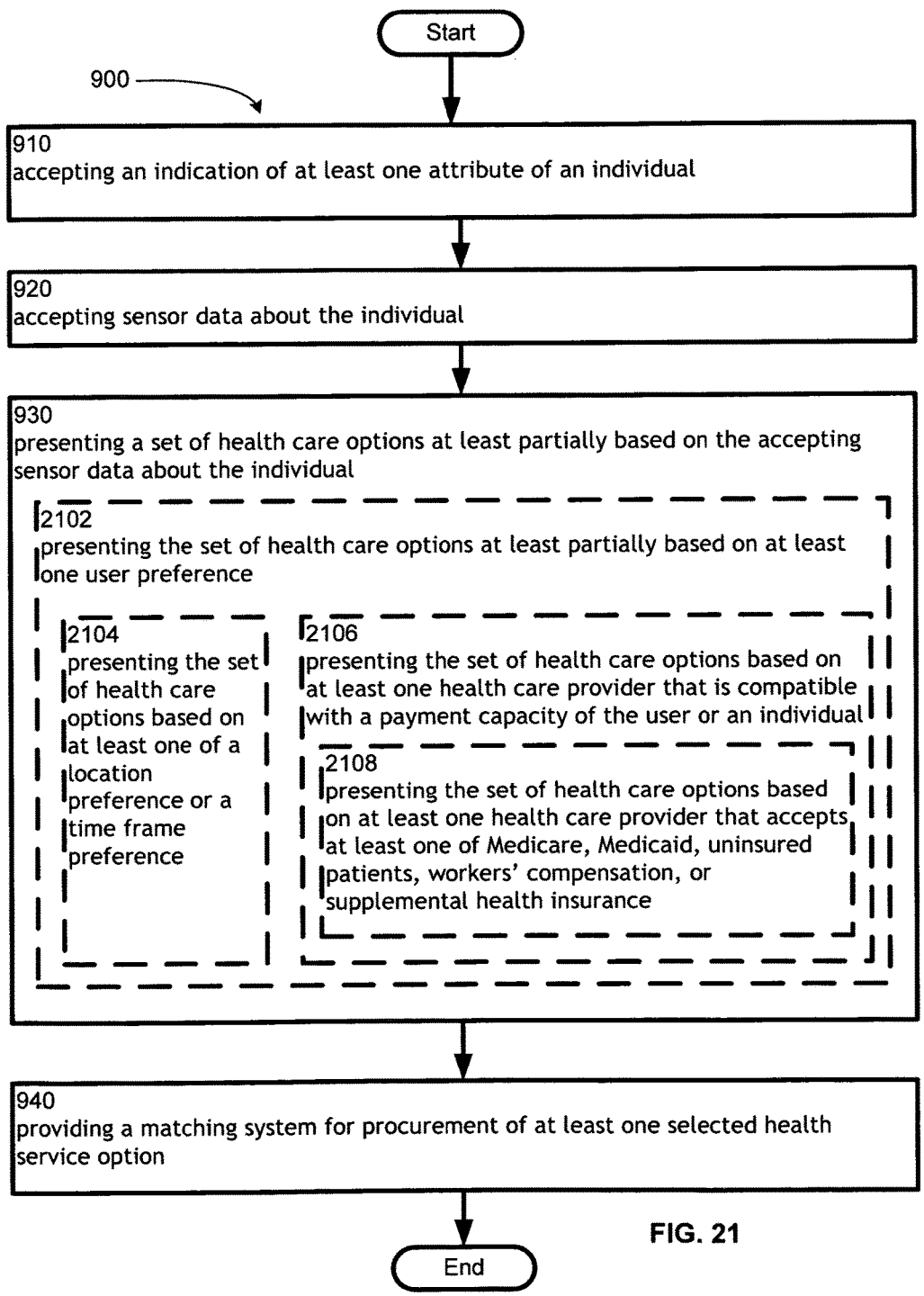
FIG. 21 illustrates an alternative embodiment of the operational flow of FIG. 9.

FIG. 21 illustrates alternative embodiments of the example operational flow 900 of FIG. 9. FIG. 21 illustrates example embodiments where operation 930 may include at least one additional operation. Additional operations may include operation 2102, operation 2104, operation 2106, and/or operation 2108.

Operation 2102 illustrates presenting the set of health care options at least partially based on at least one user preference. For example, as shown in FIGS. 4 through 8, preference presenter module 672 can present the set of health care options at least partially based on at least one user preference. In one embodiment, preference presenter module 672 may present, for example, a course of testing and/or treatment that takes into account one or more preferences or sensitivities of the individual, such as "treatments other than surgery," "local treatment options," "non-narcotic treatment options," or the like. In some instances, preference presenter module 672 may include a computer processor.

Further, operation 2104 illustrates presenting the set of health care options based on at least one of a location preference or a time frame preference. For example, as shown in FIGS. 4 through 8, time preference presenter module 674 can present the set of health care options based on at least one of a location preference or a time frame preference. In one embodiment, time preference presenter module 674 may present at least one health service option based on brain sensor data indicating a likelihood of epileptic seizure and a location such as "Miami-Dade County, Florida." A database of relevant service providers may contain, inter alia, location information allowing time preference presenter module 674 to present or determine, in this example, only relevant surgeons located in Miami-Dade County, Florida. Additionally, time preference presenter module 674 may filter out database results that include surgeons with, for example, less than five years of experience in practice and/or located outside of a specified geographic area, in some cases resulting in zero options being listed for a given therapy. In a case where no options are returned, other treatment options may be selected and a new search carried out. In some instances, time preference presenter module 674 may include a computer processor.

Further, operation 2106 illustrates presenting the set of health care options based on at least one health care provider that is compatible with a payment capacity of the user or an individual. For example, as shown in FIGS. 4 through 8, payment capacity presenter module 676 can present the set of health care options based on at least one health care provider that is compatible with a payment capacity of the user or an individual. In one embodiment, payment capacity presenter module 676 may present treatment options based on the key phrase "Alzheimer's" (determined by utilizing brain sensor data) and "Medicaid" as the payment capacity of the individual. In this example, treatment options available for payment with Medicaid may be determined and presented to the user. These treatment options will be limited to those approved by the U.S. Food and Drug Administration, while others, such as Aricept®, may be omitted as incompatible with Medicaid coverage. Conversely, if the payment capacity for the individual is high, off-label treatments and those with experimental status may be included as treatment options. Examples of other payment capacities include specific private insurance plans such as Premera, Blue Cross/Blue Shield, or the like. Other examples include Medicare, fee-for-service, point-of-service, preferred provider organizations, or health maintenance organizations. In some instances, payment capacity presenter module 676 may include a computer processor.

Further, operation 2108 illustrates presenting the set of health care options based on at least one health care provider that accepts at least one of Medicare, Medicaid, uninsured patients, workers' compensation, or supplemental health insurance. For example, as shown in FIGS. 4 through 8, insurance presenter module 678 can present the set of health care options based on at least one health care provider that accepts at least one of Medicare, Medicaid, uninsured patients, workers' compensation, or supplemental health insurance. In one embodiment, insurance presenter module 678 may present at least one health service option based on an accepted key phrase such as "Cerebral palsy" and "no insurance" as indications of at least one health-related status of an individual. In this example, insurance presenter module 678 may determine care options that are available to an uninsured individual, such as services provided by Denver Health, Denver's public health system, or the Seton System in Central Texas. In some instances, insurance presenter module 678 may include a computer processor.

Figure 22:
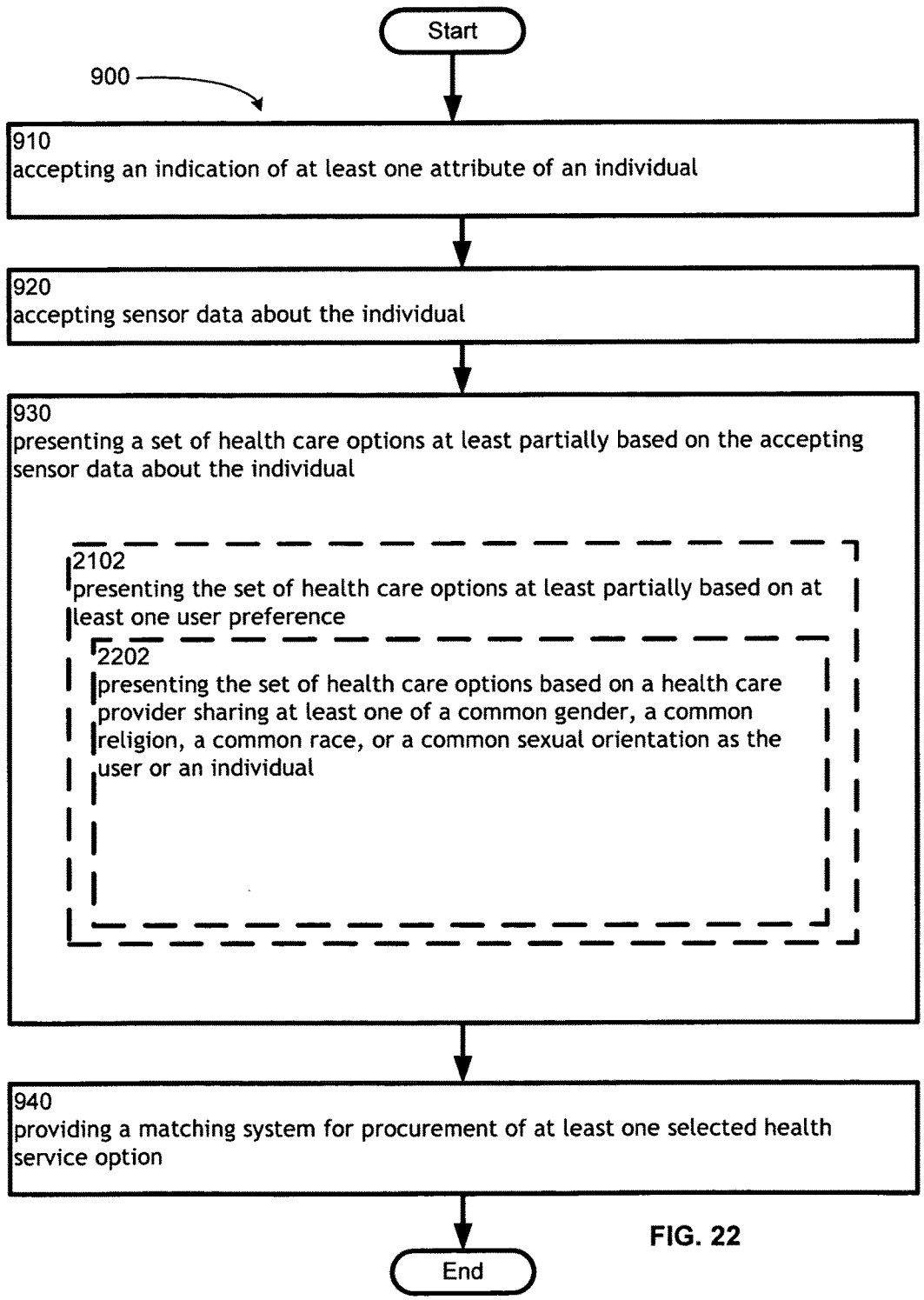
FIG. 22 illustrates an alternative embodiment of the operational flow of FIG. 9.

FIG. 22 illustrates alternative embodiments of the example operational flow 900 of FIG. 9. FIG. 22 illustrates example embodiments where operation 930 may include at least one additional operation. Additional operations may include operation 2202.

Further, operation 2202 illustrates presenting the set of health care options based on a health care provider sharing at least one of a common gender, a common religion, a common race, or a common sexual orientation as the user or an individual. For example, as shown in FIGS. 4 through 8, commonality presenter module 680 can present the set of health care options based on a health care provider sharing at least one of a common gender, a common religion, a common race, or a common sexual orientation as the user or an individual. In an embodiment, commonality presenter module 680 can present a set of physicians based on a user's preference for a Jewish doctor based at least in part on the user's religious beliefs as a Jew. In some instances, commonality presenter module 680 may include a computer processor.

Figure 23:
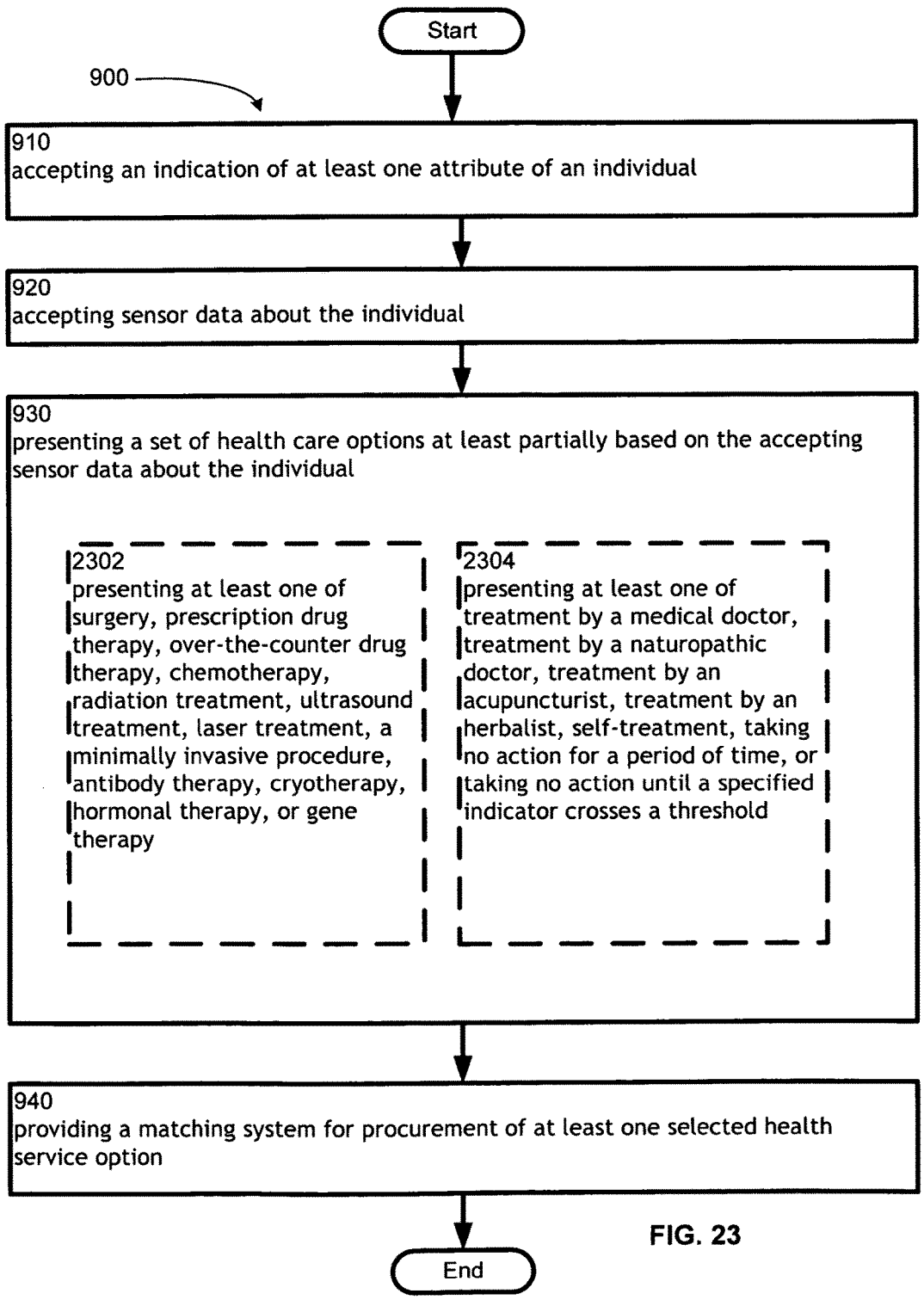
FIG. 23 illustrates an alternative embodiment of the operational flow of FIG. 9.

FIG. 23 illustrates alternative embodiments of the example operational flow 900 of FIG. 9. FIG. 23 illustrates example embodiments where operation 940 may include at least one additional operation. Additional operations may include operation 2302, and/or operation 2304.

Operation 2302 illustrates presenting at least one of surgery, prescription drug therapy, over-the-counter drug therapy, chemotherapy, radiation treatment, ultrasound treatment, laser treatment, a minimally invasive procedure, antibody therapy, cryotherapy, hormonal therapy, or gene therapy. For example, as shown in FIGS. 4 through 8, therapy presenter module 682 can present at least one of surgery, prescription drug therapy, over-the-counter drug therapy, chemotherapy, radiation treatment, ultrasound treatment, laser treatment, a minimally invasive procedure, antibody therapy, cryotherapy, hormonal therapy, or gene therapy. In one embodiment, therapy presenter module 682 may present health services options including, for example, options including prescription drug therapy and surgery based on data received from an array of non-invasive brain sensors that indicate motor neurone disease in an individual. In some instances, therapy presenter module 682 may include a computer processor.

Operation 2304 illustrates presenting at least one of treatment by a medical doctor, treatment by a naturopathic doctor, treatment by an acupuncturist, treatment by an herbalist, self-treatment, taking no action for a period of time, or taking no action until a specified indicator crosses a threshold. For example, as shown in FIGS. 4 through 8, action presenter module 684 can present at least one of treatment by a medical doctor, treatment by a naturopathic doctor, treatment by an acupuncturist, treatment by an herbalist, self-treatment, taking no action for a period of time, or taking no action until a specified indicator crosses a threshold. In one embodiment, action presenter module 684 may accept "narcolepsy" as an indication of health-related status and determine various health service options, such as treatment by an acupuncturist. In this embodiment, treatment presenter module 692 may present a list of acupuncturists with experience in treating narcolepsy. Virtually any combination of available testing/treatment options may be presented. Additionally, testing/treatment options may be narrowed by user preference. In some instances, action presenter module 684 may include a computer processor.

Figure 24:
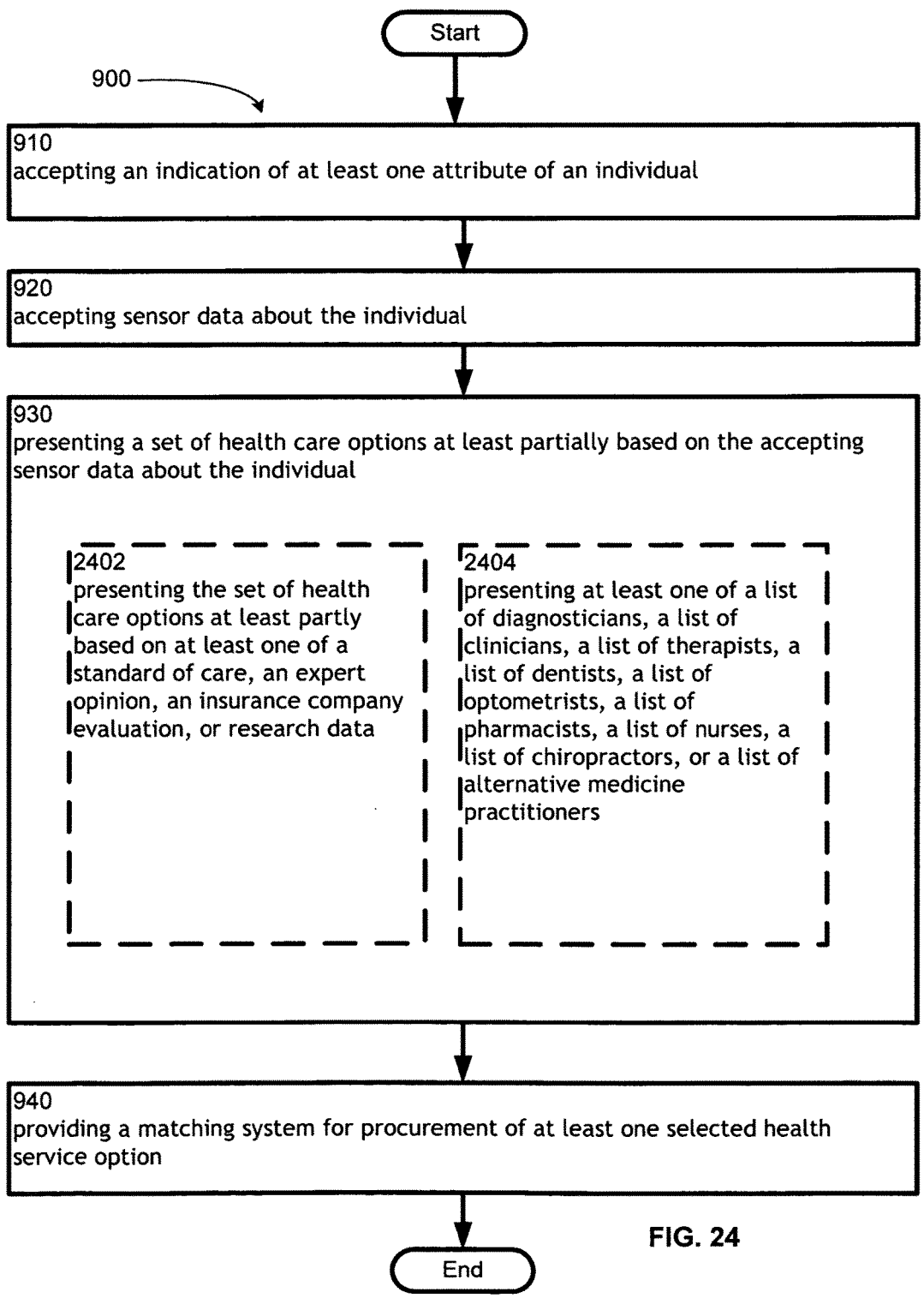
FIG. 24 illustrates an alternative embodiment of the operational flow of FIG. 9.

FIG. 24 illustrates alternative embodiments of the example operational flow 900 of FIG. 9. FIG. 24 illustrates example embodiments where operation 940 may include at least one additional operation. Additional operations may include operation 2402 and/or operation 2404.

Operation 2402 illustrates presenting the set of health care options at least partly based on at least one of a standard of care, an expert opinion, an insurance company evaluation, or research data. For example, as shown in FIGS. 4 through 8, standard presenter module 686 can present the set of health care options at least partly based on at least one of a standard of care, an expert opinion, an insurance company evaluation, or research data. In one embodiment, standard presenter module 686 may present a set of health service options based on a standard of care database. The standard of care database may include information, such as treatment options that are currently recommended by the medical community and/or approved by one or more insurance companies. In some instances, standard presenter module 686 may include a computer processor.

Operation 2404 illustrates presenting at least one of a list of diagnosticians, a list of clinicians, a list of therapists, a list of dentists, a list of optometrists, a list of pharmacists, a list of nurses, a list of chiropractors, or a list of alternative medicine practitioners. For example, as shown in FIGS. 4 through 8, health care provider presenter module 688 can present at least one of a list of diagnosticians, a list of clinicians, a list of therapists, a list of dentists, a list of optometrists, a list of pharmacists, a list of nurses, a list of chiropractors, or a list of alternative medicine practitioners. In one embodiment, health care provider presenter module 688 may, based on accepted brain sensor data, access a service provider database to determine a list of clinicians (e.g., surgeons). In this embodiment, provider presenter module 696 can present a list of clinicians experienced in treating neurological disorders indicated by the accepted brain sensor data. In another example, health care provider presenter module 688 may access a service provider database to provide a list of physicians who are pain specialists and a list of acupuncturists in response to receiving "head pain" as an indication of health-related status. In some instances, health care provider presenter module 688 may include a computer processor.

Figure 25:
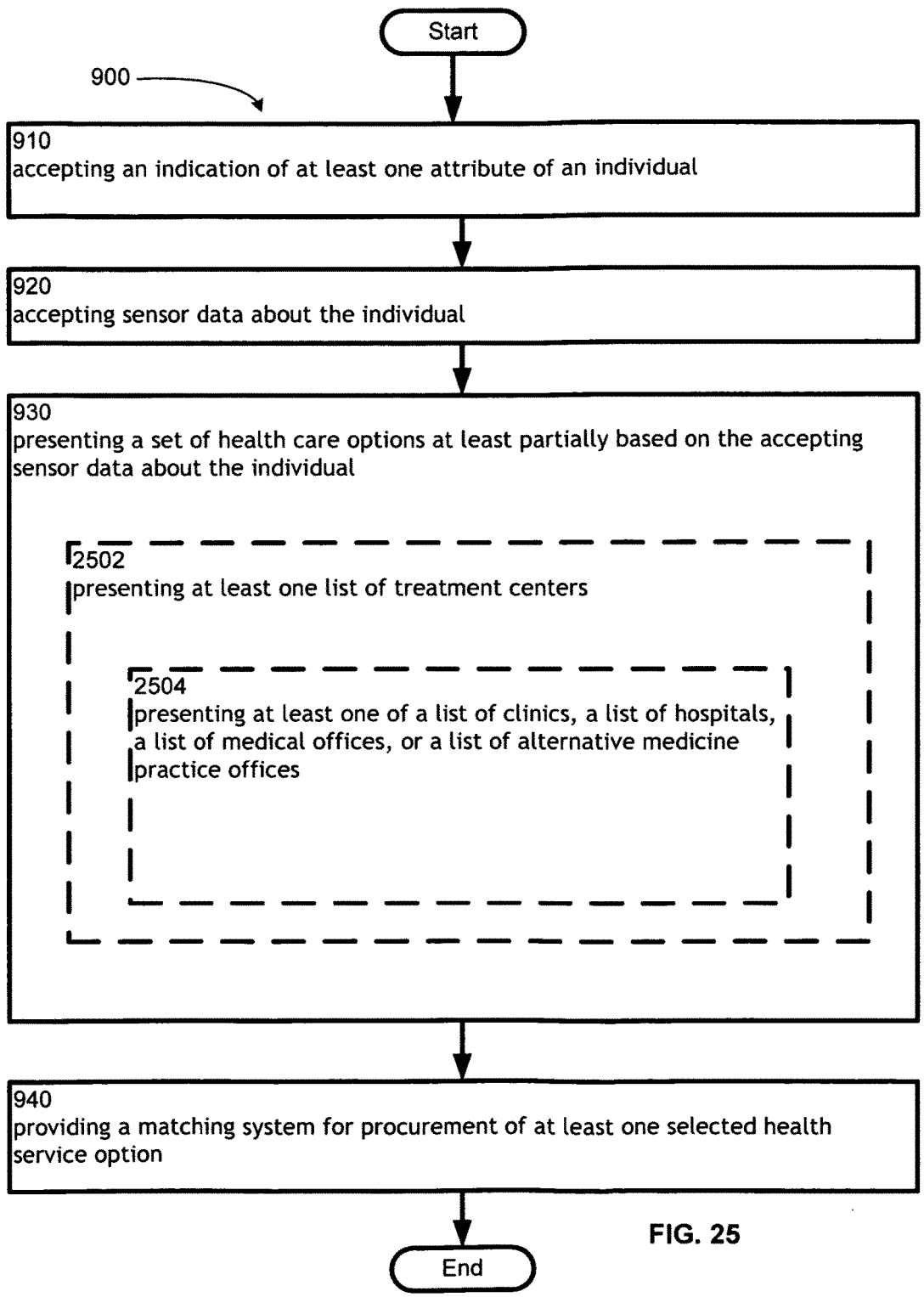
FIG. 25 illustrates an alternative embodiment of the operational flow of FIG. 9.

FIG. 25 illustrates alternative embodiments of the example operational flow 900 of FIG. 9. FIG. 25 illustrates example embodiments where operation 940 may include at least one additional operation. Additional operations may include operation 2502 and/or operation 2504.

Operation 2502 illustrates presenting at least one list of treatment centers. For example, as shown in FIGS. 4 through 8, center presenter module 690 can present at least one list of treatment centers. In one embodiment, center presenter module 690 may present a list of hospitals that perform a given medical procedure to a user at least partially based on data accepted from an array of brain sensors. In some instances, center presenter module 690 may include a computer processor.

Further, operation 2504 illustrates presenting at least one of a list of clinics, a list of hospitals, a list of medical offices, or a list of alternative medicine practice offices. For example, as shown in FIGS. 4 through 8, office presenter module 692 can present at least one of a list of clinics, a list of hospitals, a list of medical offices, or a list of alternative medicine practice offices. In one embodiment, office presenter module 692 may present a list of dementia treatment clinics for an individual in need of dementia-related health service options. In another example, office presenter module 692 may determine a list of epilepsy clinics. In some instances, office presenter module 692 may include a computer processor.

Figure 26:
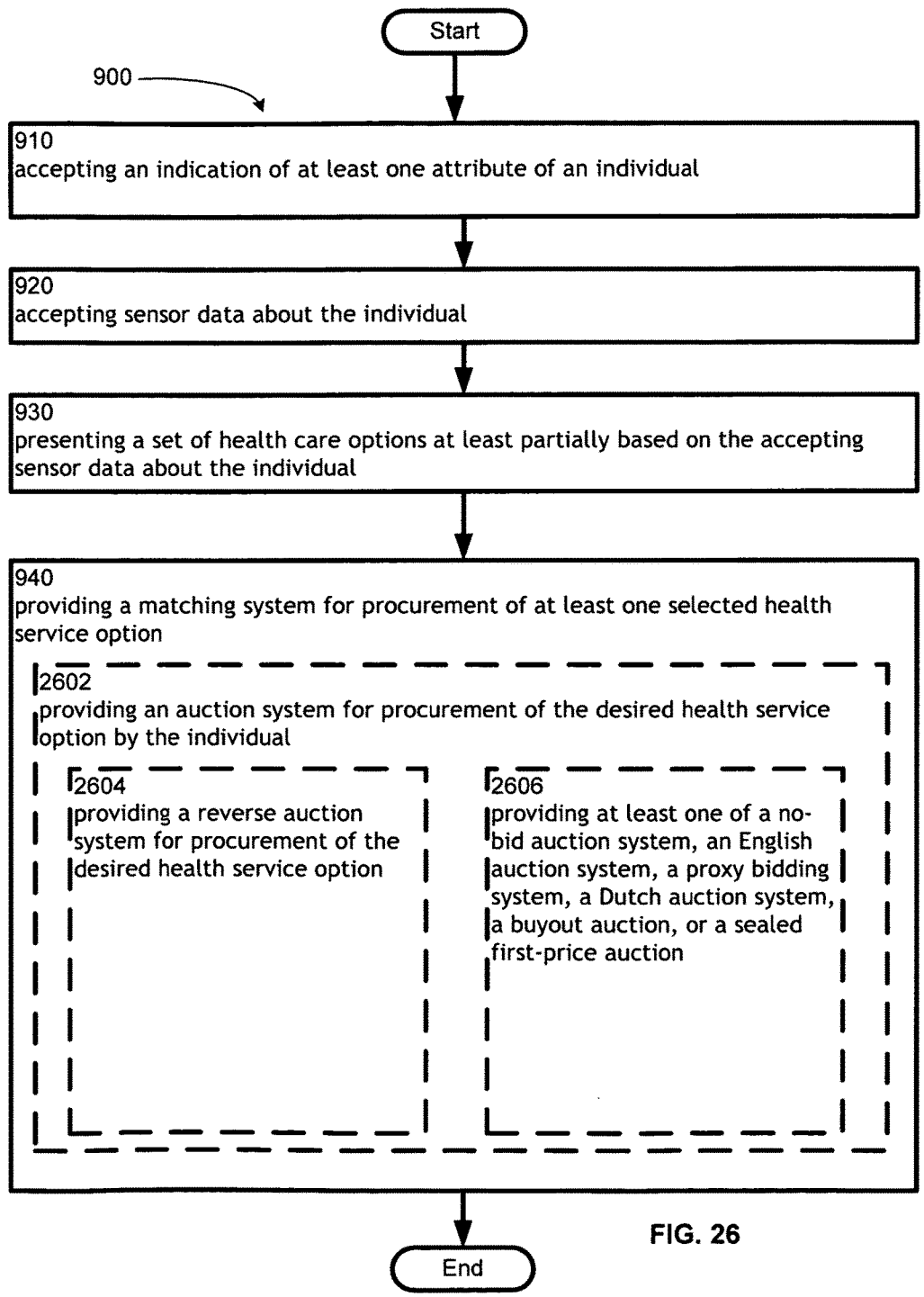
FIG. 26 illustrates an alternative embodiment of the operational flow of FIG. 9.

FIG. 26 illustrates alternative embodiments of the example operational flow 900 of FIG. 9. FIG. 26 illustrates example embodiments where operation 940 may include at least one additional operation. Additional operations may include operation 2602, operation 2604, and/or operation 2606.

Operation 2602 illustrates providing an auction system for procurement of the desired health service option by the individual. For example, as shown in FIGS. 4 through 8, auction provider module 694 can provide an auction system for procurement of the desired health service option by the individual. In one embodiment, auction provider module 694 may match an individual's chosen health-related service with a service provider 160 via a traditional auction. In one example, auction provider module 694 may accept a health service option and a zip code, for example "obstetrics" and the 10021 zip code. Auction provider module 694 can then access a service provider database to generate a list of obstetrics care providers in the 10021 zip code, including physicians, hospitals, and/or nontraditional service providers such as midwives or birth doulas. Auction provider module 694 can then solicit bids from these providers in order to rank them by any of a number of criteria, including cost per unit service, cost per unit time, availability, location, or the like. These criteria may be defined by user 140 and accessed by, for example, auction provider module 694 from a user preference database. Such an auction may run for a defined time period and/or be limited to a defined number of service providers. In some instances, auction provider module 694 may include a computer processor.

Further, operation 2604 illustrates providing a reverse auction system for procurement of the desired health service option. For example, as shown in FIGS. 4 through 8, reverse auction provider module 696 can provide a reverse auction system for procurement of the desired health service option. In one embodiment, reverse auction provider module 696 may match take bids from service providers to drive down the cost of the health service option. A reverse auction, also called a procurement auction, e-auction, sourcing event, e-sourcing, or eRA, is a tool commonly used in industrial business-to-business procurement. It is a type of auction in which the role of the buyer and seller are reversed, with the primary objective to drive purchase prices downward. In an ordinary auction (also known as a forward auction), buyers compete to obtain a good or service. In a reverse auction, sellers compete to obtain business. In some instances, reverse auction provider module 696 may include a computer processor.

In one embodiment of a reverse auction, a user 140 may contract with a market maker to help make the necessary preparations to conduct the reverse auction. This may include finding service providers, training new and incumbent service providers, organizing the auction, managing the auction event, and providing auction data to user 140 to facilitate decision making. In one embodiment, a market maker, on behalf of the user 140, issues a request for quotation (RFQ) to purchase a particular health service option or group of options (called a "lot"). At the designated day and time, several service providers log on to the auction site and input several quotes over a 30-90 minute period. These quotes reflect the prices at which they are willing to supply the requested health service option.

In one embodiment, quoting performed in real-time via the Internet results in dynamic bidding. This helps achieve a rapid downward price pressure that is not normally attainable using traditional static 3-quote paper-based bidding processes. The prices that a user 140 may obtain in the reverse auction reflect the market which is created at the moment in time when the auction is held. The user 140 may award a contract to the service provider who bids the lowest price. Or, a user 140 could award a contract to a service provider who bid higher prices depending upon the preferences of user 140, e.g., specific needs with regards to quality, lead-time, capacity, or other value-adding capabilities.

The use of optimization software has become popular to help users 140 determine which service provider to choose. Such optimization software may include relevant user 140 and service provider business data, including preferences and/or constraints.

Further, operation 2606 illustrates providing at least one of a no-bid auction system, an English auction system, a proxy bidding system, a Dutch auction system, a buyout auction, or a sealed first-price auction. For example, as shown in FIGS. 4 through 8, various auction provider module 698 can provide at least one of a no-bid auction system, an English auction system, a proxy bidding system, a Dutch auction system, a buyout auction, or a sealed first-price auction. In one embodiment, various auction provider module 698 may provide a proxy bidding system wherein service providers may submit bids to an insurance company as proxy holder bidders in a reverse auction for a health service option. In one embodiment, a service provider may tell an auctioneer the absolute minimum fee for a service that they are willing to accept from a user 140, as a bid for providing a desired health service option. An auctioneer such as a dedicated web site or an insurance company may then place a bid on behalf of the service provider. The auctioneer or insurance company then continues to bid on behalf of the service provider, whenever he or she is outbid by another service provider's bid, until the minimum is exceeded or the auction is won. In some instances, various auction provider module 698 may include a computer processor.

A no-bid auction system is one in which a service provider lists a price for a given health service option subject to election or not by a user 140, for example. One example of a no-bid auction is the "buy-it-now" feature of eBay, in which an item may be purchased for an advertised price as an alternative to a traditional auction with competing bids. In one embodiment, a no-bid auction may be mediated by various auction provider module 698. Various auction provider module 698 can find a single best service provider for an interested user 140 based on an accepted indication of at least one health-related status and/or user preference data, for example from a user preference database.

In one embodiment of an English auction, also known as an open ascending price auction, users 140 may bid openly against one another, with each subsequent bid higher than the previous bid. An auctioneer may announce prices, bidders may call out their bids themselves (or have a proxy call out a bid on their behalf), or bids may be submitted electronically with the highest current bid publicly displayed. In some cases a maximum bid might be left with the auctioneer, who may bid on behalf of the bidder according to the bidder's instructions. The auction ends when no participant is willing to bid further, at which point the highest bidder pays their bid. Alternatively, if a service provider has set a minimum sale price in advance (the reserve price) and the final bid does not reach that price then the contract for a desired health service option remains unsold. In some embodiments, the auctioneer may set a minimum amount by which the next bid must exceed the current highest bid. The most significant distinguishing factor of this auction type is that the current highest bid is always available to potential bidders. At least two bidders are required.

Proxy bidding is an implementation of an English second-price auction, in which the winning bidder pays the price of the second-highest bid plus a defined increment. It differs from a Vickrey auction in that bids are not sealed; the "current highest bid" (defined as second-highest bid plus bid increment) is always displayed. In a standard first-price English auction the winner pays the amount of their bid, regardless of competitors' bids, and it is therefore desirable to place a bid that exceeds the current highest bid by the smallest possible increment. Under proxy bidding, however, the price paid is determined only by competitors' bids and not by the amount of the new bid, and so there is no economically rational incentive to place a bid below the amount one is willing to pay, or to place multiple increasing bids. An economically rational bidder will therefore bid the maximum amount they are willing to pay on their first bid, and never raise their bid.

In a Dutch auction, also known as an open descending price auction, the auctioneer begins with a high asking price which is lowered until some participant is willing to accept the auctioneer's price. The winning participant pays the last announced price. The term "Dutch auction" is also sometimes used to describe online auctions where several identical goods are sold simultaneously to an equal number of high bidders.

A buyout auction is an auction with a set price ("buyout price") that any bidder can accept at any time during the auction, thereby immediately ending the auction and winning the service contract. If no bidder elects the buyout option before the end of bidding the highest bidder wins and pays their bid. Buyout options can be either temporary or permanent. In a temporary buyout auction the option to buy out the auction is no longer available after the first bid is placed. In a permanent buyout auction the buyout option remains available throughout the entire auction until the close of bidding. The buyout price can either remain the same throughout the entire auction, or vary throughout according to preset rules or at the discretion of, for example, service provider.

In a sealed first-price auction, also known as a first-price sealed-bid auction, all bidders simultaneously submit sealed bids so that no bidder knows the bid of any other participant. The highest bidder pays the price they submitted. This type of auction is distinct from the English auction, in that bidders can only submit one bid each. Furthermore, as bidders cannot see the bids of other participants they cannot adjust their own bids accordingly.

Figure 27:
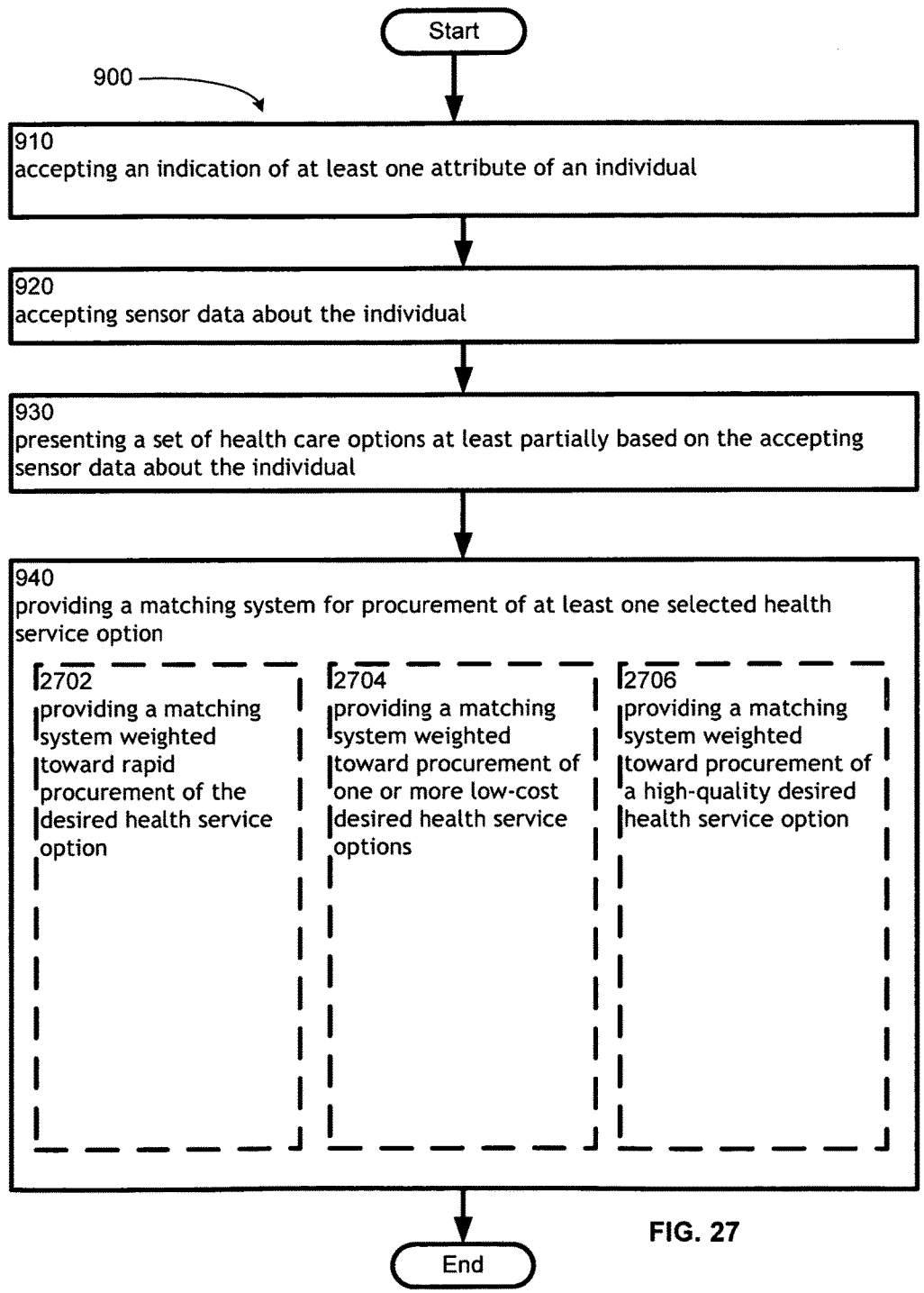
FIG. 27 illustrates an alternative embodiment of the operational flow of FIG. 9.

FIG. 27 illustrates alternative embodiments of the example operational flow 900 of FIG. 9. FIG. 27 illustrates example embodiments where operation 940 may include at least one additional operation. Additional operations may include operation 2702, operation 2704, and/or operation 2706.

Operation 2702 illustrates providing a matching system weighted toward rapid procurement of the desired health service option. For example, as shown in FIGS. 4 through 8, rapid option provider module 700 can provide a matching system weighted toward rapid procurement of the desired health service option. In one embodiment, rapid option provider module 700 may accept "canaloplasty" and "cataract surgery" as at least one indication of a health-related status. User preference data may also be accepted such as "immediate availability" and "Johnstown, Pa". Rapid option provider module 700 may then determine a list of eye surgeons capable of addressing glaucoma and cataract issues for the individual/user 140. In this example, a rapid option provider module 700 weighted toward rapid procurement of the desired health service option may provide an internet auction among determined physicians such that the auction is scheduled to end within, for example, three business days instead of a standard five business days or seven days, for example. In an alternative example, rapid option provider module 700 may expedite procurement of a desired health service option by providing a no-bid auction or by providing a single best match for an available service provider. In some instances, rapid option provider module 700 may include a computer processor.

Operation 2704 illustrates providing a matching system weighted toward procurement of one or more low-cost desired health service options. For example, as shown in FIGS. 4 through 8, low-cost option provider module 702 can provide a matching system weighted toward procurement of one or more low-cost desired health service options. In one embodiment, low-cost option provider module 702 may take advantage of a price differential between two or more markets, striking a combination of matching deals that capitalize upon the imbalance, the profit and/or savings being the difference between the market prices. For example, low-cost option provider module 702 may accept bids from, for example, hospitals and health maintenance organizations in various geographic areas or markets, compare the bids, and select a match on the basis of the best cost differential and/or lowest cost for the user 140/individual. In one embodiment, low-cost option provider module 702 may take into account travel distance in selecting a low-cost health care services provider. For example, while health care costs may vary between large and small markets, a resident of a large market may not want to choose a low-cost health care services provider in a small market for reasons of quality and/or convenience. Therefore, whereas low-cost option provider module 702 may identify a spread between bid prices for identical services in each market, low-cost option provider module 702 may factor in such factors as distance, number of procedures performed historically, staff expertise, user preference data from user preference database, or the like in providing a matching system for procurement of a desired health service option. Low-cost option provider module 702 may then provide at least one low-cost option. It should be understood that performing the actual matching function for a user 140/individual is one way of providing a matching system for procurement of a desired health service option. In some instances, low-cost option provider module 702 may include a computer processor.

Operation 2706 illustrates providing a matching system weighted toward procurement of a high-quality desired health service option. For example, as shown in FIGS. 4 through 8, high-quality option provider module 704 can provide a matching system weighted toward procurement of a high-quality desired health service option. In one embodiment, high-quality option provider module 704 may, based on a determined at least one health service option for the individual based on the indication of at least one health-related status, match user 140 with the highest-quality health service option available. For example, where treatment planning module has determined neurosurgery as a health service option for glioblastoma multiforme, high-quality option provider module 704 may match the top-ranked Mayo Clinic in Rochester, Minn. with an individual's personal assistant as the user 140. Then, high-quality option provider module 704 may provide and/or present the Mayo clinic to the individual and/or user 140. In some instances, high-quality option provider module 704 may include a computer processor.

Figure 28:
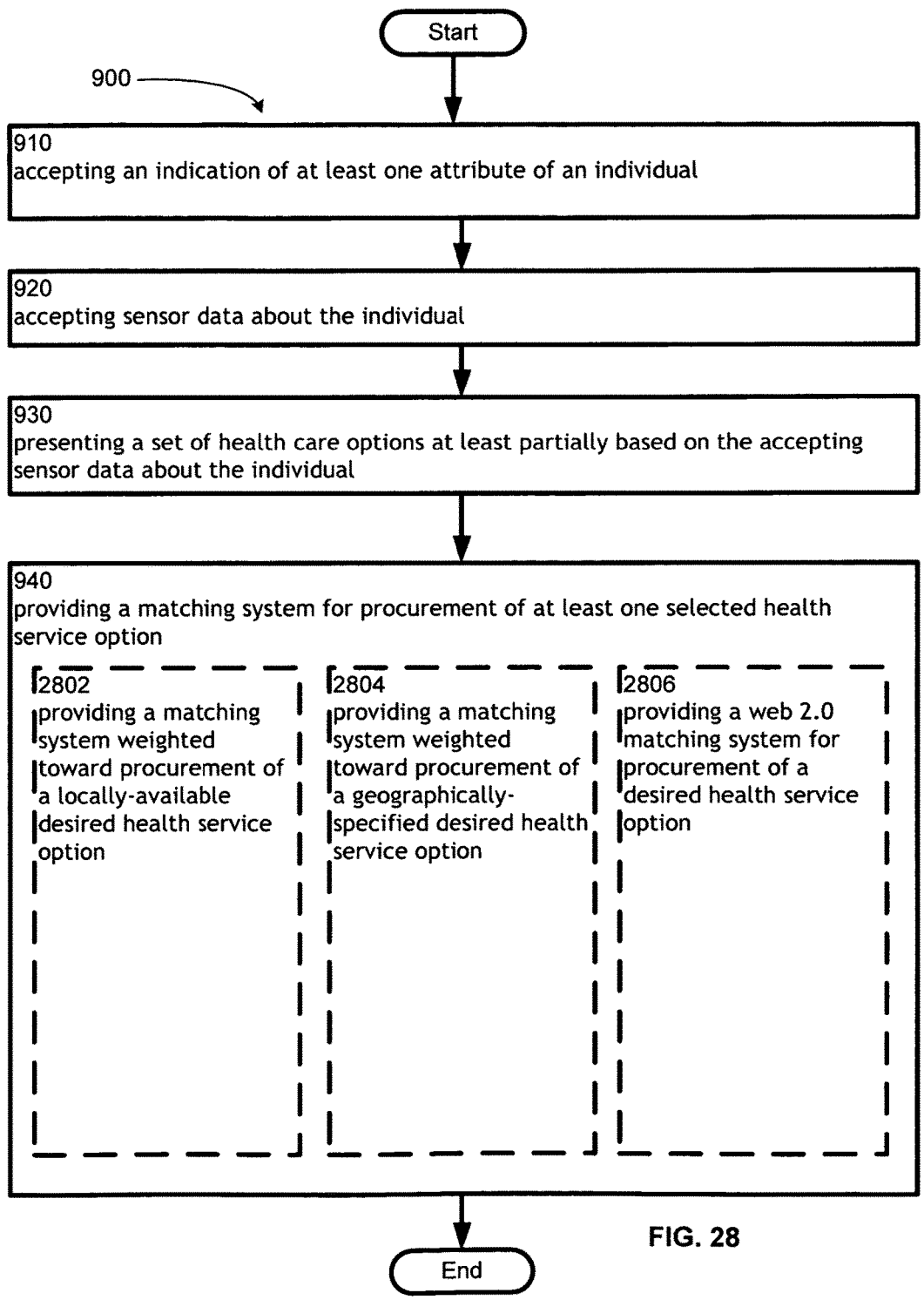
FIG. 28 illustrates an alternative embodiment of the operational flow of FIG. 9.

FIG. 28 illustrates alternative embodiments of the example operational flow 900 of FIG. 9. FIG. 28 illustrates example embodiments where operation 940 may include at least one additional operation. Additional operations may include operation 2802, operation 2804, and/or operation 2806.

Operation 2802 illustrates providing a matching system weighted toward procurement of a locally-available desired health service option. For example, as shown in FIGS. 4 through 8, local option provider module 706 can provide a matching system weighted toward procurement of a locally-available desired health service option. In one embodiment, local option provider module 706 may initiate a reverse auction in which health care service providers bid on a given desired health services option. In this example, local option provider module 706 may filter a list of physicians, for example, as determined by local option provider module 706 to include only those within a local area. Alternatively, local option provider module 706 may favor bids from local service providers during an auction to match user 140 with a service provider, perhaps based on a preference from user preference database. Then, local option provider module 706 may provide and/or present to user 140 and/or other interested individual the locally-available desired health service option. In some instances, local option provider module 706 may include a computer processor.

Operation 2804 illustrates providing a matching system weighted toward procurement of a geographically-specified desired health service option. For example, as shown in FIGS. 4 through 8, geographic option provider module 708 can provide a matching system weighted toward procurement of a geographically-specified desired health service option. In one embodiment, geographic option provider module 708 may initiate a reverse auction in which health care service providers in a foreign country bid on a given desired health services option. In this example, geographic option provider module 708 may filter a list of service providers, for example, as determined by geographic option provider module 708 to include only those within a certain geographic area, for example, "India." Accordingly this system can be used to match a user 140 and/or individual in one country with a service provider in another country or region. One example of this kind of specific geographic matching is health care tourism, also known as medical travel, health tourism, or global healthcare, in which an individual in need of health care travels to a foreign country for a lower cost service, a stimulating travel experience, and/or specialist health care, or the like. Alternatively, geographic option provider module 708 may favor bids from service providers in a specified geographic region during an auction to match user 140 with a service provider, perhaps based on a preference from a user preference database. Then, geographic option provider module 708 may provide and/or present to user 140 at least one service provider. In some instances, geographic option provider module 708 may include a computer processor.

Operation 2806 illustrates providing a web 2.0 matching system for procurement of a desired health service option. For example, as shown in FIGS. 4 through 8, web option provider module 710 can provide a web 2.0 matching system for procurement of a desired health service option. In one embodiment, web option provider module 710 may conduct an internet auction to match a user 140 with a service provider to provide a desired health services option, such as open heart surgery. In this example, auction progress may be monitored by an auctioneer and/or user 140 by way of a web 2.0 application, such as that used by the ZorgVeiling Care Auction system discussed above. Additionally, web option provider module 710 may monitor and/or choose the web 2.0 application. This system manages results with IBM's Dashboard Solutions for WebSphere Portal, in which interactive portlets allow for filtering of data, and big-picture monitoring of bidding progress and results. Such web 2.0 systems provide security in terms of SSL certificates, database encryption, HTTP redirect functionality, firewalls, secure cybercenters, and the like. These systems can also be implemented using readily available hardware from a single supplier, e.g., Microsoft and IBM. Microsoft products provide SQL Server-oriented client environments complete with OLAP viewing, dashboarding, and dynamic data visualization capabilities. Common features of a web 2.0 application include service-oriented architecture and integration with web services, including Web APIs that can be accessed over a network, such as the Internet, and executed on a remote system hosting the requested services. In some instances, web option provider module 710 may include a computer processor.

Figure 29:
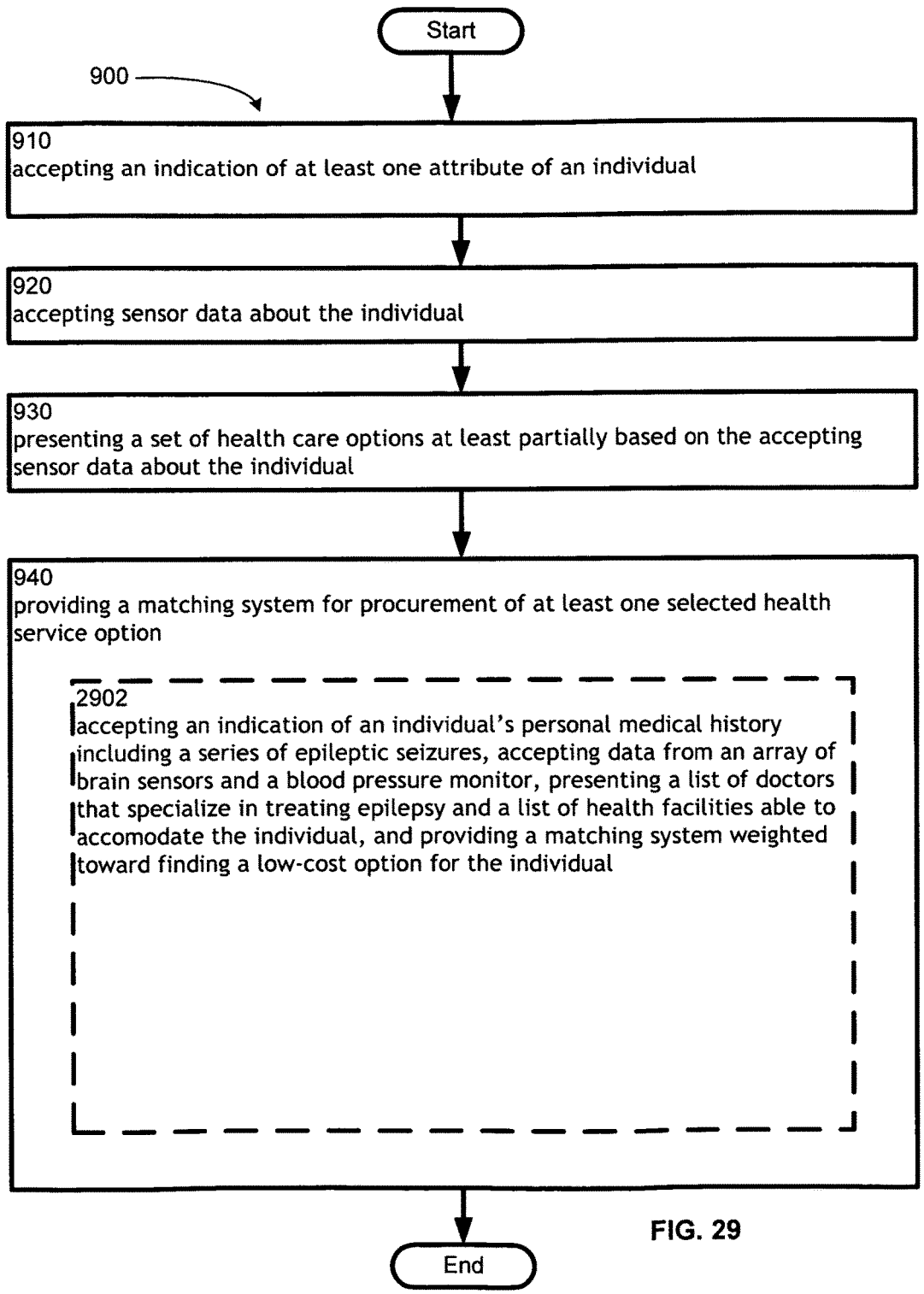
FIG. 29 illustrates an alternative embodiment of the operational flow of FIG. 9.

FIG. 29 illustrates alternative embodiments of the example operational flow 900 of FIG. 9. FIG. 29 illustrates example embodiments where operation 940 may include at least one additional operation. Additional operations may include operation 2902.

Operation 2902 illustrates accepting an indication of an individual's personal medical history including a series of epileptic seizures, accepting data from an array of brain sensors and a blood pressure monitor, presenting a list of doctors that specialize in treating epilepsy and a list of health facilities able to accomodate the individual, and providing a matching system weighted toward finding a low-cost option for the individual. For example, as shown in FIGS. 4 through 8, accepter module 602, data accepter module 604, presenter module 608, and provider module 610 can accept an indication of an individual's personal medical history including a series of epileptic seizures, accept data from an array of brain sensors and a blood pressure monitor, present a list of doctors that specialize in treating epilepsy and a list of health facilities able to accomodate the individual, and provide a matching system weighted toward finding a low-cost option for the individual. In some instances, accepter module 602 may include a computer processor. In some instances, data accepter module 604 may include a computer processor. In some instances, presenter module 608 may include a computer processor. In some instances, provider module 610 may include a computer processor.

Figure 30:
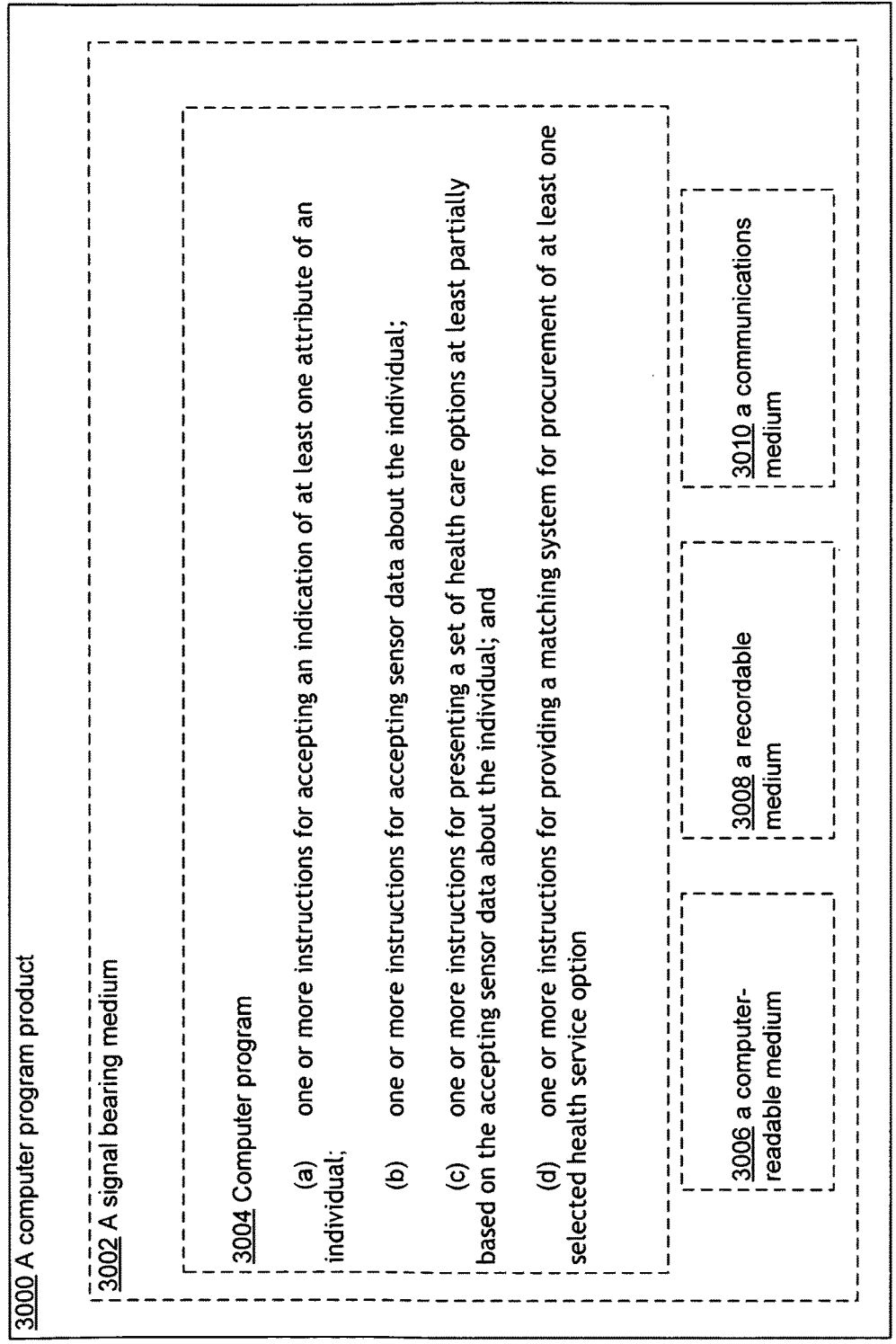
FIG. 30 illustrates a partial view of an example article of manufacture including a computer program product that includes a computer program for executing a computer process on a computing device related to health services planning and matching, which may serve as a context for introducing one or more processes and/or devices described herein.

FIG. 30 illustrates a partial view of an example computer program product 3000 that includes a computer program 3004 for executing a computer process on a computing device. An embodiment of the example computer program product 3000 is provided using a signal-bearing medium 3002, and may include one or more instructions for accepting an indication of at least one attribute of an individual, one or more instructions for accepting sensor data about the individual, one or more instructions for presenting a set of health care options at least partially based on the accepting sensor data about the individual, and one or more instructions for providing a matching system for procurement of at least one selected health service option. The one or more instructions may be, for example, computer executable and/or logic-implemented instructions. In one implementation, the signal-bearing medium 3002 may include a computer-readable medium 3006. In one implementation, the signal bearing medium 3002 may include a recordable medium 3008. In one implementation, the signal bearing medium 3002 may include a communications medium 3010.

FIG. 31 illustrates an example system 3100 in which embodiments may be implemented. The system 3100 includes a computing system environment. The system 3100 also illustrates the user 118 using a device 3104, which is optionally shown as being in communication with a computing device 3102 by way of an optional coupling 3106. The optional coupling 3106 may represent a local, wide-area, or peer-to-peer network, or may represent a bus that is internal to a computing device (e.g., in example embodiments in which the computing device 3102 is contained in whole or in part within the device 3104). A storage medium 3108 may be any computer storage media.

The computing device 3102 includes computer-executable instructions 3110 that when executed on the computing device 3102 cause the computing device 3102 to accept an indication of at least one attribute of an individual, accept sensor data about the individual, present a set of health care options at least partially based on the accepting sensor data about the individual, and provide a matching system for procurement of at least one selected health service option. As referenced above and as shown in FIG. 31, in some examples, the computing device 3102 may optionally be contained in whole or in part within the device 3104.

In FIG. 31, then, the system 3100 includes at least one computing device (e.g., 3102 and/or 3104). The computer-executable instructions 3110 may be executed on one or more of the at least one computing device. For example, the computing device 3102 may implement the computer-executable instructions 3110 and output a result to (and/or receive data from) the computing device 3104. Since the computing device 3102 may be wholly or partially contained within the computing device 3104, the device 3104 also may be said to execute some or all of the computer-executable instructions 3110, in order to be caused to perform or implement, for example, various ones of the techniques described herein, or other techniques.

The device 3104 may include, for example, a portable computing device, workstation, or desktop computing device. In another example embodiment, the computing device 3102 is operable to communicate with the device 3104 associated with the user 118 to receive information about the input from the user 118 for performing data access and data processing and presenting an output of the user-health test function at least partly based on the user data.

Although a user 140 is shown/described herein as a single illustrated figure, those skilled in the art will appreciate that a user 140 may be representative of a human user, a robotic user (e.g., computational entity), and/or substantially any combination thereof (e.g., a user may be assisted by one or more robotic agents). In addition, a user 140, as set forth herein, although shown as a single entity may in fact be composed of two or more entities. Those skilled in the art will appreciate that, in general, the same may be said of "sender" and/or other entity-oriented terms as such terms are used herein.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory.

Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A mobile computing device, comprising:
    circuitry configured for accepting at least one indication of at least one hematologic complaint of at least one individual via at least one user interface of the mobile computing device;
    circuitry configured for activating at least one image sensor of the mobile computing device at least partially based on at least one of anemia, malnutrition, or pulmonary illness being indicated by the at least one indication of at least one hematologic complaint of at least one individual;
    circuitry configured for accepting at least some image data related to the at least one individual from the at least one image sensor of the mobile computing device;
    circuitry configured for obtaining, by the mobile computing device, at least one indication of at least one level of hemoglobin of the at least one individual at least partially based on the at least some image data related to the at least one individual; and
    circuitry configured for determining, by the mobile computing device, at least one hematologic diagnosis associated with the at least one individual at least partially based on the at least one indication of at least one level of hemoglobin of the at least one individual.

2. The mobile computing device of claim 1, further comprising:
    circuitry configured for presenting one or more health care options at least partially based on the at least one hematologic diagnosis associated with the at least one individual.

3. The mobile computing device of claim 2, further comprising:
    circuitry configured for providing at least one matching system for procurement of at least one selected health care option.

4. The mobile computing device of claim 1, wherein circuitry configured for accepting at least one indication of at least one hematologic complaint of at least one individual via at least one user interface of the mobile computing device comprises:
    circuitry configured for accepting at least one indication of at least one physical attribute of at least one individual.

5. The mobile computing device of claim 1, wherein circuitry configured for accepting at least one indication of at least one hematologic complaint of at least one individual via at least one user interface of the mobile computing device comprises:
    circuitry configured for accepting at least one indication of at least one physical symptom of at least one individual.

6. The mobile computing device of claim 1, wherein circuitry configured for accepting at least one indication of at least one hematologic complaint of at least one individual via at least one user interface of the mobile computing device comprises:
    circuitry configured for accepting at least one indication of at least one mental attribute of at least one individual.

7. The mobile computing device of claim 1, wherein circuitry configured for accepting at least one indication of at least one hematologic complaint of at least one individual via at least one user interface of the mobile computing device comprises:
    circuitry configured for accepting at least one indication of at least one mental symptom of at least one individual.

8. The mobile computing device of claim 1, wherein circuitry configured for accepting at least one indication of at least one hematologic complaint of at least one individual via at least one user interface of the mobile computing device comprises:
    circuitry configured for accepting at least one indication of at least one mental impairment of at least one individual.

9. The mobile computing device of claim 1, wherein circuitry configured for accepting at least one indication of at least one hematologic complaint of at least one individual via at least one user interface of the mobile computing device comprises:
    circuitry configured for accepting at least one indication of at least one mental diagnosis of at least one individual.

10. The mobile computing device of claim 1, wherein circuitry configured for accepting at least one indication of at least one hematologic complaint of at least one individual via at least one user interface of the mobile computing device comprises:
    circuitry configured for accepting at least one indication of at least one past mental therapy of at least one individual.

11. The mobile computing device of claim 1, wherein circuitry configured for accepting at least some image data related to the at least one individual from the at least one image sensor of the mobile computing device comprises:
    circuitry configured for accepting at least some brain sensor data related to the at least one individual from the at least one sensor of the mobile computing device.

12. The mobile computing device of claim 1, wherein circuitry configured for accepting at least some image data related to the at least one individual from the at least one image sensor of the mobile computing device comprises:
    circuitry configured for accepting at least one brain activity surrogate marker related to the at least one individual from the at least one sensor of the mobile computing device.

13. The mobile computing device of claim 12, wherein circuitry configured for accepting at least one brain activity surrogate marker related to the at least one individual from the at least one sensor of the mobile computing device comprises:

circuitry configured for accepting at least one indication of one or more of iris dilation, iris constriction, gaze tracking, skin response, or voice response as the at least one brain activity surrogate marker related to the at least one individual from the at least one sensor of the mobile computing device.

14. The mobile computing device of claim 1, wherein circuitry configured for activating at least one image sensor of the mobile computing device at least partially based on at least one of anemia, malnutrition, or pulmonary illness being indicated by the at least one indication of at least one hematologic complaint of at least one individual comprises:
    circuitry configured for activating the at least one image sensor of the mobile computing device to obtain at least some sensor data of at least one particular type capable of being used to confirm at least one particular diagnosis in accordance with the at least one indication of at least one hematologic complaint of at least one individual.

15. The mobile computing device of claim 1, wherein circuitry configured for activating at least one image sensor of the mobile computing device at least partially based on at least one of anemia, malnutrition, or pulmonary illness being indicated by the at least one indication of at least one hematologic complaint of at least one individual comprises:
    circuitry configured for activating at least one camera of the mobile computing device to obtain one or more images.

16. The mobile computing device of claim 2, wherein circuitry configured for presenting one or more health care options at least partially based on the at least one hematologic diagnosis associated with the at least one individual comprises:
    circuitry configured for presenting one or more health care options at least partially based on at least one user preference associated with the at least one individual.

17. The mobile computing device of claim 16, wherein circuitry configured for presenting one or more health care options at least partially based on at least one user preference associated with the at least one individual comprises:
    circuitry configured for presenting one or more health care options at least partially based on one or more of at least one location preference or at least one time frame preference associated with the at least one individual.

18. The mobile computing device of claim 16, wherein circuitry configured for presenting one or more health care options at least partially based on at least one user preference associated with the at least one individual comprises:
    circuitry configured for presenting one or more health care options at least partially based on at least one health care provider compatible with at least one payment capacity associated with one or more of the at least one individual or at least one user.

19. The mobile computing device of claim 18, wherein circuitry configured for presenting one or more health care options at least partially based on at least one health care provider compatible with at least one payment capacity associated with one or more of the at least one individual or at least one user comprises:
    circuitry configured for presenting one or more health care options at least partially based on at least one health care provider accepting at least one of Medicare, Medicaid, uninsured patients, workers' compensation, or supplemental health insurance.

20. The mobile computing device of claim 16, wherein circuitry configured for presenting one or more health care options at least partially based on at least one user preference associated with the at least one individual comprises:
    circuitry configured for presenting one or more health care options at least partially based on at least one health care provider sharing one or more of at least one common gender, at least one common religion, at least one common race, or at least one common sexual orientation associated with one or more of the at least one individual or at least one user.

21. The mobile computing device of claim 2, wherein circuitry configured for presenting one or more health care options at least partially based on the at least one hematologic diagnosis associated with the at least one individual comprises:
    circuitry configured for presenting one or more of at least one surgery, at least one prescription drug therapy, at least one over-the-counter drug therapy, at least one chemotherapy, at least one radiation treatment, at least one ultrasound treatment, at least one laser treatment, at least one minimally invasive procedure, at least one antibody therapy, at least one cryotherapy, at least one hormonal therapy, or at least one gene therapy.

22. The mobile computing device of claim 2, wherein circuitry configured for presenting one or more health care options at least partially based on the at least one hematologic diagnosis associated with the at least one individual comprises:
    circuitry configured for presenting one or more of at least one treatment by at least one medical doctor, at least one treatment by at least one naturopathic doctor, at least one treatment by at least one acupuncturist, at least one treatment by at least one herbalist, at least one self-treatment, at least one course of no action for at least one period of time, or at least one course of taking no action until at least one specified indicator crosses at least one threshold.

23. The mobile computing device of claim 2, wherein circuitry configured for presenting one or more health care options at least partially based on the at least one hematologic diagnosis associated with the at least one individual comprises:
    circuitry configured for presenting one or more health care options at least partially based on one or more of at least one standard of care, at least one expert opinion, at least one insurance company evaluation, or at least some research data.

24. The mobile computing device of claim 2, wherein circuitry configured for presenting one or more health care options at least partially based on the at least one hematologic diagnosis associated with the at least one individual comprises:
    circuitry configured for presenting one or more health care options including one or more of at least one list of diagnosticians, at least one list of clinicians, at least one list of therapists, at least one list of dentists, at least one list of optometrists, at least one list of pharmacists, at least one list of nurses, at least one list of chiropractors, or at least one list of alternative medicine practitioners.

25. The mobile computing device of claim 2, wherein circuitry configured for presenting one or more health care options at least partially based on the at least one hematologic diagnosis associated with the at least one individual comprises:

circuitry configured for presenting one or more health care options including at least one list of treatment centers.

26. The mobile computing device of claim 25, wherein circuitry configured for presenting one or more health care options including at least one list of treatment centers comprises:
   circuitry configured for presenting one or more health care options including one or more of at least one list of clinics, at least one list of hospitals, at least one list of medical offices, or at least one list of alternative medicine practice offices.

27. The mobile computing device of claim 3, wherein circuitry configured for providing at least one matching system for procurement of at least one selected health care option comprises:
   circuitry configured for providing an auction system for procurement of the at least one selected health care option.

28. The mobile computing device of claim 27, wherein circuitry configured for providing an auction system for procurement of the at least one selected health care option comprises:
   circuitry configured for providing a reverse auction system for procurement of the at least one selected health care option.

29. The mobile computing device of claim 27, wherein circuitry configured for providing an auction system for procurement of the at least one selected health care option comprises:
   circuitry configured for providing one or more of a no-bid auction system, an English auction system, a proxy bidding system, a Dutch auction system, a buyout auction, or a sealed first-price auction.

30. The mobile computing device of claim 3, wherein circuitry configured for providing at least one matching system for procurement of at least one selected health care option comprises:
   circuitry configured for providing at least one matching system weighted toward rapid procurement of the at least one selected health care option.

31. The mobile computing device of claim 3, wherein circuitry configured for providing at least one matching system for procurement of at least one selected health care option comprises:
   circuitry configured for providing at least one matching system weighted toward procurement of one or more low-cost health care options in accordance with the at least one selected health care option.

32. The mobile computing device of claim 3, wherein circuitry configured for providing at least one matching system for procurement of at least one selected health care option comprises:
   circuitry configured for providing at least one matching system weighted toward procurement of one or more high-quality health care options in accordance with the at least one selected health care option.

33. The mobile computing device of claim 3, wherein circuitry configured for providing at least one matching system for procurement of at least one selected health care option comprises:
   circuitry configured for providing at least one matching system weighted toward procurement of one or more locally-available health care options in accordance with the at least one selected health care option.

34. A mobile computing device, comprising:
   at least one processing device; and
   one or more instructions which, when executed on the at least one processing device, configure the at least one processing device to perform one or more operations including at least:
      accepting at least one indication of at least one hematologic complaint of at least one individual via at least one user interface of the mobile computing device;
      activating at least one image sensor of the mobile computing device at least partially based on at least one of anemia malnutrition or pulmonary illness being indicated by the at least one indication of at least one hematologic complaint of at least one individual;
      accepting at least some image data related to the at least one individual from the at least one image sensor of the mobile computing device;
      obtaining, by the mobile computing device, at least one indication of at least one level of hemoglobin of the at least one individual at least partially based on the at least some image data related to the at least one individual; and
      determining, by the mobile computing device, at least one hematologic diagnosis associated with the at least one individual at least partially based on the at least one indication of at least one level of hemoglobin of the at least one individual.

35. A method for a mobile device, comprising:
   accepting at least one indication of at least one hematologic complaint of at least one individual via at least one user interface of the mobile computing device;
   activating at least one image sensor of the mobile computing device at least partially based on at least one of anemia, malnutrition, or pulmonary illness being indicated by the at least one indication of at least one hematologic complaint of at least one individual;
   accepting at least some image data related to the at least one individual from the at least one image sensor of the mobile computing device;
   obtaining, by the mobile computing device, at least one indication of at least one level of hemoglobin of the at least one individual at least partially based on the at least some image data related to the at least one individual; and
   determining, by the mobile computing device, at least one hematologic diagnosis associated with the at least one individual at least partially based on the at least one indication of at least one level of hemoglobin of the at least one individual,
   wherein at least one of the accepting, activating, obtaining, or determining is at least partially implemented using at least one processing device.

36. The mobile computing device of claim 1, wherein circuitry configured for activating at least one image sensor of the mobile computing device at least partially based on at least one of anemia, malnutrition, or pulmonary illness being indicated by the at least one indication of at least one hematologic complaint of at least one individual comprises:
   circuitry configured for activating the at least one image sensor and activating at least one microphone of the mobile computing device to obtain at least some audio data.

37. The mobile computing device of claim 1, wherein circuitry configured for activating at least one image sensor of the mobile computing device at least partially based on at least one of anemia malnutrition or pulmonary illness being indicated by the at least one indication of at least one hematologic complaint of at least one individual comprises:

circuitry configured for activating at least one sensor of the mobile computing device at a certain time of day at least partially based on the at least one indication of at least one attribute of at least one individual.

38. The mobile computing device of claim 1, wherein circuitry configured for activating at least one image sensor of the mobile computing device at least partially based on at least one of anemia malnutrition or pulmonary illness being indicated by the at least one indication of at least one hematologic complaint of at least one individual comprises:

circuitry configured for activating at least one sensor of the mobile computing device at least partially based on a physiological condition indicated by the at least one indication of at least one hematologic complaint of at least one individual.

39. The mobile computing device of claim 1, wherein circuitry configured for activating at least one image sensor of the mobile computing device at least partially based on at least one of anemia malnutrition or pulmonary illness being indicated by the at least one indication of at least one hematologic complaint of at least one individual comprises:

circuitry configured for activating at least one sensor of the mobile computing device at one or more of at least one specified time or at least one specified time interval at least partially based on the at least one indication of at least one attribute of at least one individual.

40. The mobile computing device of claim 39, wherein circuitry configured for activating at least one sensor of the mobile computing device at one or more of at least one specified time or at least one specified time interval at least partially based on the at least one indication of at least one attribute of at least one individual comprises:

circuitry configured for activating at least one sensor of the mobile computing device after a specified interval of time following an individual indicating a specified painful sensation.

41. The mobile computing device of claim 1, wherein circuitry configured for determining, by the mobile computing device, at least one hematologic diagnosis associated with the at least one individual at least partially based on the at least one indication of at least one level of hemoglobin of the at least one individual comprises:

circuitry configured for determining, by the mobile computing device, at least one hematologic diagnosis associated with the at least one individual at least partially based on at least one query with respect to the at least some image data related to the at least one individual, the at least some image data being at least one of organized, keyed to, or accessible using one or more reference health-related status indicators, to obtain at least one hematologic diagnosis associated with the at least one individual.

42. The mobile computing device of claim 1, wherein circuitry configured for determining, by the mobile computing device, at least one hematologic diagnosis associated with the at least one individual at least partially based on the at least one indication of at least one level of hemoglobin of the at least one individual comprises:

circuitry configured for using at least one third party reference accessible via at least one communications network to determine, at least partially via at least one query transmitted via at least one network interface of the mobile computing device, the at least one hematologic diagnosis associated with the at least individual received at least partially based on the at least one indication of at least one level of hemoglobin of the at least one individual.

43. The mobile computing device of claim 1, wherein circuitry configured for activating at least one image sensor of the mobile computing device at least partially based on at least one of anemia malnutrition or pulmonary illness being indicated by the at least one indication of at least one hematologic complaint of at least one individual comprises:

circuitry configured for activating at least one image sensor of the mobile computing device to obtain at least one hematologic indication associated with the at least one individual.

44. The mobile computing device of claim 43, wherein circuitry configured for activating at least one image sensor of the mobile computing device to obtain at least one hematologic indication associated with the at least one individual comprises:

circuitry configured for activating at least one image sensor of the mobile computing device to obtain at least one estimate of at least one level of hemoglobin associated with the at least one individual.

45. The mobile computing device of claim 43, wherein circuitry configured for activating at least one image sensor of the mobile computing device to obtain at least one hematologic indication associated with the at least one individual comprises:

circuitry configured for activating at least one image sensor of the mobile computing device to obtain at least one inference of at least one level of hemoglobin associated with the at least one individual.

46. The mobile computing device of claim 1, wherein circuitry configured for activating at least one image sensor of the mobile computing device at least partially based on at least one of anemia malnutrition or pulmonary illness being indicated by the at least one indication of at least one hematologic complaint of at least one individual comprises:

circuitry configured for activating at least one audio sensor of the mobile computing device to obtain at least one recording associated with the at least one individual at least partially based on at least one indication of respiratory disorder of the at least one individual as the at least one hematologic complaint.

47. The mobile computing device of claim 1, wherein circuitry configured for activating at least one image sensor of the mobile computing device at least partially based on at least one of anemia malnutrition or pulmonary illness being indicated by the at least one indication of at least one hematologic complaint of at least one individual comprises:

circuitry configured for activating at least one audio sensor of the mobile computing device to obtain at least one recording associated with the at least one individual at least partially based on at least one indication of abnormal respiration of the at least one individual as the at least one hematologic complaint.

48. The mobile computing device of claim 47, wherein circuitry configured for activating at least one audio sensor of the mobile computing device to obtain at least one recording associated with the at least one individual at least partially based on at least one indication of abnormal respiration of the at least one individual as the at least one hematologic complaint comprises:

circuitry configured for activating at least one audio sensor of the mobile computing device to obtain at least one recording associated with monitoring of breathing of the at least one individual at least partially based on at least one indication of abnormal respiration of the at least one individual as the at least one hematologic complaint.

49. The mobile computing device of claim 48, wherein circuitry configured for activating at least one audio sensor of the mobile computing device to obtain at least one recording associated with monitoring of breathing of the at least one individual at least partially based on at least one indication of abnormal respiration of the at least one individual as the at least one hematologic complaint comprises:
　circuitry configured for activating at least one microphone of the mobile computing device to obtain at least one recording associated with the at least one individual blowing into the at least one microphone of the mobile computing device at least partially based on at least one indication of abnormal respiration of the at least one individual as the at least one hematologic complaint.

50. The mobile computing device of claim 1, wherein circuitry configured for activating at least one image sensor of the mobile computing device at least partially based on at least one of anemia, malnutrition, or pulmonary illness being indicated by the at least one indication of at least one hematologic complaint of at least one individual comprises:
　circuitry configured for activating at least one non-collumnated light source to provide illumination of at least a portion of the at least one individual; and
　circuitry configured for activating at least one image sensor of the mobile computing device to obtain one or more images of the at least a portion of the at least one individual.

51. The mobile computing device of claim 50, wherein circuitry configured for activating at least one non-collumnated light source to provide illumination of at least a portion of the at least one individual comprises:
　circuitry configured for activating at least one non-collumnated light source of the mobile computing device to provide illumination of at least a portion of the at least one individual.

\* \* \* \* \*